US006875606B1

(12) United States Patent
Leonard et al.

(10) Patent No.: US 6,875,606 B1
(45) Date of Patent: Apr. 5, 2005

(54) HUMAN α-7 NICOTINIC RECEPTOR PROMOTER

(75) Inventors: Sherry Leonard, Denver, CO (US); Robert Freedman, Englewood, CO (US)

(73) Assignee: The United States of America as represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 08/956,518

(22) Filed: Oct. 23, 1997

(51) Int. Cl.$^7$ .................... C07H 21/02; C12N 15/11; C12N 15/63; C12N 15/81; C12N 15/85

(52) U.S. Cl. ............... 435/325; 536/24.1; 536/23.1; 435/320.1; 435/252.3; 435/254.2

(58) Field of Search ............... 536/23.1, 23.5, 536/24.1, 24.31; 435/320.1, 325, 252.3, 254.2

(56) References Cited

U.S. PATENT DOCUMENTS

| | | | |
|---|---|---|---|
| 4,650,764 A | 3/1987 | Temin et al. | |
| 4,683,195 A | 7/1987 | Mullis et al. | |
| 4,683,202 A | 7/1987 | Mullis | |
| 4,861,719 A | 8/1989 | Miller | |
| 4,946,778 A | 8/1990 | Ladner et al. | |
| 4,965,188 A | 10/1990 | Mullis et al. | |
| 4,980,289 A | 12/1990 | Temin et al. | |
| 5,124,263 A | 6/1992 | Temin et al. | |
| 5,322,770 A | 6/1994 | Gelfand | |
| 5,399,346 A | 3/1995 | Anderson et al. | |
| 5,459,127 A | 10/1995 | Felgner et al. | |
| 5,580,859 A | 12/1996 | Felgner et al. | |
| 5,589,466 A | 12/1996 | Felgner et al. | |
| 5,837,489 A | * 11/1998 | Elliott et al. ............... | 435/69.1 |

FOREIGN PATENT DOCUMENTS

| | | |
|---|---|---|
| EP | 0178220 B1 | 4/1986 |
| EP | 0453243 A2 | 10/1991 |
| WO | WO 89/07150 | 8/1989 |
| WO | WO 90/02806 | 3/1990 |
| WO | WO 90/13678 | 11/1990 |
| WO | WO 92/05263 | 4/1992 |
| WO | WO 93/03367 | 2/1993 |
| WO | WO 94/21807 | 9/1994 |
| WO | WO 94/26914 | 11/1994 |
| WO | WO 95/02697 | 1/1995 |
| WO | WO 95/07358 | 3/1995 |
| WO | WO 95/18863 | 7/1995 |
| WO | WO 95/21931 | 8/1995 |
| WO | WO 96/15244 | 5/1996 |
| WO | WO 96/17823 | 6/1996 |
| WO | WO 96/25508 | 8/1996 |

OTHER PUBLICATIONS

Rudinger, In "Peptide Hormoner" (ed. J.A. Parsons) University Park Press, Baltimore, pp. 1–7, 1976.*
LeClerc et al. Nature 297:596–597, 1982.*
Adler et al., "Normalization by Nicotine of Deficient Auditory Sensory Gating in the Relatives of Schizophrenics," *Biol. Psych.* 32: 607–616 (1992).
Adler et al., "Normalization of Auditory Physiology by Cigarette Smoking in Schizophrenic Patients," *Am. J. Psychol.* 150: 1856–1861 (1993).
Adler et al., "Neurophysiological Studies of Sensory Gating in Rats: Effects of Amphetamine, Phencyclidine, and Haloperidol," *Biol. Psychiat.* 21: 787–798 (1986).
Adler et al., "Neurophysiological Evidence for a Defect in Neuronal Mechanisms Involved in Sensory Gating in Schizophrenia," *Biol. Psychiat.* 17: 639–654 (1982).
Albertsen et al., "Construction and characterization of a yeast artificial chromosome library containing seven haploid human genome equivalents," *Proc. Natl. Acad. Sci.* 87: 4256–4260 (1990).
Alkondon and Albuquerque, "Diversity of Nicotinic Acetylcholine Receptors in Rat Hippocampal Neurons. I. Pharmacological and Functional Evidence for District Structural Subtypes," *J. Pharm. Ex. Ther.* 265: 1455–1473 (1993).
Amar et al., "Agonist pharmacology of the neuronal α7 nicotinic receptor expressed in *Xenopus* oocytes," *FEBS* 327: 284–288 (1993).
Anderson and Young, "Quantitative Filter Hybridization," in *Nucleic Acid Hybridization A Practical Approach*, Hames and Higgins (eds.), pp. 73–109, IRL Press (1985).
Barnes, "PCR Amplification of up to 35–kb DNA with high fidelity and high yield from λ bacteriophage templates," *Proc. Natl. Acad. Sci. U.S.A.* 91: 2216–2220 (1994).
Beard et al., "Transcription Mapping of Mouse Adenovirus Type 1 Early Region 3," *Virology*, pp. 75–81 (1990).
Beeson et al., "The human muscle nicotinic acetylcholine receptor α–subunit exists as two isoforms: a novel exon," *EMBO J.* 9: 2101–2106 (1990).
Bender et al., "Evidence that the Packaging Signal of Moloney Murine Leukemia Virus Extends into the gag Region," *J. Virol.* 61: 1639–1646 (1987).
Bernstein et al., "Gene Transfer with Retrovirus Vectors," *Genet. Eng.* 7: 235–261 (1985).

(Continued)

Primary Examiner—Gary Kunz
Assistant Examiner—Robert C. Hayes
(74) Attorney, Agent, or Firm—Medlen & Carroll, LLP

(57) ABSTRACT

The present invention is directed to methods and compositions related to α7 acetylcholine nicotinic receptor genes, in particular, the human α7 nicotinic acetylcholine receptor gene. This α7 acetylcholine nicotinic receptor gene is associated with the pathophysiological aspects of the disease schizophrenia. The present invention further provides methods and compositions to screen populations for abnormal α7, as well as methods and compositions for development of therapeutics.

6 Claims, 8 Drawing Sheets

OTHER PUBLICATIONS

Bessis et al., "Negative regulatory elements upstream of a novel exon of the neuronal nicotinic acetylcholine receptor of α2 subunit gene," *Nucl. Acids. Res.* 21: 2185–2192 (1993).

Bickford–Wimer et al., "Auditory Sensory Gating in Hippocampal Neurons: A Model System in the Rat," *Biol. Psychiat.* 27: 183–192 (1990).

Bickford and Wear, "Restoration of sensory gating of auditory evoked response by nicotine in fimbria–fornix lesioned rats," *Brain Res.* 705: 235–240 (1995).

Biedler et al., "Multiple Neurotransmitter Synthesis by Human Neuroblastoma Cell Lines and Clones," *Cancer Res.* 38: 3751–3757 (1978).

Blount and Merlie, "Mutational Analysis of Muscle Nicotinic Acetylcholine Receptor Subunit Assembly," *J. Cell Biol.* 111: 2613–2622 (1990).

Boshart et al., "A Very Strong Enhancer is Located Upstream of an Immediate Early Gene of Human Cytomegalovirus," *Cell* 41:521–530 (1985).

Boutros and Overall, "Replication and Extension of P50 Findings in Schizophrenia," *Clin. Electroencephalog.* 22: 40–45 (1991).

Braff et al., "Gating and Habituation of the Startle Reflex in Schizophrenic Patients," *Arch. Gen. Psychiat.* 49: 206–215 (1992).

Breier et al., "National Institute of Mental Health Longitudinal Study of Chronic Schizophrenia, Prognosis and Predictors of Outcome," *Arch. Gen. Psychiat.*, 48: 239–246 (1991).

Brownstein et al., "Isolation of Single–Copy Human Genes from a Library of Yeast Artifical Chromosome Clones," *Science* 244: 1348–1351 (1989).

Burke et al., "Cloning of Large Segments of Exogenous DNA into Yeast by Means of Artificial Chromosome Vectors" *Science* 236: 806–812 (1987).

Calzolari et al., "Psychiatric Disorder in a Familial 15;18 Translocation and Sublocalization of Myelin Basic Protein to 18q22.3," *Am. J. Med. Genet.* 67: 154–161 (1996).

Cameron et al., "Dendritic Cells Exposed to Human Immunodeficiency Virus Type–1 Transmit a Vigorous Cytophathic Infection to CD4$^+$T Cells," *Science* 257: 383–387 (1992).

Casaubon et al., "The Gene Responsible for a Severe Form of Peripheral Neuropathy and Agenesis of the Corpus Callosum Maps to Chromosome 15q," *Am. J. Hum. Genet.* 58: 28–34 (1996).

Chamberlin et al., "New RNA Polymerase from *Escherichia coli* infected with Bacteriophage T7," *Nature* 228:227–231 (1970).

Chomczynski and Sacchi, "Single–Step Method of RNA Isolation by Acid Guanidinium Thiocyanate–Phenol–Chloroform Extraction," *Anal. Biochem.* 162: 156–159 (1987).

Chumakov et al., "Continuum of overlapping clones spanning the entire human chromosome 21q," *Nature* 359: 380–386 (1992).

Clarke, "Prader–Willi Syndrome and Psychoses," *Brit. J. Psychiat.* 163: 680–684 (1993).

Cole et al., "The EBV–Hybridoma Technique and its Application to Human Lung Cancer," in *Monoclonal Antibodies and Cancer Therapy*, Reisfeld et al. (eds.), pp. 77–96, Alan R. Liss, Inc. (1985).

Conti–Tronconi et al., "Brain and Muscle nicotinic acetylcholine receptors are different but homologous proteins," *Proc. Natl. Acad. Sci U.S.A.* 82: 5208–5212 (1985).

Coon et al., "Search for Mutations in the β1 GABA$_A$ Receptor Subunit Gene in Patients with Schizophrenia," *Am. J. Med. Genet.* 54: 12–20 (1994).

Coon et al., "Use of a Neurophysiological Trait in Linkage Analysis of Schizophrenia," *Biol. Psychiat.* 34: 277–289 (1993).

Cooper et al., "Pentameric structure and subunit stoichiometry of a neuronal nicotinic acetylcholine receptor," *Nature* 350: 235–238 (1991).

Cote et al., "Generation of human monoclonal antibodies reactive with cellular antigens," *Proc. Natl. Acad. Sci. U.S.A.* 80: 2026–2030 (1983).

Couturier et al., "A Neuronal Nicotinic Acetylcholine Receptor Subunit (α7) Is Developmentally Regulated and Forms a Homo–Oligomeric Channel Blocked by α–BTX," *Neuron* 5: 847–856 (1990).

Cullum et al., "Neurophysiological and neuropsychlogical evidence for attentional dysfunction in schizophrenia," *Schizophrenia Res.* 10: 131–141 (1993).

Curiel et al., "High–Efficiency Gene Transfer Mediated by Adenovirus Coupled to DNA–Polylysine Complexes," *Hum. Gene Ther.* 3: 147–154 (1992).

De Amicis et al., "Reaction Time Crossover as a Marker of Schizophrenia and of Higher Functioning," *J. Nerv. Ment. Dis.* 174: 177–179 (1986).

deLeon et al., "Schizophrenia and Smoking: An Epidemiological Survey in a State Hospital," *Am. J. Psychiat.* 152: 453–455 (1995).

Den–Dunnen et al., "Topography of the Duchenne Muscular Dystrophy (DMD) Gene: FIGE and cDNA Analysis of 194 Cases Reveals 115 Deletions and 13 Duplications," *Am. J. Hum. Genet.* 45: 835–847 (1989).

Deneris et al., "Genes Encoding Neuronal Nicotinic Acetylcholine Receptors," *Clin. Chem.* 35: 731–737 (1989).

Dijkema et al., "Cloning and expression of the chromosomal immune interferon gene of the rat," *EMBO J.* 4:761–767 [1985].

Dominguez del Toro et al., "Immunocytochemical Localization of the α7 Subunit of the Nicotinic Acetylcholine Receptor in the Rat Central Nervous System," *J. Comp. Neurol.* 349: 325–342 (1994).

Eaton, "Epidemiology of Schizophrenia," *Epidemiol. Rev.* 7: 105–126 (1985).

Elgoyhen et al., "α9: An Acetylcholine Receptor with Novel Pharmacological Properties Expressed in Rat Cochlear Hair Cells," *Cell* 79: 705–715 (1994).

Endicott and Spitzer, "A Diagnostic Interview, The Schedule for Affective Disorders and Schizophrenia," *Arch. Gen. Psychiat.* 35: 837–844 (1978).

Erwin et al., "Midlatency Auditory Evoked Responses in Schizophrenia," *Biol. Psychiat.* 30: 430–442 (1991).

Felgner and Ringold, "Cationic liposome–mediated transfection," *Nature* 337: 387–388 (1989).

Felgner et al., "Lipofection: A highly efficient, lipid–mediated DNA–transfection procedure," *Proc. Natl. Acad. Sci. U.S.A.* 84: 7413–7417 (1987).

Freedman et al., "β–Bungarotoxin Binding to Hippocampal Interneurons: Immunocytochemical Characterization and Effects on Growth Factor Expression," *J. Neurosci.* 13: 1965–1975 (1993).

Freedman et al., "Elementary neuronal dysfunctions in schizophrenia," *Schlz. Res.* 4: 233–243 (1991).

Freedman et al., "Schizophrenia and Nicotinic Receptors," *Harvard Rev. Psychiat.* 2: 179–192 (1994).

Freedman et al., "Evidence in Postmortem Brain Tissue for Decreased Numbers in Hippocampal Nicotinic Receptors in Schizophrenia," *Biol. Psychiat.* 38: 22–33 (1995).

Galzi et al., "Functional Architecture of the Nicotinic Acetylcholine Receptor: From Electric Organ to Brain," *Ann. Rev. Pharmacol.* 31: 37–72 (1991).

Goff et al., "Cigarette Smoking in Schizophrenia: Relationship to Psychopathology and Medication Side Effects," *Am. J. Psychiat.* 149: 1189–1194 (1992).

Goff et al., "Neural Origins of Long Latency Evoked Potentials Recorded from the Depth and from the Cortical Surface of the Brain in Man," *Prog. Clin. Neurophysiol.* 7: 126–145 (1980).

Goldman et al., "Members of a Nicotinic Acetylcholine Receptor Gene Family Are Expressed in Different Regions of the Mammalian Central Nervous System," *Cell* 48: 965–973 (1987).

Gorman et al., "The Rous sarcoma virus long terminal repeat is a strong promoter when introduced into a variety of eukaryotic cells by DNA–mediated transfection," *Proc. Natl. Acad. Sci. USA* 79: 6777–6781 [1982].

Graham and van der Eb, "A New Technique for the Assay of Infectivity of Human Adenovirus 5 DNA," *Virology* 52: 456–467 [1973].

Green, "Biochemical Mechanisms of Constitutive and Regulated Pre–mRNA Splicing," *Ann. Rev. Cell. Biol.* 7: 559–599 (1991).

Griffith et al., "Effects of sound intensity on a midlatency evoked response to repeated auditory stimuli in schizophrenic and normal subjects," *Psychophysiology* 32: 460–466 (1995).

Hamera et al., "Alcohol, Cannabis, Nicotine, and Caffeine Use and Symptom Distress in Schizophrenia," *J. Nerv. Mental Dis.* 183: 559–565, (1995).

Hershman et al., "$GABA_B$ antagonists diminish the inhibitory gating of auditory response in the rat hippocampus," *Neurosci. Lett.* 190: 133–136 (1995).

Holzman et al., "A Single Dominant Gene Can Account for Eye Tracking Dysfunctions and Schizophrenia in Offspring of Discordant Twins," *Arch. Gen. Psychiat.* 45: 641–647 (1988).

Hu and Worton, "Partial Gene Duplication as a Cause of Human Disease," *Hum. Mutat.* 1: 3–12 (1992).

Huse et al., "Generation of a Large Combinatorial Library of the Immunoglobulin Repertoire in Phage Lambda," *Science* 246: 1275–1281 (1989).

Hyman, "Schizophrenia," in *Scientific American Medicine*, 13 VII: 1–5, Dale and Federman (eds.), New York, New York (1994).

Judd et al., "Sensory Gating Deficits in Schizophrenia: New Results," *Am. J. Psychiat.* 149: 488–493 (1992).

Kacian et al., "A Replicating RNA Molecule Suitable for a Detailed Analysis of Extracellular Evolution and Replication," *Proc. Natl. Acad. Sci. USA* 69: 3038–3042 [1972].

Kaplitt et al., "Expression of a Functional Foreign Gene in Adult Mammalian Brain following in Vivo Transfer via a Herpes Simplex Virus Type 1 Defective Viral Vector," *Mol. Cell. Neurosci.* 2: 320–330 (1991).

Kim et al., "Use of the human elongation factor 1α promoter as a versatile and efficient expression system," *Gene* 91:217–223 [1990].

Kohler and Milstein, "Continuous cultures of fused cells secreting antibody of predefined specificity," *Nature* 256: 495–497 [1975].

Kozbor et al., "The production of monoclonal antibodies from human lymphocytes," *Immun. Today* 4: 72–79 (1983).

Kruglyak et al., "Parametric and Nonparametric Linkage Analysis: A Unified Multipoint Approach," *Am. J. Hum. Genet.* 58: 1347–1363 (1996).

Kuo et al., "Efficient Gene Transfer Into Primary Murine Lymphocytes Obviating the Need for Drug Selection," *Blood* 82: 845–852 (1993).

Lamond, "The Spliceosome," *BioEssays* 15: 595–603 (1993).

La Salle et al., "An Adenovirus Vector for Gene Transfer into Neurons and Glia in the Brain," *Science* 259: 988–990 (1993).

Lathrop et al., "Strategies for multilocus linkage analysis in humans," *Proc. Natl. Acad. Sci. U.S.A.* 81: 3443–3446 (1984).

Lebkowski et al., "Adeno–Associated Virus: a Vector System for Efficient Introduction and Integration of DNA into a Variety of Mammalian Cell Types," *Mol. Cell. Biol.* 8: 3988–3996 (1988).

Lehrman et al., "Duplication of Seven Exons in LDL Receptor Gene Caused by Alu–Alu Recombination in a Subject with Familial Hypercholesterolemia," *Cell* 48: 827–835 (1987).

Lindstrom et al., "Neuronal Nicotinic Receptor Subtypes," *Ann. NY Acad. Sci.* 757: 100–116 (1996).

Lukas and Bencherif, "Heterogeneity and Regulation of Nicotinic Acetylcholine Receptors," *Int. Rev. Neurobiol.* 34: 25–131 (1992).

Luntz–Leybman et al., "Cholinergic gating of response to auditory stimuli in rat hippocampus," *Brain. Res.* 587: 130–136 (1992).

Machy et al., "Gene transfer from targeted liposomes to specific lymphoid cells by electroporation," *Proc. Natl. Acad. Sci. U.S.A.* 85: 8027–8031 (1988).

Mäkelä et al., "Whole–head mapping of middle–latency auditory evoked magnetic fields," *Electroencephalogr. Clin. Neurophysiol.* 92: 414–421 (1994).

Maniatis et al., "Regulation of Inducible and Tissue–Specific Gene Expression," *Science* 236: 1237–1244 (1987).

Mann et al., "Construction of a Retrovirus Packaging Mutant and Its Use to Produce Helper–Free Defective Retrovirus," *Cell* 33: 153–159 (1983).

Markowitz et al., "A Safe Packaging Line for Gene Transfer: Separating Viral Genes on Two Different Plasmids," *J. Virol.* 62: 1120–1124 (1988).

Marks and Collins, "Characterization of Nicotine Binding in Mouse Brain and Comparison with the Binding of α–Bungarotoxin and Quinuclidinyl Benzilate," *Mol. Pharmacol.* 22: 554 (1982).

Marks et al., "Nicotinic Binding Sites in Rat and Mouse Brain: Comparison of Acetylcholine, Nicotine, and α–Bungarotoxin," *Mol. Pharmacol.* 30: 427–437 (1986).

Matter–Sadzinski et al., "Neuronal specificity of the α7 nicotinic acetylcholine receptor promoter develops during morphogenesis of the central nervous system," *EMBO J.* 11: 4529–4538 (1992), Maue et al., "Neuron–Specific Expression of the Rat Brain Type II Sodium Channel Gene Is Directed by Upstream Regulatory Elements," *Neuron* 4: 223–231 (1990).

Melissari et al., "Mitral valve prolapse in a case of Marfan syndrome with congenital cardiac disease, chronic obstructive pulmonary disease and schizophrenia," *Pathologica* 87: 78–81 (1995).

Miller et al., "A simple salting out procedure for extracting DNA from human nucleated cells," Nucl. Acids Res. 16: 1215 (1988).

Miller and Rosman, "Improved Retroviral Vectors for Gene Transfer and Expression," BioTechniques 7: 980–990 (1992).

Miller and Freeman, "The Activity of Hippocampal Interneurons and Pyramidal Cells During The Response of the Hippocampus to Repeated Auditory Stimuli," Neurosci. 69: 371–381 (1995).

Mizushima and Nagata, "pEF–BOS, a powerful mammalian expression vector," Nucl. Acids. Res. 18:5322 (1990).

Nagamoto et al., "Sensory Gating in Schizophrenics and Normal Controls: Effects of Changing Stimulation Interval," Biol. Psychiat. 25: 549–561 (1989).

Nagamoto et al., "Gating of Auditory P50 in Schizophrenics: Unique Effects of Clozapine," Biol. Psychiat. 40: 181–188 (1996).

Newland et al., "Functional and non–functional isoforms of the human muscle acetylcholine receptor," J. Phsyiol. 489: 767–778 (1995).

Nielsen et al., "Peptide nucleic acids (PNAs): Potential anti–sense and anti–gene agents," Anticancer Drug Des. 8:53–63 (1993).

Orr–Urtreger et al., "Cloning and Mapping of the Mouse α7–Neuronal Nicotinic Acetylcholine Receptor," Genomics 26: 399–402 (1995).

Ott, "Computer–simulation methods in human linkage analysis," Proc. Natl. Acad. Sci. U.S.A. 86: 4175–2178 (1989).

Patrick et al., "Molecular Biology of Nicotinic Acetylcholine Receptors," Ann. NY Acad. Sci. 505: 194 (1987).

Pauly et al., "Glucocorticoid Regulation of Sensitivity to Nicotine," in The Biology of Nicotine: Current Research Issues, Lippiello et al. (eds.), pp. 121–139, Raven Press, New York (1992).

Peng et al., "Human α7 Acetylcholine Receptor: Cloning of the α7 Subunit from the SH–SY5Y Cell Line and Determination of Pharmacological Properties of Native Receptors and Functional α7 Homomers Expressed in Xenopus Oocytes," Mol. Pharm. 45: 546–554 (1994).

Pulver et al., "Follow–Up of a Report of a Potential Linkage for Schizophrenia on Chromosome 22q12–q13.1: Part 2," Am. J. Med. Genet. 54: 44–50 (1994).

Research Disclosure 371005 p. 129–130 (1995).

Risch, "Genetic Linkage and Complex Diseases, With Special Reference to Psychiatric Disorders," Genet. Epidemiol. 7: 3–16 (1990).

Rollins et al., "Cellular Localization of α–Bungarotoxin Binding and α7 mRNA in the Hippocampus Related to Auditory Gating in the Awake, Behaving Rat," Soc. Neurosci. Abst. 22: 1272 (1996).

Saksela et al., "Human immunodeficiency virus type 1 mRNA expression in peripheral blood cells predicts disease progression independently of the numbers of CD4+lymphocytes," Proc. Natl. Acad. Sci. U.S.A. 91: 1104–1108 (1994).

Saksela et al., "High Viral Load in Lymph Nodes and Latent Human Immunodeficiency Virus (HIV) in Peripheral Blood Cells of HIV–1 Infected Chimpanzees," J. Virol. 67: 7423–7427 (1993).

Sambrook et al., Molecular Cloning: A Laboratory Manual, 2nd ed., pp. 7.39–7.52, 9.31–9.58, 16.6–16.15, Cold Spring Laboratory Press, New York (1989).

Samulski et al., "A Recombinant Plasmid from Which an Infectious Adeno–Associated Virus Genome Can Be Excised in Vitro and Its Use To Study Viral Replication," J. Virol. 61: 3096–3101 (1987).

Samulski et al., "Helper–Free Stocks of Recombinant Adeno–Associated Viruses: Normal Integration Does Not Require Viral Gene Expression," J. Virol. 63: 3822–3828 (1989).

Sauerwald et al., "The 5'–Flanking Region of the Synapsin 1 Gene," J. Biol. Chem. 265: 14932–14937 (1990).

Schmid, "Alu: Structure, Origin, Evolution, Significance and Function of One–Tenth of Human DNA," Prog. Nucl. Acid Res. 53: 283–319 (1996).

Schoepfer et al., "Brain α–Bungarotoxin Binding Protein cDNAs and MAbs Reveal Subtypes of This Branch of the Ligand–Gated Ion Channel Gene Superfamily," Neuron 5: 35–48 (1990).

Séguéla et al., "Molecular Cloning, Functional Properties, and Distribution of Rat Brain α7: A Nicotinic Cation Channel Highly Permeable to Calcium," J. Neurosci. 13: 596–604 (1993).

Sham et al., "Segregration analysis of complex phenotypes: an application to schizophrenia and auditory P300 latency," Psychiat. Genet. 4: 29–38 (1994).

Siegel et al., "Deficits in Sensory Gating in Schizophrenic Patients and Their Relatives, Evidence Obtained With Auditory Evoked Responses," Arch. Gen. Psychiat. 41: 607–612 (1984).

Silverman et al., "Evidence of a Locus for Schizophrenia and Related Disorders on the Short Arm of Chromosome 5 in a Large Pedigree," Am. J. Med. Genet. 67: 162–171 (1996).

Sirota et al., "Schizophrenia and Marfan Syndrome," Br. J. Psychiat. 157: 433–436 (1990).

Spitzer et al., "Research Diagnostic Criteria, Rationale and Reliability," Arch. Gen. Psychiat. 35: 773–782 (1978).

Stratford–Perricaudet et al., "Widespread Long–term Gene Transfer to Mouse Skeletal Muscles and Heart," J. Clin. Invest. 90: 626–630 (1992).

Tsuang et al., "Long–term Outcome of Major Psychoses I. Schizophrenia and Affective Disorders Compared with Psychiatrically Symptom–Free Surgical Conditions," Arch. Gen. Psychiat. 36: 1295–1301 (1979).

Tsuang et al., "Genotypes, Phenotypes, and the Brain, A Search for Connections in Schizophrenia," Brit. J. Psychiat. 163: 299–307 (1993).

Uetsuki et al., "Isolation and Characterization of the Human Chromosomal Gene for Polypeptide Chain Elongation Factor–1α," J. Biol. Chem. 264:5791 [1989].

Ulmer et al., "Heterologous Protection Against Influenza by Injection of DNA Encoding a Viral Protein," Science 259: 1745–1748 (1993).

Vinogradova et al., "Do Semantic Priming Effects Correlate with Sensory Gating in Schizophrenia," Biol. Psychiat. 39: 821–824 (1996).

Vinogradova, in The Hippocampus 2: Neurophysiology and Behavior, Issacson and Pribram (eds.), pp. 3–69, Plenum Press, New York, New York (1975).

von Heijne, "A new method for predicting signal sequence cleavage sites," Nuc. Acids Res. 14: 4683–4690 (1986).

Voss et al., "The role of enhancers in the regulation of cell–type–specific transcriptional control," Trends Biochem. Sci. 11:287–289 [1986].

Wada et al., "Distribution of Alpha2, Alpha3, Alpha4, and Beta2 Neuronal Nicotinic Receptor Subunit mRNAs in the Central Nervous System: A Hybridization Histochemical Study in the Rat," *J. Compar. Neurol.* 284: 314–335 (1989).

Waldo et al., "Codistribution of a Sensory Gating Deficit and Schizophrenia in Multi–affected Families," *Psychiat. Res.* 39: 257–268 (1991).

Waldo et al., "Auditory sensory gating, hipppocampal volume, and catecholamine metabolism in schizophrenics and their siblings," *Schizophr. Res.* 12: 93–106 (1991).

Wang et al., "Evidence for a susceptibility locus for schizophrenia on chromosome 6pter–p22," *Nature Genet.* 10: 41–46 (1995).

Williams et al., "Introduction of foreign genes into tissues of living mice by DNA–coated microprojectiles," *Proc. Natl. Acad. Sci. U.S.A.* 88: 2726–2730 (1991).

Wilson et al., "Habituation of Human Limbic Neuronal Response to Sensory Stimulation," *Exp. Neurol.* 84: 74–97 (1984).

Wilson et al., "Hepatocyte–directed Gene Transfer in Vivo Leads to Transient Improvement of Hypercholesterolemia in Low Density Lipoprotein Receptor–deficient Rabbits," *J. Biol. Chem.* 267: 963–967 (1992).

Wonnacott, "α–Bungarotoxin Binds to Low–Affinity Nicotine Binding Sites in Rat Brain," *J. Neurochem.* 47: 1706–1712 (1986).

Wu and Wallace, "The Ligation Amplification Reaction (LAR)—Amplification of Specific DNA Sequences Using Sequential Rounds of Template–Dependent Ligation," *Genomics* 4:560–569 [1989].

Wu and Wu, "Receptor–mediated Gene Delivery and Expression in Vivo," *J. Biol. Chem.* 263: 14621–14624 (1988).

Wu and Wu, "Receptor–mediated in Vitro Gene Transformation by a Soluble DNA Carrier System," *J. Biol. Chem.* 262: 4429–4432 (1987).

Zhang et al., "Neuronal Acetylcholine Receptors That Bind α–Bungarotoxin with High Affinity Function as Ligand––Gated Ion Channels," *Neuron* 12: 167–177 (1994).

Chini et al., "Molecular Cloning and Chromosomal Localization of the Human α7–Nicotinic Receptor Subunit Gene (CHRNA7)," *Genomics* 19: 379–381 (1994).

Doucette–Stamm et al., "Cloning and Sequence of the Human α7 Nicotinic Acetylcholine Receptor," *Drug Dev. Res.* 30: 252–256 (1993).

Garcia–Guzman et al., "α–Bungarotoxin–sensitive Nicotinic Receptors on Bovine Chromaffin Cells: Molecular Cloning, Functional Expression and Alternative Splicing of the α7 Subunit," *Eur. J. Neuorosci.* 7: 647–655 (1995).

Anand and Lindstrom, "Nucleotide sequence of the human nicotinic acetylcholine receptor β2 subunit gene," *Nuc. Acids Res.* 18: 4272 (1990).

Deneris et al., "Primary Structure and Expression of β2: A Novel Subunit of Neuronal Nicotinic Acetylcholine Receptors," *Neuron* 1: 45–54 (1988).

Fomasari et al., "Structural and Functional Characterization of the Human α3 Nicotinic Subunit Gene Promoter," *Mol. Pharmacol.* 51: 250–261 (1997).

Fomasari et al., "Molecular cloning of human neuronal nicotinic receptor α3–Subunit," *Neurosci. Lett.* 111: 351–356 (1990).

Breese et al., "Comparison of the Regional Expression of Nicotinic Acetylcholine Receptor α7 mRNA and [$^{125}$I]–αbungarotoxin binding in Human Postmortem Brain," *J. Comp. Neurol.* 387: 385–398 (1997).

Leonard et al., "Linkage of a chromosome 15 locus to a neurophysiological deficit in schizophrenia," *Am. J. Human Genet.* 59: A225 (1996).

Leonard et al., "Genomic Structure of the Human α7 Neuronal Nicotinic Acetylcholine Receptor Subunit," *Abstracts, Society for Neuroscience*, 27th Annual Meeting, Oct. 25–30, (1997).

Freedman et al., "Linkage of a neurophysiological deficit in schizophrenia to a chromosome 15 locus," *Proc. Natl. Acad. Sci. U.S.A.* 94: 587–592 (1997).

Logel et al., "Expression of High and Low Affinity Neuronal Nicotinic Receptors in Tissues of Neural Crest Origin," *Abstracts, Society for Neuroscience*, 27th Annual Meeting, Oct. 25–30, (1997).

Breese et al., "Abnormal Regulation of High Affinity Nicotinic Receptor Binding in Schizophrenics," *Abstracts, Society for Neuroscience*, 27th Annual Meeting, Oct. 25–30, (1997).

Gault et al., "Contig construction across the 15q14 schizophrenia linkage region and candidate gene characterization of the partially duplicated α7 nicotinic receptor," *Am. J. Human Genet.* 63: A249 (1998).

Leonard et al., "Additional evidence for a chromosome 15 locus in schizophrenia: Analysis of affected sibpairs from the NMH genetics initiative," *Am. J. Human Genet.* 63: A297 (1998).

Zetterström et al., "Polymorphisms at the Calcitonin/CGRP–α Gene Locus: Investigation of Possible Associations with Neurological or Psychiatric Disease," *Abstracts, Society for Neuroscience*, 28th Annual Meeting, Nov. 7–12, (1998).

Drebing et al., "Expression of the Human α7 Neuronal Nicotinic Acetylcholine Receptor and a Partial Gene Duplication," *Abstracts, Society for Neuroscience*, 28th Annual Meeting, Nov. 7–12, (1998).

Leonard et al., "Genomic Organization and Partial Duplication of the Human α7 Neuronal Nicotinic Acetylcholine Receptor Subunit Gene," *Abstracts, Society for Neuroscience*, 28th Annual Meeting, Nov. 7–12, (1998).

Dudek et al., "Expression in Human Brain of Novel Exons Associated with a Partial Duplication of the α7 Neuronal Nicotinic Receptor," *Abstracts, Society for Neuroscience*, 28th Annual Meeting, Nov. 7–12, (1998).

Breese et al., "Abnormal Regulation of the High Affinity Nicotinic Receptors in Schizophrenia," *Abstracts, Society for Neuroscience*, 28th Annual Meeting, Nov. 7–12 (1998).

Lee et al., "The Effect of Nicotine and Haloperidol on High Affinity Nicotinic Receptors and Dopamine D2 Receptors in the Rat Brain," *Abstracts, Society for Neuroscience*, 28th Annual Meeting, Nov. 7–12 (1998).

Adler et al., "Schizophrenia, Sensory Gating, and Nicotinic Receptors," *Schizophrenia Bulletin* 24: 189–202 (1998).

Leonard et al., "Further Investigation of a Chromosome 15 Locus in Schizophrenia: Analysis of Affected Sibpairs From the NIMH Genetics Initiative," *Am. J. Med. Genet.* 81: 308–312 (1998).

Gault et al., Genomic Organization and Partial Duplication of the Human α7 Neuronal Nicotinic Acetylcholine Receptor Gene (CHRNA7), *Genomics* 52: 173–185 (1998).

* cited by examiner

Exon-Intron Boundary Sequences of the Human alpha-7 nAChR Subunit Gene

| Exon Number | Exon length (bp) | cDNA position | splice acceptor | flanking exon sequence | splice donor | Intron number | Intron Size approximate (Kb) |
|---|---|---|---|---|---|---|---|
| 1 | 55 | 1-55 | | ...CTG CAC G<br>L H | GTAAAGCCAC | 1 | 0.3 |
| 2 | 140 | 56-195 | TCTCCTTAAG | TG TCC......GAC GTG<br>V S D V | GTGAGTCCCG | 2 | Unknown |
| 3 | 45 | 196-240 | TTTTTTGAAG | GAT GAG......CAA ATG<br>D E Q M | GTAAGTTAAG | 3 | 9.0 |
| 4 | 110 | 241-350 | TGTGTGTCAG | TCT TGG......AAC AG<br>S W N S | GTAAGCATAT | 4 | Unknown |
| 5 | 80 | 351-430 | CTGTTTCTAG T GCT GAT......CCT CCA G<br>A D P P | | GTAAGCTGCA | 5 | 4.0 |
| 6 | 168 | 431-598 | ACCCACACAG | GC ATA......CTA GTG G<br>G I L V | GTAAGCCATG | 6 | 1.0 |
| 7 | 195 | 599-793 | CCCTATGGAG | GA ATC......TCC CTG G<br>G I S L | GTAAGCGCCC | 7 | 1.0 |
| 8 | 87 | 794-880 | TATGTTTTAG | GG ATA......TTG ATA G<br>G I L I | GTAAGGCAAG | 8 | 3.5 |
| 9 | 110 | 881-990 | CTCTCCACAG | CC CAG......AAG TGG<br>A Q K W | GTACGTTCCT | 9 | 5.0 |
| 10 | 519 | 991-1509 | GTCTCCCCAG | ACC AGA...<br>T R | | | |

FIG. 1

Sequence Variants Identified in Full-Length and Duplicated Genomic Clones

| DNA | EXONS CONT. | EXON 6 +/− 497-498 | EXON 7 654 | | EXON 7 690 | | EXON 10 1269 | | EXON 10 1335 | | L76630 |
|---|---|---|---|---|---|---|---|---|---|---|---|
| CHR15 HYBRID | 5-10 | | | | | | | | C/C | | 6GT |
| | 1-10 | | C/T | | G/A | | C/C | | | | 8GT |
| YAC | | | | | | | | | | | |
| D-948a10 | 5-10 | −TG | | T | | A | | C | | | 6GT |
| D-853b12 | 6-10 | −TG | | T | | A | | C | | | 6GT |
| D/F 969b11 | 5-10 | +TG | C/T | | G/A | | | C/T | C/C | | 6GT |
| | 1-10 | −TG | | | | | | | | | 8GT |
| F-134h10 | 1-10 | +TG | C | | G | | C | | C | | 8GT |
| F-776a12 | 1-10 | +TG | C | | G | | C | | C | | 8GT |
| F-791e6 | 1-10 | +TG | C | | G | | C | | C | | 8GT |
| F-811b6 | 1-10 | +TG | C | | G | | C | | C | | 8GT |
| F-953g6 | 1-10 | +TG | C | | G | | C | | C | | 8GT |
| F-859c11 | 1-10 | +TG | C | | G | | C | | C | | 8GT |
| F-810f11 | 1-10 | +TG | C | | G | | C | | C | | 8GT |
| F-801e1 | 1-10 | +TG | C | | G | | C | | C | | 8GT |
| BAC | | | | | | | | | | | |
| F-467o18 | 1-10 | +TG | C | | G | | | | | T | 8GT |

| DNA | Control # | EXON 6 +/− 497-498 | | | EXON 7 654 | | | EXON 7 690 | | | EXON 10 1269 | | | EXON 10 1335 | | |
|---|---|---|---|---|---|---|---|---|---|---|---|---|---|---|---|---|
| | | +/+ | +/− | −/− | C/C | C/T | T/T | G/G | G/A | A/A | C/C | C/T | T/T | C/C | C/T | T/T |
| Control Genomic DNA | 43 | 10 | 33 | 0 | 5 | 38 | 0 | 0 | 43 | 0 | 6 | 36 | 1 | 24 | 19 | 0 |

FIG. 2

Expression Analysis of Sequence Variants

| Subj | Bases 497-498 | | | Base 654 | | | Base 690 | | | Base 933 | | | Base 1296 | | | Base 1335 | | |
|---|---|---|---|---|---|---|---|---|---|---|---|---|---|---|---|---|---|---|
| | DNA | 1-10 cDNA | 5-10 cDNA | DNA | 1-10 cDNA | 5-10 cDNA | DNA | 1-10 cDNA | 5-10 cDNA | DNA | 1-10 cDNA | 5-10 cDNA | DNA | 1-10 cDNA | 5-10 cDNA | DNA | 1-10 cDNA | 5-10 cDNA |
| SL061 | +/- | + | +/- | CT | C | CT | GA | G | GA | G | G | G | CT | CT | CT | C | C | C |
| SL084 | + | + | + | C | C | C | GA | G | GA | G | G | G | CT | C | CT | C | C | C |
| SL111 | +/- | + | +/- | CT | C | CT | GA | G | GA | G | G | G | CT | CT | CT | CT | CT | CT |
| SL097 | + | + | + | CT | C | CT | GA | G | GA | G | G | G | CT | C | CT | C | C | C |
| SL089 | + | + | + | C | C | C | GA | GA | GA | GA | GA | GA | CT | CT | CT | C | C | C |
| SHSY | +/- | + | +/- | CT | C | CT | GA | GA | GA | GA | GA | GA | C | C | C | C | C | C |

FIG. 3

```
-392  agaacgcaag ggagaggtag agcctggcct tgggcag ccc ctgg ctggc cagaggcgcg aggccgagag
                                                    AP-2
-322  cccgctcggt ggagactggg ggtggaggtg cccgagcgt accagcgcc gggagtacct cccgctcaca
-252  cctcgggctg cagttccctg ggtggccgcc gagacgctgg cccgggctgg agggatggcg gggcggggac
-182  ggggcgggg gcggggct cg tca gtggag aggcgcgcgg ggcg ggcgg ggcgccggcg cgcgcccggc
                      CREB                              Sp1
-112  tccttaaagg cgcgcgagcc gagcggcgag gtgcctctgt ggccgcaggc gcaggcccgg gcgacagccg
-42   agacgtggag cgcgccggct cgctgcagct ccgggactca acATGCGCTG CTCGCCGGGA GGCGTCTGGC
                                                       Met
+29   TGGCGCTGGC CGCGTCGCTC CTGCACGgta aagccac
```

```
EXON D      1
297bp       CAGGCCGCCA  CATAGCTCCC  GCCAAGTCCT  CGGTGCCCCT  TGCCATTTTC  CAGCCGCGTC  CCACGAGGGT
            CACGGCGGCG  GGAGAGGTG   GAGCCGGAG   AGCTCGGCCG  GGGCCCCGC   CTGGTGGCCG  CGGCCATGAC
            AGCGGCTCGG  GACTGGCTCC  TTTTCCGCGC  CCCTCCCGCC  GGAGGTGAGG  GGAAGATGTC  CATGTCAGGG
            TTCAAGGCCA  AACCGAAGTT  ACTGGCCTCT  ATCTTCCAGG                          
            CCCACCGCAA  CATTAAGgtg  agtcgcc...                                      
                        297         298

EXON C       ....ctc    atttcagATT  ACAAGTGGAC  ACCTGAGTCA  GCAGGACCTG  GAATCCCAGA  TGAGAGAGCT
125bp       TATCTACACG  ACTCAGATCT  TGTTGTCACC  CCCATTATTG  ACAATCCAAA  GGTGCAGAAA  GCACTCTGAC
            AAgtgagttg  ta......                                                   
            422         423

EXON B      ..ttaaccac  agATAATGAA  ACAACCACCA  TCGGTTAAAT  TTGATGCAAA  AATATTGCAT  CTACCAGCAT
64bp        TTTCAGgtag  gatcat.....                                                 
            486         487

EXON A      ......ttta  ttctagTTCC  AATTGCTAAT  CCAGCATTTG  TGGATAGCTG  CAAACTGCGA  TATgtaagta
47bp        aca.......                                                             533
            534

EXON 5       ...ctgtttc tagTGCTGAT  GAGCGCTTTG  ACGCCACATT  CCACACTAAC  GTGTTGGTGA  ATTCTTCTGG
80bp                    GCATTGCCAG  TACCTGCCTC  CAGgtaagctgca.....                   
                        614                    613

EXON 6       .....acccaca  cagGCATATT CAAGAGTTCC TGCTACATCG
27bp                                            640
```

FIG. 6

```
  1 agaacgcaag ggagaggtag agcctggcct tgggcagccc ctggcctggc cagaggcgcg
 61 aggccgagag cccgctcggt ggagactggg ggtggaggtg cccggagcgt acccagcgcc
121 gggagtacct cccgctcaca cctcgggctg cagttccctg ggtggccgcc gagacgctgg
181 cccgggctgg agggatggcg gggcggggac ggggcgggg gcggggctcg tcacgtggag
241 aggcgcgcgg gggcgggcgg ggcggggcg cgcgcccggc tccttaaagg cgcgcgagcc
301 gagcggcgag gtgcctctgt ggccgcaggc gcaggcccgg gcgacagccg agacgtggag
361 cgcgccggct cgctgcagct ccgggactca ac
```

FIG. 8

```
  1 caggccgcca catagctccc gccaagtcct cggtgcccct tgccattttc cagccgcgct
 61 cccacgaggg tcacggcggc ggggagaggt ggagccgcga gagctcggcc ggggccccg
121 cctggtggcc gcggccatga cagcggctcg ggactggctc cttttccgcg ccctcccgc
181 cggaggtgag gggaagatgt ccatgtcagg gttcaaggcc aaaccgaagt tactggcctc
241 tatcttccag gagaaccagg agccacagcc gcggctcacg ccccaccgca acattaagat
301 tacaagtgga cacctgagtc agcaggacct ggaatccag atgagagagc ttatctacac
361 gactcagatc ttgttgtcac cccattatt gacaatccaa aggtgcagaa agcactctga
421 caaataatga aacaaccacc atcggttaaa tttgatgcaa aaatattgca tctaccagca
481 ttttcagttc caattgctaa tccagcattt gtggatagct gcaaactgcg atattgctga
541 tgagcgcttt gacgccacat tccacactaa cgtgttggtg aattcttctg ggcattgcca
601 gtacctgcct ccaggcatat tcaagagttc ctgctacatc g
```

FIG. 9

```
  1 agccctttcc caggcggtag cgggggcagt ggtgctgttg ccctttttaaa ctgcggcttg
 61 acgggagccg cgcctcctgt cggtggagtc ggttataaag ggagcagccc cgcaggccgc
121 cacatagctc ccgccaagtc ctcggtgccc cttgccattt tccagccgcg ctcccacgag
181 ggtcacggcg gcggggagag gtggagccgc gagagctcgg ccggggggccc cgcctggtgg
241 ccgcggccat gacagcggct cgggactggc tccttttccg cgccctcccc gccggaggtg
301 aggggaagat gtccatgtca gggttcaagg ccaaaccgaa gttactggcc tctatcttcc
361 aggagaacca ggagccacag ccgcggctca cgcccaccg caacattaag attacaagtg
421 gacacctgag tcagcaggac ctggaatccc agatgagaga gcttatctac acgactcaga
481 tcttgttgtc accccatta ttgacaatcc aaaggtgcag aaagcactct gacaattcca
541 attgctaatc cagcatttgt ggatagctgc aaactgcgat attgctgatg agcgctttga
601 cgccacattc cacactaacg tgttggtgaa ttcttctggg cattgccagt acctgcctcc
661 aggcatattc aagagttcct gctacatcg
```

FIG. 10

```
SEQUENCE LISTING (1) GENERAL INFORMATION:

(iii) NUMBER OF SEQUENCES: 121

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:1:

TCCTGATGTC GGCTCCCAAC T                                              21

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:2:

GGTACGGATG TGCCAAGGAT A                                              21

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
```

(D) TOPOLOGY: linear (ii) MOLECULE TYPE: other nucleic acid
          (A) DESCRIPTION: /desc = "DNA"

(xi) SEQUENCE DESCRIPTION: SEQ ID NO:3:

TTTGGGGGTG CTAATCCAGG A                                              21

(2) INFORMATION FOR SEQ ID NO:4:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:4:

TTGTTTTCCT TCCACCAGTC A                                              21

(2) INFORMATION FOR SEQ ID NO:5:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:5:

CTCGCTGCAG CTCCGGGACT CA                                             22

(2) INFORMATION FOR SEQ ID NO:6:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:6:

GGAGGCTCAG GGAGAAGTAG                                                20

(2) INFORMATION FOR SEQ ID NO:7:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:7:

CTCCAGGATC TTGGCCAAGT C                                              21

(2) INFORMATION FOR SEQ ID NO:8:

(i) SEQUENCE CHARACTERISTICS:
          (A) LENGTH: 21 base pairs
          (B) TYPE: nucleic acid

```
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

AGATGCCCAA GTGGACCAGA G                                              21

(2) INFORMATION FOR SEQ ID NO:9:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:9:

AGATGCCCAA GTGGACCAGA GTCATCCTTC TGAACTGGTG CGCGTGGTTC CTGCGAATGA    60

AGAGGCCCGG GGAGGACAAG GTGCGCCCGG CCTGCCAGCA CAAGCAGCGG CGCTGCAGCC   120

TGGCCAGTGT GGAGATGAGC GCCGTGGGCC CGCCGCCCGC CAGCAACGGG AACCTGCTGT   180

ACATCGGCTT CCGCGGCCTG GACGGCGTGC ACTGTGTCCC GACCCCCGAC TCTGGGGTAG   240

TGTGTGGCCG CATGGCCTGC TCCCCCACGC ACGATGAGCA CCTCCTGCAC GGCGGGCAAC   300

CCCCCGAGGG GGACCCGGAC TTGGCCAAGA TCCTGGA                            337

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

CACACACACA CACACACACA CACACACACA CA                                  32

(2) INFORMATION FOR SEQ ID NO:11:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

CACACACACA TCACACACAC ACACACACAC ACACATACAC ACACACCA CACA             54

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"
```

(xi) SEQUENCE DESCRIPTION: SEQ ID NO:12:

GATCTTTGGT AGAAGC                                                           16

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:13:

ACCACCACTA CCATACAGAC                                                       20

(2) INFORMATION FOR SEQ ID NO:14:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:14:

CAAAGAACGC AAGGGAGAGG T                                                     21

(2) INFORMATION FOR SEQ ID NO:15:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:15:

CGGCTCGCGC GCCTTTAAGG A                                                     21

(2) INFORMATION FOR SEQ ID NO:16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:16:

GGGCTCGTCA CGTGGAAAAG C                                                     21

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid (A) DESCRIPTION: /desc = "DNA"

(xi) SEQUENCE DESCRIPTION: SEQ ID NO:17:

GGATCCCACG GAGGAGTGGA G                                           21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

CCTGCCCGGG TCTTCTCTCC T                                           21

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:19:

AACTAGAGTG CCCCAGCCGA GCT                                         23

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:20:

AACAACGCTC TCGACAGTCA GATC                                        24

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:21:

AAGATCTTGC AGCCCATGGG AG                                          22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear

```
    (ii) MOLECULE TYPE: other nucleic acid
         (A) DESCRIPTION: /desc = "DNA"

(xi) SEQUENCE DESCRIPTION: SEQ ID NO:22:

GGAATTCTCT TTGGTTTTGC AC                                              22

(2) INFORMATION FOR SEQ ID NO:23:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:23:

ACATATCCAG CATCTCTGTG A                                               21

(2) INFORMATION FOR SEQ ID NO:24:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:24:

TCATGCAGTC CTTTTCCTGT TTC                                             23

(2) INFORMATION FOR SEQ ID NO:25:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:25:

CTCGCTTCAG TTTTCTAACA TGG                                             23

(2) INFORMATION FOR SEQ ID NO:26:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:26:

GGAACTGCTG TGTATTTTCA GC                                              22

(2) INFORMATION FOR SEQ ID NO:27:

(i) SEQUENCE CHARACTERISTICS:
         (A) LENGTH: 22 base pairs
         (B) TYPE: nucleic acid
         (C) STRANDEDNESS: single
         (D) TOPOLOGY: linear
```

(ii) MOLECULE TYPE: other nucleic acid
            (A) DESCRIPTION: /desc = "DNA"

(xi) SEQUENCE DESCRIPTION: SEQ ID NO:27:

TTAAAGCTTG CCCAGGAATA GG                                              22

(2) INFORMATION FOR SEQ ID NO:28:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:28:

GCTTGTGTGT GGTATACACA TTG                                             23

(2) INFORMATION FOR SEQ ID NO:29:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:29:

TCCAGAGCTG ATCTCAGCAG AAG                                             23

(2) INFORMATION FOR SEQ ID NO:30:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:30:

GCCCCTCGTT AGACAGAATT GAG                                             23

(2) INFORMATION FOR SEQ ID NO:31:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:31:

CTGGGCACAC TCTAACCCTA ACC                                             23

(2) INFORMATION FOR SEQ ID NO:32:

(i) SEQUENCE CHARACTERISTICS:
            (A) LENGTH: 22 base pairs
            (B) TYPE: nucleic acid
            (C) STRANDEDNESS: single

```
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:32:

TGTGACGTGC AGTGCCACAG GA                                        22

(2) INFORMATION FOR SEQ ID NO:33:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:33:

AAAACCCTAG GAGGAGCCTC CTT                                       23

(2) INFORMATION FOR SEQ ID NO:34:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:34:

GATCAGCCCG TTTCCGCCTC A                                         21

(2) INFORMATION FOR SEQ ID NO:35:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:35:

GGTACGGATG TGCCAAGGAT A                                         21

(2) INFORMATION FOR SEQ ID NO:36:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "DNA"

(xi) SEQUENCE DESCRIPTION: SEQ ID NO:36:

GGACTCTGCT TTTGATAAAT ATGTATG                                   27

(2) INFORMATION FOR SEQ ID NO:37:

(i) SEQUENCE CHARACTERISTICS:
          (A) LENGTH: 24 base pairs
          (B) TYPE: nucleic acid
```

```
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:37:

TTGCTGTCAC TTTCTGTGTT TCAT                                          24

(2) INFORMATION FOR SEQ ID NO:38:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:38:

GACAATCCAA AGGTGCAGAA AGC                                           23

(2) INFORMATION FOR SEQ ID NO:39:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:39:

TTCGTATCTG TATACAGACA GTC                                           23

(2) INFORMATION FOR SEQ ID NO:40:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:40:

CCTCAGCATC ATATTAGTTC AGTG                                          24

(2) INFORMATION FOR SEQ ID NO:41:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:41:

GCGGACAAGA GAAACAGGAA AG                                            22

(2) INFORMATION FOR SEQ ID NO:42:

(i) SEQUENCE CHARACTERISTICS:
            (A) LENGTH: 21 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

GGCAGTGGTG CTGTTGCCCT T                                        21

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:43:

TTTCTCCTGG GACTCTGGGC AC                                       22

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

TGACGCCACA TTCCACACTA A                                        21

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:45:

TTGTTTTCCT TCCACCAGTC A                                        21

(2) INFORMATION FOR SEQ ID NO:46:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:46:

CCAAGTTTTA ACCACCAACA TTTGG                                    25

(2) INFORMATION FOR SEQ ID NO:47:

(i) SEQUENCE CHARACTERISTICS:

```
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:47:

TCCCCGCGGA AGAATGTCTG GTTTCCAAAT CTG                                33

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:48:

CTCCAGGATC TTGGCCAAGT C                                            21

(2) INFORMATION FOR SEQ ID NO:49:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:49:

CAUCAUCAUC AUCCAGCGTA CATCGATGTA GCAGGAACTC TTGAATAT               48

(2) INFORMATION FOR SEQ ID NO:50:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(ix) FEATURE:
        (A) NAME/KEY: -
        (B) LOCATION: 36..37
        (D) OTHER INFORMATION: /note= "The residue at this
            position is Inosine."

(ix) FEATURE:
        (A) NAME/KEY: -
        (B) LOCATION: 40..41
        (D) OTHER INFORMATION: /note= "The residue at this
            position is Inosine."

(ix) FEATURE:
        (A) NAME/KEY: -
        (B) LOCATION: 45..46
        (D) OTHER INFORMATION: /note= "The residue at this
            position is Inosine."

(xi) SEQUENCE DESCRIPTION: SEQ ID NO:50:

CUACUACUAC UAGGCCACGC GTCGACTAGT ACGGGNNGGN NGGGNNG                47
```

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:51:

CGCTGCAGCT CCGGGACTCA ACATG                                              25

(2) INFORMATION FOR SEQ ID NO:52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:52:

TGCCCATCTG TGAGTTTTCC ACATG                                              25

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:53:

TGACGCCACA TTCCACACTA A                                                  21

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:54:

CCCCAAATCT CGCCAAGC                                                      18

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:55:

CTCGGTGCCC CTTGCCATTT                                                    20

(2) INFORMATION FOR SEQ ID NO:56:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:56:

CCTTGCCCAT CTGTGAGTTT TCCAC     25

(2) INFORMATION FOR SEQ ID NO:57:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:57:

CCCAGTACTT CGCCAGCACC ATGAT     25

(2) INFORMATION FOR SEQ ID NO:58:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:58:

CCCCGTCGGG GTCGTGGTGG TGGTA     25

(2) INFORMATION FOR SEQ ID NO:59:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:59:

TCCCCGGCAA GAGGAGTGAA AGGTT     25

(2) INFORMATION FOR SEQ ID NO:60:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:60:

ACACCAGCAG GGCGAGGGCG GAGAT     25

(2) INFORMATION FOR SEQ ID NO:61:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:61:

GACCAGAGTC ATCCTTCTGA ACTGG                                        25

(2) INFORMATION FOR SEQ ID NO:62:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:62:

TTTCAGGTAG ACCTTCATGC AGACA                                        25

(2) INFORMATION FOR SEQ ID NO:63:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:63:

CGATGTACGC TGGTTTCCCT TTGAT                                        25

(2) INFORMATION FOR SEQ ID NO:64:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:64:

TTCCCACTAG GTCCCATTCT CCATT                                        25

(2) INFORMATION FOR SEQ ID NO:65:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:65:

```
CGCTGCAGCT CCGGGACTCA ACATG                                              25
```

(2) INFORMATION FOR SEQ ID NO:66:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:66:

```
TGCCCATCTG TGAGTTTTCC ACATG                                              25
```

(2) INFORMATION FOR SEQ ID NO:67:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:67:

```
TGACGCCACA TTCCACACTA A                                                  21
```

(2) INFORMATION FOR SEQ ID NO:68:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:68:

```
CCCCAAATCT CGCCAAGC                                                      18
```

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:69:

```
CTCGGTGCCC CTTGCCATTT                                                    20
```

(2) INFORMATION FOR SEQ ID NO:70:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:70:

CCTTGCCCAT CTGTGAGTTT TCCAC                                            25

(2) INFORMATION FOR SEQ ID NO:71:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:71:

TGTAAAACGA CGGCCAGT                                                    18

(2) INFORMATION FOR SEQ ID NO:72:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:72:

CAGGAAACAG CTATGACC                                                    18

(2) INFORMATION FOR SEQ ID NO:73:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:73:

AAGGAGCTGG TCAAGAACTA CAATC                                            25

(2) INFORMATION FOR SEQ ID NO:74:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:74:

CCGGAATCTG CAGGAAGCAG GAACA                                            25

(2) INFORMATION FOR SEQ ID NO:75:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:75:

CCAGGCGTGG TTACGCAAAG TCTTTG                                    26

(2) INFORMATION FOR SEQ ID NO:76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:76:

GATGTGCAGC ACTGCAAACA A                                         21

(2) INFORMATION FOR SEQ ID NO:77:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:77:

TTAAAGCTTG CCCAGGAATA GG                                        22

(2) INFORMATION FOR SEQ ID NO:78:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:78:

GGAACTGCTG TGTATTTTCA GC                                        22

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:79:

AAGACCAGGA CCCAAACTTG T                                         21

(2) INFORMATION FOR SEQ ID NO:80:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:80:

GCTTGTGTGT GGTATACACA TTG                                               23

(2) INFORMATION FOR SEQ ID NO:81:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:81:

GTAGAGTGTC CTGCGGC                                                      17

(2) INFORMATION FOR SEQ ID NO:82:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:82:

GGTCCGCTAC ATTGCCAA                                                     18

(2) INFORMATION FOR SEQ ID NO:83:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:83:

TGATGGTGAA GACCGAGAAG G                                                 21

(2) INFORMATION FOR SEQ ID NO:84:

(i) SEQUENCE CHARACTERISTICS:
         (A) LENGTH: 55 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:84:

NNNNNNNNNN NNNNNNNNNN NNNNNNNNNN NNNNNNNNNN NNNNNNNNCT GCACG            55

(2) INFORMATION FOR SEQ ID NO:85:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: other nucleic acid (A) DESCRIPTION: /desc = "DNA"

(xi) SEQUENCE DESCRIPTION: SEQ ID NO:85:

TCTCCTTAAG                                                              10

(2) INFORMATION FOR SEQ ID NO:86:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:86:

TTTTTTGAAG                                                              10

(2) INFORMATION FOR SEQ ID NO:87:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:87:

TGTGTGTCAG                                                              10

(2) INFORMATION FOR SEQ ID NO:88:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:88:

CTGTTTCTAG T                                                            11

(2) INFORMATION FOR SEQ ID NO:89:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:89:

ACCCACACAG                                                              10

(2) INFORMATION FOR SEQ ID NO:90:

(i) SEQUENCE CHARACTERISTICS:
        (A) LENGTH: 10 base pairs
        (B) TYPE: nucleic acid
        (C) STRANDEDNESS: single
        (D) TOPOLOGY: linear

```
       (ii) MOLECULE TYPE: other nucleic acid
            (A) DESCRIPTION: /desc = "DNA"

(xi) SEQUENCE DESCRIPTION: SEQ ID NO:90:

CCCTATGGAG                                                             10

(2) INFORMATION FOR SEQ ID NO:91:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:91:

TATGTTTTAG                                                             10

(2) INFORMATION FOR SEQ ID NO:92:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:92:

CTCTCCACAG                                                             10

(2) INFORMATION FOR SEQ ID NO:93:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:93:

GTCTCCCCAG                                                             10

(2) INFORMATION FOR SEQ ID NO:94:

(i) SEQUENCE CHARACTERISTICS:
            (A) LENGTH: 457 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:94:

AGAACGCAAG GGAGAGGTAG AGCCTGGCCT TGGGCAGCCC CTGGCCTGGC CAGAGGCGCG       60

AGGCCGAGAG CCCGCTCGGT GGAGACTGGG GGTGGAGGTG CCCGGAGCGT ACCCAGCGCC      120

GGGAGTACCT CCCGCTCACA CCTCGGGCTG CAGTTCCCTG GGTGGCCGCC GAGACGCTGG      180

CCCGGGCTGG AGGGATGGCG GGGCGGGGAC GGGGGCGGGG GCGGGGCTCG TCACGTGGAG      240

AGGCGCGCGG GGGCGGGCGG GGCGGGGGCG CGCGCCCGGC TCCTTAAAGG CGCGCGAGCC      300
```

```
GAGCGGCGAG GTGCCTCTGT GGCCGCAGGC GCAGGCCCGG GCGACAGCCG AGACGTGGAG      360

CGCGCCGGCT CGCTGCAGCT CCGGGACTCA ACATGCGCTG CTCGCCGGGA GGCGTCTGGC      420

TGGCGCTGGC CGCGTCGCTC CTGCACGGTA AAGCCAC                               457
```

(2) INFORMATION FOR SEQ ID NO:95:

(i) SEQUENCE CHARACTERISTICS:
        (A) LENGTH: 308 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:95:

```
CAGGCCGCCA CATAGCTCCC GCCAAGTCCT CGGTGCCCCT TGCCATTTTC CAGCCGCGTC       60

CCACGAGGGT CACGGCGGCG GGGAGAGGTG GAGCCGCGAG AGCTCGGCCG GGGGCCCCGC      120

CTGGTGGCCG CGGCCATGAC AGCGGCTCGG GACTGGCTCC TTTTCCGCGC CCCTCCCGCC      180

GGAGGTGAGG GGAAGATGTC CATGTCAGGG TTCAAGGCCA AACCGAAGTT ACTGGCCCTC      240

TATCTTCCAG GAGAACCAGG AGCCACAGCC GCGGCTCACG CCCCACCGCA ACATTAAGGT      300

GAGTCGCC                                                              308
```

(2) INFORMATION FOR SEQ ID NO:96:

(i) SEQUENCE CHARACTERISTICS:
        (A) LENGTH: 145 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:96:

```
CTCATTTCAG ATTACAAGTG GACACCTGAG TCAGCAGGAC CTGGAATCCC AGATGAGAGA       60

GCTTATCTAC ACGACTCAGA TCTTGTTGTC ACCCCCATTA TTGACAATCC AAAGGTGCAG      120

AAAGCACTCT GACAAGTGAG TTGTA                                           145
```

(2) INFORMATION FOR SEQ ID NO:97:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:97:

```
TTAACCACAG ATAATGAAAC AACCACCATC GGTTAAATTT GATGCAAAAA TATTGCATCT       60

ACCAGCATTT TCAGGTAGGA TCAT                                             84
```

(2) INFORMATION FOR SEQ ID NO:98:

(i) SEQUENCE CHARACTERISTICS:
        (A) LENGTH: 67 base pairs
        (B) TYPE: nucleic acid
        (C) STRANDEDNESS: single
        (D) TOPOLOGY: linear -continued (ii) MOLECULE TYPE: other nucleic acid
    (A) DESCRIPTION: /desc = "DNA"

(xi) SEQUENCE DESCRIPTION: SEQ ID NO:98:

TTTATTCTAG TTCCAATTGC TAATCCAGCA TTTGTGGATA GCTGCAAACT GCGATATGTA    60

AGTAACA    67

(2) INFORMATION FOR SEQ ID NO:99:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:99:

CTGTTTCTAG TGCTGATGAG CGCTTTGACG CCACATTCCA CACTAACGTG TTGGTGAATT    60

CTTCTGGGCA TTGCCAGTAC CTGCCTCCAG GTAAGCTGCA    100

(2) INFORMATION FOR SEQ ID NO:100:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:100:

ACCCACACAG GCATATTCAA GAGTTCCTGC TACATCG    37

(2) INFORMATION FOR SEQ ID NO:101:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:101:

AGAACGCAAG GGAGAGGTAG AGCCTGGCCT TGGGCAGCCC CTGGCCTGGC CAGAGGCGCG    60

AGGCCGAGAG CCCGCTCGGT GGAGACTGGG GGTGGAGGTG CCCGGAGCGT ACCCAGCGCC    120

GGGAGTACCT CCCGCTCACA CCTCGGGCTG CAGTTCCCTG GGTGGCCGCC GAGACGCTGG    180

CCCGGGCTGG AGGGATGGCG GGGCGGGGAC GGGGGCGGGG GCGGGGCTCG TCACGTGGAG    240

AGGCGCGCGG GGGCGGGCGG GGCGGGGGCG CGCGCCCGGC TCCTTAAAGG CGCGCGAGCC    300

GAGCGGCGAG GTGCCTCTGT GGCCGCAGGC GCAGGCCCGG GCGACAGCCG AGACGTGGAG    360

CGCGCCGGCT CGCTGCAGCT CCGGGACTCA AC    392

(2) INFORMATION FOR SEQ ID NO:102:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "DNA"

(xi) SEQUENCE DESCRIPTION: SEQ ID NO:102:

| | | | | | |
|---|---|---|---|---|---|
| AGCCCTTTCC | CAGGCGGTAG | CGGGGGCAGT | GGTGCTGTTG | CCCTTTTAAA | CTGCGGCTTG | 60 |
| ACGGGAGCCG | CGCCTCCTGT | CGGTGGAGTC | GGTTATAAAG | GGAGCAGCCC | CGCAGGCCGC | 120 |
| CACATAGCTC | CCGCCAAGTC | CTCGGTGCCC | CTTGCCATTT | TCCAGCCGCG | CTCCCACGAG | 180 |
| GGTCACGGCG | GCGGGGAGAG | GTGGAGCCGC | GAGAGCTCGG | CCGGGGGCCC | CGCCTGGTGG | 240 |
| CCGCGGCCAT | GACAGCGGCT | CGGGACTGGC | TCCTTTTCCG | CGCCCCTCCC | GCCGGAGGTG | 300 |
| AGGGGAAGAT | GTCCATGTCA | GGGTTCAAGG | CCAAACCGAA | GTTACTGCC  | TCTATCTTCC | 360 |
| AGGAGAACCA | GGAGCCACAG | CCGCGGCTCA | CGCCCCACCG | CAACATTAAG | ATTACAAGTG | 420 |
| GACACCTGAG | TCAGCAGGAC | CTGGAATCCC | AGATGAGAGA | GCTTATCTAC | ACGACTCAGA | 480 |
| TCTTGTTGTC | ACCCCCATTA | TTGACAATCC | AAAGGTGCAG | AAAGCACTCT | GACAATTCCA | 540 |
| ATTGCTAATC | CAGCATTTGT | GGATAGCTGC | AAACTGCGAT | ATTGCTGATG | AGCGCTTTGA | 600 |
| CGCCACATTC | CACACTAACG | TGTTGGTGAA | TTCTTCTGGG | CATTGCCAGT | ACCTGCCTCC | 660 |
| AGGCATATTC | AAGAGTTCCT | GCTACATCG | | | | 689 |

(2) INFORMATION FOR SEQ ID NO:103:

(i) SEQUENCE CHARACTERISTICS:
        (A) LENGTH: 641 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:103:

| | | | | | |
|---|---|---|---|---|---|
| CAGGCCGCCA | CATAGCTCCC | GCCAAGTCCT | CGGTGCCCCT | TGCCATTTTC | CAGCCGCGCT | 60 |
| CCCACGAGGG | TCACGGCGGC | GGGGAGAGGT | GGAGCCGCGA | GAGCTCGGCC | GGGGCCCCG  | 120 |
| CCTGGTGGCC | GCGGCCATGA | CAGCGGCTCG | GGACTGGCTC | CTTTTCCGCG | CCCCTCCCGC | 180 |
| CGGAGGTGAG | GGGAAGATGT | CCATGTCAGG | GTTCAAGGCC | AAACCGAAGT | TACTGGCCTC | 240 |
| TATCTTCCAG | GAGAACCAGG | AGCCACAGCC | GCGGCTCACG | CCCCACCGCA | ACATTAAGAT | 300 |
| TACAAGTGGA | CACCTGAGTC | AGCAGGACCT | GGAATCCCAG | ATGAGAGAGC | TTATCTACAC | 360 |
| GACTCAGATC | TTGTTGTCAC | CCCATTATT  | GACAATCCAA | AGGTGCAGAA | AGCACTCTGA | 420 |
| CAAATAATGA | ACAACCACC  | ATCGGTTAAA | TTTGATGCAA | AAATATTGCA | TCTACCAGCA | 480 |
| TTTTCAGTTC | CAATTGCTAA | TCCAGCATTT | GTGGATAGCT | GCAAACTGCG | ATATTGCTGA | 540 |
| TGAGCGCTTT | GACGCCACAT | TCCACACTAA | CGTGTTGGTG | AATTCTTCTG | GCATTGCCA  | 600 |
| GTACCTGCCT | CCAGGCATAT | TCAAGAGTTC | CTGCTACATC | G | | 641 |

(2) INFORMATION FOR SEQ ID NO:104:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:104:

```
GTAAAGCCAC                                                          10

(2) INFORMATION FOR SEQ ID NO:105:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:105:

TGTCCNNNNN NNNNNNNNNN NNNNNNNNNN NNNNNNNNNN NNNNNNNNNN NNNNNNNNNN    60

NNNNNNNNNN NNNNNNNNNN NNNNNNNNNN NNNNNNNNNN NNNNNNNNNN NNNNNNNNNN   120

NNNNNNNNNN NNNNGACGTG                                              140

(2) INFORMATION FOR SEQ ID NO:106:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:106:

GTGAGTCCCG                                                          10

(2) INFORMATION FOR SEQ ID NO:107:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:107:

GATGAGNNNN NNNNNNNNNN NNNNNNNNNN NNNNNNNNCA AATG                    44

(2) INFORMATION FOR SEQ ID NO:108:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:108:

GTAAGTTAAG                                                          10

(2) INFORMATION FOR SEQ ID NO:109:

(i) SEQUENCE CHARACTERISTICS:
        (A) LENGTH: 110 base pairs
        (B) TYPE: nucleic acid
        (C) STRANDEDNESS: single
        (D) TOPOLOGY: linear
```

```
        (ii) MOLECULE TYPE: other nucleic acid
             (A) DESCRIPTION: /desc = "DNA"

(xi) SEQUENCE DESCRIPTION: SEQ ID NO:109:

TCTTGGNNNN NNNNNNNNNN NNNNNNNNNN NNNNNNNNNN NNNNNNNNNN NNNNNNNNNN         60

NNNNNNNNNN NNNNNNNNNN NNNNNNNNNN NNNNNNNNNN NNNNNAACAG                   110

(2) INFORMATION FOR SEQ ID NO:110:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
             (A) DESCRIPTION: /desc = "DNA"

(xi) SEQUENCE DESCRIPTION: SEQ ID NO:110:

GTAAGCATAT                                                                10

(2) INFORMATION FOR SEQ ID NO:111:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: other nucleic acid
             (A) DESCRIPTION: /desc = "DNA"

(xi) SEQUENCE DESCRIPTION: SEQ ID NO:111:

GCTGATNNNN NNNNNNNNNN NNNNNNNNNN NNNNNNNNNN NNNNNNNNNN NNNNNNNNNN         60

NNNNNNNNNN NNNCCTCCAG                                                     80

(2) INFORMATION FOR SEQ ID NO:112:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: other nucleic acid
             (A) DESCRIPTION: /desc = "DNA"

(xi) SEQUENCE DESCRIPTION: SEQ ID NO:112:

GTAAGCTGCA                                                                10

(2) INFORMATION FOR SEQ ID NO:113:

(i) SEQUENCE CHARACTERISTICS:
            (A) LENGTH: 168 base pairs
            (B) TYPE: nucleic acid
            (C) STRANDEDNESS: single
            (D) TOPOLOGY: linear (ii) MOLECULE TYPE: other nucleic acid
             (A) DESCRIPTION: /desc = "DNA"

(xi) SEQUENCE DESCRIPTION: SEQ ID NO:113:

GCATANNNNN NNNNNNNNNN NNNNNNNNNN NNNNNNNNNN NNNNNNNNNN NNNNNNNNNN         60

NNNNNNNNNN NNNNNNNNNN NNNNNNNNNN NNNNNNNNNN NNNNNNNNNN NNNNNNNNNN        120

NNNNNNNNNN NNNNNNNNNN NNNNNNNNNN NNNNNNNNNN NCTAGTGG                     168
```

(2) INFORMATION FOR SEQ ID NO:114:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:114:

GTAAGCCATG                                                                    10

(2) INFORMATION FOR SEQ ID NO:115:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:115:

GAATCNNNNN NNNNNNNNNN NNNNNNNNNN NNNNNNNNNN NNNNNNNNNN NNNNNNNNNN            60

NNNNNNNNNN NNNNNNNNNN NNNNNNNNNN NNNNNNNNNN NNNNNNNNNN NNNNNNNNNN           120

NNNNNNNNNN NNNNNNNNNN NNNNNNNNNN NNNNNNNNNN NNNNNNNNNN NNNNNNNNNN           180

NNNNNNNNTC CCTGG                                                            195

(2) INFORMATION FOR SEQ ID NO:116:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:116:

GTAAGCGCCC                                                                    10

(2) INFORMATION FOR SEQ ID NO:117:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:117:

GGATANNNNN NNNNNNNNNN NNNNNNNNNN NNNNNNNNNN NNNNNNNNNN NNNNNNNNNN            60

NNNNNNNNNN NNNNNNNNNN TTGATAG                                                87

(2) INFORMATION FOR SEQ ID NO:118:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:118:

GTAAGGCAAG                                                           10

(2) INFORMATION FOR SEQ ID NO:119:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:119:

CCCAGNNNNN NNNNNNNNNN NNNNNNNNNN NNNNNNNNNN NNNNNNNNNN NNNNNNNNNN    60

NNNNNNNNNN NNNNNNNNNN NNNNNNNNNN NNNNNNNNNN NNNNAAGTGG              110

(2) INFORMATION FOR SEQ ID NO:120:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:120:

GTACGTTCCT                                                           10

(2) INFORMATION FOR SEQ ID NO:121:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:121:

ACCAGANNNN NNNNNNNNNN NNNNNNNNNN NNNNNNNNNN NNNNNNNNNN NNNNNNNNNN    60

NNNNNNNNNN NNNNNNNNNN NNNNNNNNNN NNNNNNNNNN NNNNNNNNNN NNNNNNNNNN   120

NNNNNNNNNN NNNNNNNNNN NNNNNNNNNN NNNNNNNNNN NNNNNNNNNN NNNNNNNNNN   180

NNNNNNNNNN NNNNNNNNNN NNNNNNNNNN NNNNNNNNNN NNNNNNNNNN NNNNNNNNNN   240

NNNNNNNNNN NNNNNNNNNN NNNNNNNNNN NNNNNNNNNN NNNNNNNNNN NNNNNNNNNN   300

NNNNNNNNNN NNNNNNNNNN NNNNNNNNNN NNNNNNNNNN NNNNNNNNNN NNNNNNNNNN   360

NNNNNNNNNN NNNNNNNNNN NNNNNNNNNN NNNNNNNNNN NNNNNNNNNN NNNNNNNNNN   420

NNNNNNNNNN NNNNNNNNNN NNNNNNNNNN NNNNNNNNNN NNNNNNNNNN NNNNNNNNNN   480

NNNNNNNNNN NNNNNNNNNN NNNNNNNNNN NNNNNNNNN                          519
```

HUMAN α-7 NICOTINIC RECEPTOR PROMOTER

This invention was made with government support under National Institutes of Health Grants MH36321, DA09457, AG00029, and MH44212, and the Veterans Administration Medical Research Service. The Government has certain rights in the invention.

FIELD OF THE INVENTION

The present invention is related to the α7 neuronal nicotinic acetylcholine receptor gene. In particular, the present invention provides the human α7 gene.

BACKGROUND OF THE INVENTION

Schizophrenia is the most common chronic psychotic disorder of humans, affecting approximately one percent of the population worldwide (Eaton, Epidemiol. Rev., 7:105 [1985]). The mean lifetime risk of schizophrenia has been estimated at one percent (Eaton, supra). As the onset of disease usually occurs early in life, and results in serious chronic impairment of cognition, behavior, and emotional state, schizophrenia is a major social problem in terms of cost, lost potential and productivity, and family stress. Furthermore, estimates indicate that the mortality of schizophrenic patients is twice that of the general population (Tsuang et al., Arch. Gen. Psychiat., 36:1295 [1979]). The medical care of schizophrenic patients also presents a significant challenge, as the patients are often unable to provide an accurate medical history, and have difficulty complying with medical treatment.

The essential features of schizophrenia are the presence of psychotic symptoms during some phase of the illness, a chronic course, and deterioration in function. However, no combination of signs or symptoms is truly pathognomic of the disease. The DSM-IV criteria for schizophrenia (See, Hyman, "Schizophrenia," in Dale and Federman (eds), Scientific American Medicine, New York, N.Y. [1994], 13 VII: 1–5), requires a duration of at least six months, and a deterioration in function. Psychotic symptoms typically exhibited by schizophrenia patients include disturbances in perception, abnormalities in thought content, and abnormalities in the form of thought. Perceptual disturbances typically consist of hallucinations and illusions. The course of schizophrenia is variable, although it is generally characterized by periods with exacerbation of psychotic symptoms, followed by periods of remission. Over a period of years, social and cognitive function usually deteriorates. Suicide attempts and depression are common. As measured by frequency and severity of relapses, continuing symptoms, and overall functioning, approximately 80% of schizophrenics have a poor outcome (Breier et al., Arch. Gen. Psychiat., 48:239 [1991]).

Although family, twin, and adoption studies indicate that schizophrenia has a significant genetic component, these studies also show that the inheritance of schizophrenia is complex, involving an uncertain mode of transmission, incomplete penetrance, and probable genetic heterogeneity (Risch, Genet. Epidemiol., 7:3 [1990]; and Tsuang, Brit. J. Psychiat., 163:299 [1993]). Linkage studies using schizophrenia and related psychiatric cases as phenotypes have found possible loci for schizophrenia at various chromosomal sites in subsets of families (Pulver et al., Am. J. Med. Genet., 54:44 [1994]; Coon et al., Am. J. Med. Genet., 54:12 [1994]; Wang et al., Nature Genet., 10:41 [1995]; and Silverman et al., Am. J. Med. Genet., 67:162 [1996]). However, the findings do not account completely for the inheritance of schizophrenia, nor do they delineate which aspects of this multifactorial illness might be influenced by a specific locus.

A variety of psychiatric disorders may mimic schizophrenia and the symptoms of many disorders are similar. Thus, diagnosis has been based on the course of illness (for example, acute onset and episodic course in mania, compared with an insidious onset and chronic course in schizophrenia). In addition to schizophrenia, psychotic symptoms may also occur as a result of metabolic disturbances, structural brain lesions, other medical conditions, or drug toxicity. Thus, the differential diagnosis of schizophrenia must take into consideration such medical conditions as central nervous system neoplasm, hyperviscosity syndromes (i.e., due to hematologic malignancy), paraneoplastic syndromes, anoxia and postanoxic encephalopathy, hypertensive encephalopathy, AIDS encephalopathy, encephalitis, meningitis, brain abscess, Lyme disease, neurosyphilis, acute intermittent porphyria, Addison's disease, Cushing's disease, hepatic encephalopathy, hypocalcemia, hypercalcemia, hypoglycemia, hypothyroidism, hyperthyroidism, Alzheimer's disease, complex partial seizures, Huntington's disease, multiple sclerosis, stroke, Wilson's disease, folic acid deficiency, pellagra, vitamin $B_{12}$ deficiency, and lupus cerebritis. Some drugs, such as alcohol, high-dose cocaine, high-dose amphetamines, marijuana, phencyclidine (PCP), hallucinogens, sedative-hypnotics, meperidine, non-steroidal anti-inflammatory drugs, pentazocine and other opiate mixed agonist-antagonists, anti-tuberculosis drugs (e.g., cycloserine, isoniazid, rifampin), other antimicrobials, anticholinergic anti-parkinsonians, antihistamines (e.g., diphenhydramine), atropine and derivatives, cyclic antidepressants, low-potency antipsychotic drugs (e.g., thioridazine and clozapine), meclizine, scopolamine, antiarrhythmic (e.g., amiodarone, digitalis, and procainamide), captopril, amantadine, $D_2$ dopamine receptor antagonists (e.g., bromocriptine, and pergolide), levodopa, estrogens, testosterone, glucocorticoids and adrenocorticotropic hormone (ACTH), thyroid replacement overdose, cimetidine, ranitidine, dextroamphetamine, methylphenidate, and over-the-counter decongestants (e.g., pseudoephedrine), diet pills, and pep pills, are commonly associated with psychotic symptoms.

Treatment of schizophrenic patients usually involves the use of anti-psychotic drugs (e.g., haloperidol, haloperidol-like drugs, and clozapine), maintenance of a safe, predictable environment, and supportive psychotherapy to improve social and coping skills of patients. Stress reduction also appears to prevent relapses. While these drugs are useful in treating the symptoms of schizophrenia, there are also problems associated with their use. For example, the use of clozapine is complicated by the idiosyncratic occurrence of agranulocytosis, necessitating weekly monitoring of the white blood cell counts of patients taking this drug (See, Hyman, supra).

Despite advances in treatment and diagnostic methods, there remains a need for methods to diagnose and treat schizophrenic patients. Indeed, methods to diagnose and screen large populations for genetic component(s) associated with schizophrenia, as well as other psychoses are needed in order to provide reliable diagnoses that are not dependent upon the multifactorial criteria presently in use. Improved methods of treatment are also needed, including drugs and other therapeutics that do not have the side effects and other undesirable properties associated with the currently used drugs.

SUMMARY OF THE INVENTION

The present invention is related to the α7 neuronal nicotinic acetylcholine receptor gene. In particular, the present invention provides the human α7 gene.

In one embodiment, the present invention provides an isolated nucleotide sequence encoding at least a portion of the human alpha-7 nicotinic receptor, wherein the sequence is selected from the group consisting of SEQ ID NOS:84–103. In an alternative embodiment, the present invention provides an isolated peptide sequence encoded by the isolated nucleotide sequence, wherein the nucleotide sequence is selected from the groups consisting of SEQ ID NOS:84–103. In another embodiment, the nucleotide sequence further comprises 5' and 3' flanking regions. In yet another embodiment, the nucleotide sequence further comprises intervening regions. In a further embodiment, the present invention provides an isolated polynucleotide sequence comprising a combination of two or more nucleotide sequences, wherein the nucleotide sequences are selected from the group consisting of SEQ ID NOS:84–103. It is not intended that the combination comprise any particular number or order of these nucleotide sequences, nor is it intended that the combination be limited to the inclusion of any particular nucleotide sequence.

In another embodiment, the present invention provides vectors comprising a nucleotide sequence, wherein the nucleotide sequence comprises at least one nucleotide sequence selected from the group consisting of SEQ ID NOS:84–103. In another embodiment, the present invention provides a host cell transformed with a vector comprising a nucleotide sequence, wherein the nucleotide sequence comprises at least one nucleotide sequence selected from the group consisting of SEQ ID NOS:84–103. In one embodiment, the host cell is selected from the group consisting of bacteria, yeast, amphibian, and mammalian cells. In one preferred embodiment, the host cell is a human cell. In an alternative preferred embodiment, the the host cell is a cell line, while in another preferred embodiment, the host cell is contained within an animal.

The present invention also provides a first polynucleotide sequence comprising at least fifteen nucleotides, which hybridizes under stringent conditions to at least a portion of a second polynucleotide sequence, wherein the second polynucleotide sequence is selected from the polynucleotide sequences selected from the group consisting of SEQ ID NOS:84–103.

The present invention also provides methods for detection of a polynucleotide encoding alpha-7 protein in a biological sample suspected of containing the polynucleotide encoding alpha-7, comprising the step of hybridizing at least a portion of a polynucleotide sequence selected from the group consisting of SEQ ID NOS:9–11, and 84–103, to nucleic acid of the biological sample to produce an hybridization complex. In one embodiment, the method further comprises the step of detecting the hybridization complex, wherein the presence of the complex correlates with the presence of a polynucleotide encoding alpha-7 in the biological sample. In another embodiment, the biological sample is a sample selected from the group consisting of brain tissue and blood. In one preferred embodiment, the biological sample is from a human. In yet another embodiment, the human is suspected of suffering from a condition selected from the group consisting of schizophrenia, small cell lung carcinoma, breast cancer, and nicotine-dependent illness. In yet another preferred embodiment of the method, the nucleic acid of the biological sample is amplified by the polymerase chain reaction prior to hybridization.

The present invention also provides methods for amplification of nucleic acid from a sample suspected of containing nucleic acid encoding alpha-7, comprising the steps of: providing a test sample suspected of containing amplifiable nucleic acid encoding alpha-7; isolating the amplifiable nucleic acid from the test sample; combining the amplifiable nucleic acid with amplification reagents, and at least two primers selected from the group consisting of primers having the nucleic acid sequence set forth in SEQ ID NOS:1–8, and 12–83 to form a reaction mixture; and combining the reaction mixture with an amplification enzyme under conditions wherein the amplifiable nucleic acid is amplified to form amplification product. In one embodiment, the method further comprises the step of detecting the amplification product. In an alternative embodiment, the detecting is accomplished by hybridization of the amplification product with a probe having the nucleic acid sequence is selected from group of the sequences set forth in SEQ ID NO:9–11. In one preferred embodiment, the test sample is a sample selected from the group consisting of brain tissue and blood. In an alternative preferred embodiment, the test sample is from a human. In yet another embodiment, the human is suspected of suffering from a condition selected from the group consisting of schizophrenia, small cell lung carcinoma, breast cancer, and nicotine-dependent illness.

The present invention also provides methods for amplification of nucleic acid from a sample suspected of containing nucleic acid encoding alpha-7 comprising the steps of: providing a test sample suspected of containing amplifiable nucleic acid encoding alpha-7; isolating the amplifiable nucleic acid from the test sample; combining the amplifiable nucleic acid with amplification reagents, and a first primer set comprising at least two primers selected from the group consisting of the sequences set forth in SEQ ID NOS: 65–70, to form a first reaction mixture; combining the reaction mixture with an amplification enzyme under conditions wherein the amplifiable nucleic acid is amplified to form a first amplification product; combining the first reaction mixture with amplification reagents, and a second primer set comprising at least two primers selected from the group consisting of the sequences set forth in SEQ ID NOS:57–59, 61, 63, 67, and 73–75, to form a second reaction mixture; combining the second reaction mixture with an amplification enzyme under conditions wherein the amplifiable nucleic acid is amplified to form a second amplification product; and detecting the first or second amplification product.

In one preferred embodiment of the method, the detecting comprises hybridizing the amplification product with a probe having a nucleic acid sequence selected from the group consisting of the nucleic acid sequence set forth in SEQ ID NOS:9–11. In yet another embodiment, the test sample is a sample selected from the group consisting of brain tissue and blood. In another preferred embodiment of the method, the test sample is from a human. In a further embodiment, the is suspected of suffering from a condition selected from the group consisting of schizophrenia, small cell lung carcinoma, breast cancer, and nicotine-dependent illness.

The present invention also provides methods for producing anti-α7 antibodies (including, but not limited to antibodies directed against peptides comprising α7), comprising, exposing an animal having immunocompetent cells to an immunogen comprising at least an antigenic portion of α7 protein, under conditions such that immunocompetent cells produce antibodies directed against the portion of α7. In preferred embodiments, the α7 peptide or protein is human α7. In one embodiment, the method further comprises the step of harvesting the antibodies. In an alternative embodiment, the method comprises the step of fusing the immunocompetent cells with an immortal cell line under conditions such that an hybridoma is produced. In other embodiments, the immunogen comprises a fusion protein.

The present invention also provides methods for detecting abnormal α7 expression comprising the steps of: a) providing a sample suspected of containing test α7; and a control containing a quantitated α7; and b) comparing the test α7 in the sample with the quantitated α7 in the control to determine the relative concentration of the test α7 in the sample. In one embodiment of the method, the control contains a higher concentration of quantitated α7 than the concentration of the test α7 in the sample. Thus, the methods are capable of identifying samples (e.g., patient samples) with reduced α7 protein. The methods also provide means to detect samples that contain a normal amount of α7 protein. In addition, the methods may be conducted using any suitable means to determine the relative concentration of α7 in the test and control samples, including but not limited to the means selected from the group consisting of Western blot analysis, Northern blot analysis, Southern blot analysis, denaturing polyacrylamide gel electrophoresis, reverse transcriptase-coupled polymerase chain reaction, enzyme-linked immunosorbent assay, radioimmunoassay, and fluorescent immunoassay. Thus, the methods may be conducted to determine the presence of α7 in the genome of the animal source of the test sample, or the expression of α7 (mRNA or protein), as well as detect the presence of abnormal or mutated α7 proteins or gene sequences in the test samples.

In one preferred embodiment, the presence of α7 is detected by immunochemical analysis. For example, the immunochemical analysis can comprise detecting binding of an antibody specific for an epitope of α7. In an another preferred embodiment of the method, the antibody comprises polyclonal antibodies, while in another preferred embodiment, the antibody is comprises monoclonal antibodies.

The antibodies used in the methods invention may be prepared using various immunogens. In one embodiment, the immunogen is a human α7 peptide to generate antibodies that recognize human α7. Such antibodies include, but are not limited to polyclonal, monoclonal, chimeric, single chain, Fab fragments, and an Fab expression library.

Various procedures known in the art may be used for the production of polygonal antibodies to α7 (e.g., human α7). For the production of antibody, various host animals can be immunized by injection with the peptide corresponding to the human α7 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed against α7, any technique that provides for the production of antibody molecules by continuous cell lines in culture may be used (See, e.g., Harlow and Lane, Antibodies: A Laboratory Manual, Cold Spring Harbor Laboratory Press, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g. Kozbor et al. Immunol. Today 4:72 [1983]), and the EBV-hybridoma technique to produce human monoclonal antibodies (Cole et al., in Monoclonal Antibodies and Cancer Therapy, Alan R. Liss, Inc., pp. 77–96 [1985]).

In an additional embodiment of the invention, monoclonal antibodies can be produced in germ-free animals utilizing recent technology (See e.g., PCT/US90/02545). According to the invention, human antibodies may be used and can be obtained by using human hybridomas (Cote et al., Proc. Natl. Acad. Sci. U.S.A. 80:2026–2030 [1983]), or by transforming human B cells with EBV virus in vitro (Cole et al., in Monoclonal Antibodies and Cancer Therapy, Alan R. Liss, pp. 77–96 [1985]).

According to the invention, techniques described for the production of single chain antibodies (U.S. Pat. No. 4,946, 778; herein incorporated by reference) can be adapted to produce α7 single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for α7.

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art (e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of α7 (e.g., for Western blotting), measuring levels thereof in appropriate biological samples, etc. The antibodies can be used to detect α7 in a biological sample from an individual. The biological sample can be a biological fluid, such as but not limited to, blood, serum, plasma, cerebrospinal fluid (CSF), and the like, containing cells. In particular, α7 can be detected from cellular sources, such as, but not limited to, brain tissue.

The biological samples can then be tested directly for the presence of α7 using an appropriate strategy (e.g., ELISA or radioimmunoassay) and format (e.g., microwells, dipstick [e.g., as described in International Patent Publication WO 93/03367], etc.). Alternatively, proteins in the sample can be size separated (e.g., by polyacrylamide gel electrophoresis (PAGE), in the presence or not of sodium dodecyl sulfate (SDS), and the presence of α7 detected by immunoblotting (Western blotting)). Immunoblotting techniques are generally more effective with antibodies generated against a peptide corresponding to an epitope of a protein, and hence, are particularly suited to the present invention.

The foregoing explanations of particular assay systems are presented herein for purposes of illustration only, in fulfillment of the duty to present an enabling disclosure of the invention. It is to be understood that the present invention contemplates a variety of immunochemical assay protocols within its spirit and scope.

In some preferred aspects, genomic DNA or mRNA is amplified by PCR, and the amplified DNA is tested for the presence of mutation(s). PCR amplification is well known in the art (Cameron et al., Science 257:383–387 [1992]; Saksela et al., 1994, Proc. Natl. Acad. Sci. U.S.A., 91:1104–1108 [1994]). For example, mRNA can be detected by reverse transcriptase-initiated PCR (See, e.g., Saksela et al., J. Virol., 67:7423–27 [1993]). PCR can be carried out (e.g., by use of a Perkin-Elmer Cetus thermal cycler and Taq polymerase (e.g., Gene Amp®, Boehringer Mannheim). The amplified PCR products can be analyzed by immobilization on membranes and hybridization with specific oligonucleotide probes, or by treatment with specific endonucleases and analysis of the products by gel electrophoresis. Labeling of the cleaved PCR products can be accomplished by incorporation of radiolabeled nucleotides, endlabeling (e.g., with $^{32}$P-ATP), or by staining with ethidium bromide.

The present invention also provides methods and compositions suitable for gene therapy for individuals deficient in α7 expression, production, or function. Viral vectors commonly used for in vivo or ex vivo targeting and therapy procedures are DNA-based vectors and retroviral vectors. Methods for constructing and using viral vectors are known in the art (See, e.g., Miller and Rosman, BioTechn., 7:980–990 [1992]). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome which are necessary for encapsidating the viral particles. DNA viral vectors include an attenuated or defective DNA virus, including, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320–330 [1991]), defective herpes virus vector lacking a glycoprotein L gene (See e.g., Patent Publication RD 371005 A], or other defective herpes virus vectors (See e.g., International Patent Publication No. WO 94/21807; and International Patent Publication No. WO 92/05263); an attenuated adenovirus vector, such as the vector described by Stratford-Perricaudet et al. (J. Clin. Invest., 90:626–630 [1992]; See also, La Salle et al., Science 259:988–990 [1993]); and a defective adeno-associated virus vector (Samulski et al., J. Virol., 61:3096–3101 [1987]; Samulski et al., J. Virol. 63:3822–3828 [1989]; and Lebkowski et al., Mol. Cell. Biol., 8:3988–3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma(IFN-γ), or anti-CD4 antibody, can be administered to block humoral r cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See, WO94/26914). Those adenoviruses of animal origin which can be used within the scope of the present invention include adenoviruses of canine, bovine, murine (e.g., Mavl, Beard et al., Virol., 75–81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800), for example).

In another embodiment the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; International Patent Publication No. WO 95/07358; and Kuo et al., Blood 82:845 [1993]). The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus". MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference); the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences which may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. U.S.A., 84:7413–7417 [1987]; See also, Mackey, et al., Proc. Natl. Acad. Sci. U.S.A., 85:8027–8031 [1988]; Ulmer et al., Science 259:1745–1748 [1993]). The use of cationic lipids may promote encapsulation of negatively charged nucleic acids, and also promote fusion with negatively charged cell membranes (Felgner and Ringold, Science 337:387–388 [1989]). Particularly useful lipid compounds and compositions for transfer of nucleic acids are described in International Patent Publications WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25.508), or a cationic polymer (e.g., International Patent Publication WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. J. Biol. Chem., 267:963–967 [1992]; Wu and Wu, J. Biol. Chem., 263:14621–14624 [1988]; Williams et al., Proc. Natl. Acad. Sci. U.S.A., 88:2726–2730 [1991]). Receptor-mediated DNA delivery approaches can also be used (Curiel et al., Hum. Gene Ther., 3:147–154 [1992]; Wu and Wu, J. Biol. Chem., 262:4429–4432 [1987]).

The present invention also provides methods and compositions for the production of in vitro cell cultures that express wild-type or mutated human α7, as well as transgenic animals capable of expressing wild-type or mutated human α7. For example, the genomic α7 clone can be expressed in mammalian cells (e.g., cell lines, including but not limited to mammalian kidney cells, such as HEK). It is also contemplated that in some embodiments, the cells and animals also express other foreign genes in conjunction with the introduced α7.

The present invention also provides methods for producing non-human transgenic animals, comprising the steps of a) introducing into an embryonal cell of a non-human animal a polynucleotide sequence encoding an α7 protein; b) transplanting the transgenic embryonal target cell formed thereby into a recipient female parent; and c) identifying at least one offspring containing the transgene wherein the α7 mRNA is overexpressed in the tissue of the offspring. In one preferred embodiment, the α7 mRNA is human α7 mRNA. In an alternative embodiment, the polynucleotide sequence encoding an α7 protein comprises a yeast artificial chromosome, while in another embodiment, the polynucleotide sequence encoding an α7 is a bacterial artificial chromosome, and in yet another embodiment, the polynucleotide sequence encoding an α7 protein is a P1 artificial chromosome. In a further embodiment, the non-human animal is a member of the Order Rodentia. In a preferred embodiment, the non-human animal is a mouse.

DESCRIPTION OF THE FIGURES

FIG. 1 is a table showing the exon-intron boundary sequences of the human α7 nAChR subunit gene. The 3' portion of exon 1 is disclosed as SEQ ID NO:84. Also shown are the splice acceptor sequences of: intron 1 (SEQ ID NO:85), intron 2 (SEQ ID NO:86), intron 3 (SEQ ID NO:87), intron 4 (SEQ ID NO:88), intron 5 (SEQ ID NO:89), intron 6 (SEQ ID NO:90), intron 7 (SEQ ID NO:91), intron 8 (SEQ ID NO:92) and intron 9 (SEQ ID NO:93), as well as the splice donor sequences of: intron 1 (SEQ ID NO:104), intron 2 (SEQ ID NO:106), intron 3 (SEQ ID NO:108), intron 4 (SEQ ID NO:110, intron 5 (SEQ ID NO:112), intron 6 (SEQ ID NO:114), intron 7 (SEQ ID NO:116), intron 8 (SEQ ID NO:118), and intron 9 (SEQ ID NO:120). Additionally, flanking exon sequences are shown: exon 2 (SEQ ID NO:105), exon 3 (SEQ ID NO:107), exon 4 (SEQ ID NO:109), exon 5 (SEQ ID NO:111), exon 6 (SEQ ID NO:113), exon 7 (SEQ ID NO:115), exon 8 (SEQ ID NO:117), exon 9 (SEQ ID NO:119), and exon 10 (SEQ ID NO:121).

FIG. 2 is a table showing the sequence variants identified in full-length and duplicated genomic clones.

FIG. 3 is a table showing an expression analysis of sequence variants.

FIG. 4 shows the nucleotide sequence of the region 5' of the human α7 nAChR subunit gene (SEQ ID NO:94).

Figure 5:
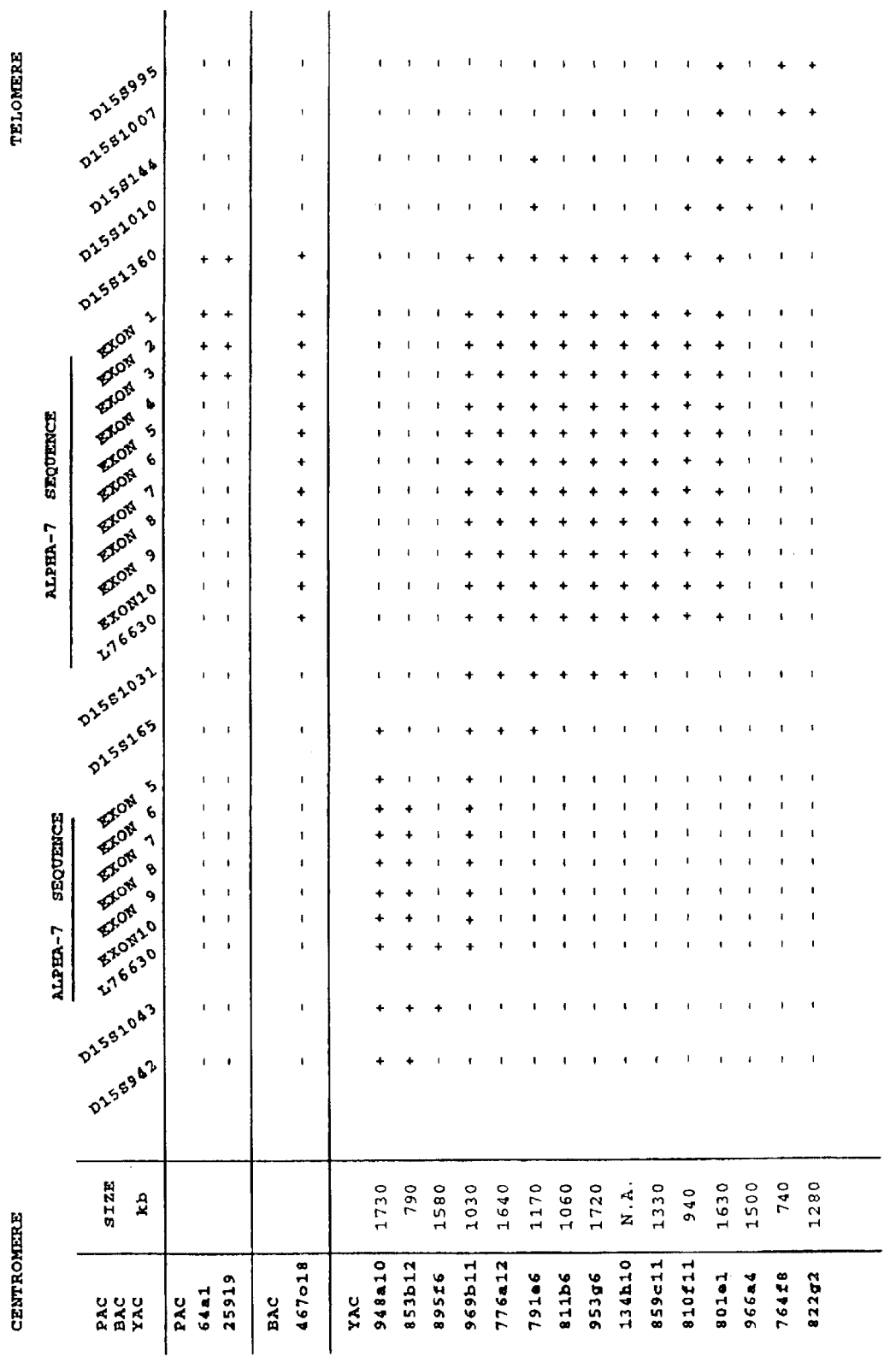

FIG. 5 shows the genomic contig of clones positive for α7 nAChR gene sequences and surrounding loci.

FIG. 6 shows a partial sequence of a RACE clone, with exon sequences shown in upper case and intron sequences shown in lower case: exon D (SEQ ID NO:95), exon C (SEQ ID NO:96), exon B (SEQ ID NO:97), exon A (SEQ ID NO:98), exon 5 (SEQ ID NO:99), and exon 6 (SEQ ID NO:100).

FIG. 8 shows the DNA sequence of the human α7 neuronal nicotinic receptor promoter (SEQ ID NO:101).

FIG. 9 shows the DNA sequence of the alternatively spliced human α7 neuronal nicotinic receptor RACE product A/C/D (SEQ ID NO:102).

FIG. 10 shows the DNA sequence of the alternatively spliced human α7 neuronal nicotinic receptor RACE product A/B/C/D (SEQ ID NO:103).

DESCRIPTION OF THE INVENTION

Figure 7:
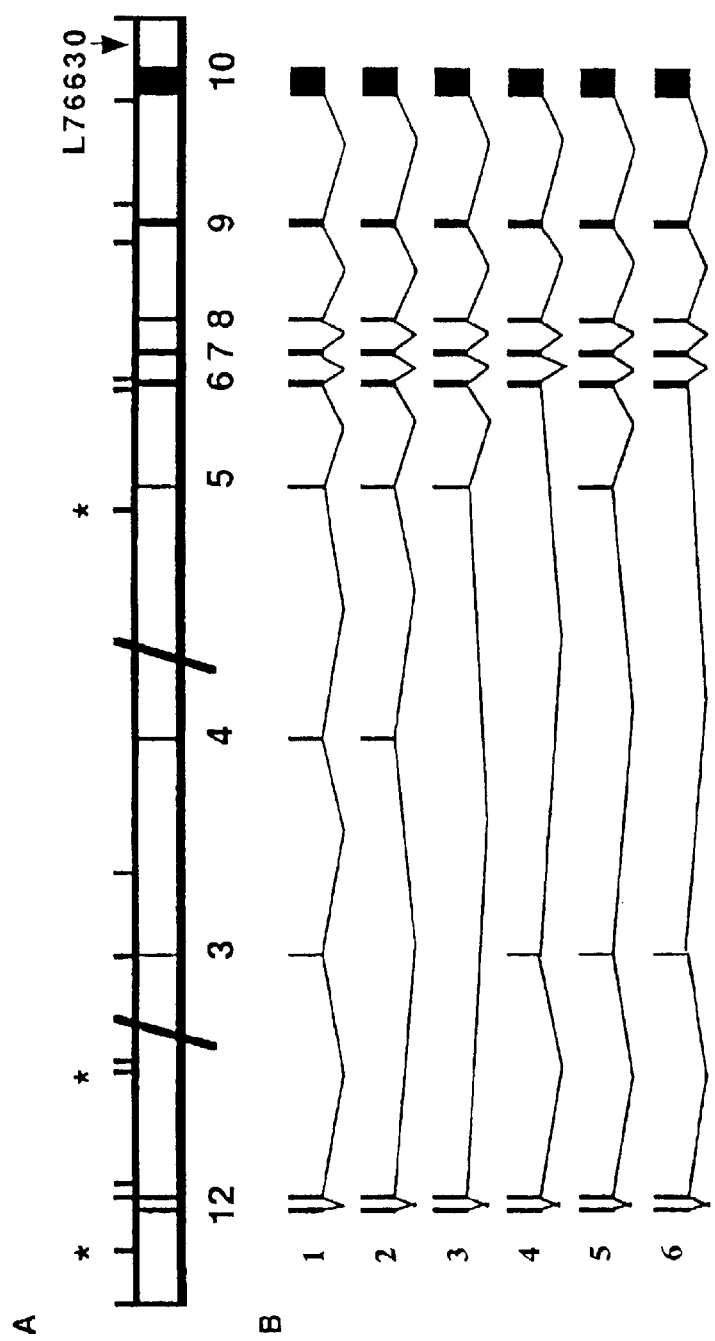
FIG. 7 provides a map of the full-length α7 nAChrR gene. Panel A shows a physical map of the region and the structure of the full-length α7 nAChR gene. Panel B shows the structure of alternatively spliced transcripts.

As the current methods have been unsuccessful in providing needed information regarding the genetics of schizophrenia, an alternative strategy for genetic studies of complex diseases involving the use of a specific neurobiological characteristic of the illness (e.g., as an additional phenotype more closely reflecting the effect of a single genetic alteration), was used during the development of the present invention. Such information is needed in order to provide diagnostic and treatment methods, as well as animal models for schizophrenia, as well as other psychoses. It is contemplated that such a trait is part of the inherited diathesis of the illness, which produces schizophrenia in combination with other pathogenic elements.

The present invention provides genetic information (i.e., sequences, including sequence location and information for intron/exon boundaries) for the α7 nicotinic receptor, as well as methods to assess the function of this receptor in normal, as well as schizophrenic individuals. The present invention also provides methods and compositions for analyzing samples from patients suspected of suffering from diverse conditions, including epilepsy (e.g., juvenile myoclonic epilepsy), small cell lung carcinoma and other nicotine-dependent diseases, Prader-Willi, Angelman's syndrome, and other genetic disorders, etc. Indeed, it is not intended that the present invention be limited to schizophrenia.

The following description of the present invention is arranged in four sections, including (I) Inhibition of the P50 Auditory Response; (II) Neuronal Nicotinic Receptor Subunit Family; (III) Treatment and Diagnosis of Schizophrenia and Other Psychoses; and (IV) Transgenic Animals.

I. Inhibition of the P50 Auditory Response

Various psychophysiological paradigms demonstrate altered brain functions in schizophrenic patients and their relatives that might reflect inherited traits (See e.g., Sham et al., Psychiat. Genet., 4:29 [1994]; De Amicis et al., J. Nerv. Ment. Dis., 174:177 [1986]; Holzman et al., Arch. Gen. Psychiat., 45:641 [1988]; and Braff et al., Arch. Gen. Psychiat., 49:206 [1992]). Basic deficits in the regulation of response to sensory stimuli may underlie patients' more apparent symptoms such as hallucinations and delusions. In addition to hearing voices, patients often attend to apparently extraneous stimuli in their surroundings that normal individuals generally ignore. Such symptoms suggested that neuronal mechanisms responsible for the filtering or gating of sensory input to higher brain centers are deficient. One method developed for examining such neuronal mechanisms compares the responses to first and second of paired stimuli. The first stimulus elicits an excitatory response that also activates inhibitory mechanisms, which then diminish the excitatory response to the second stimulus. The ratio of the amplitude of the second response to the first is inversely related to the strength of inhibition.

During the development of the present invention, this method was used to study the response to auditory stimuli in schizophrenia, using an electrically positive evoked potential occurring 50 ms after an auditory stimulus (P50). Inhibition of the P50 response to a second identical stimulus, presented 500 ms after the first, has been reported to be diminished in schizophrenics (Adler et al., Biol. Psychiat., 17:639 [1982]; Boutros and Overall, Clin. Electroencephalog., 22:20 [1991]; Erwin et al., Biol. Psychiat., 30, 430 [1991]; and Judd et al., Am. J. Psychiat., 149:488 [1992]). This diminished inhibition, measured as an elevation in the ratio of P50 amplitudes, has been correlated with schizophrenics' decreased performance in a neuropsychological measure of sustained attention, as well as diminished performance in a word recognition task (Cullum et al., Schizophrenia Res., 10:131 [1993]; and Vinogradova et al., Biol. Psychiat., 39:821 [1996]).

In the development of the present invention, inhibition of the P50 response was measured in animal and related clinical investigations, to identify neurobiological mechanisms related to genes of interest, as well as a phenotype for linkage analysis to identify chromosomal areas containing genes responsible for the abnormality in schizophrenics.

The neurobiological inhibition of human P50 to repeated auditory stimuli was initially investigated using an auditory evoked potential recorded from the rat as a model. Both the human and rat potentials show similar decreased responses to repeated auditory stimuli (Adler et al., Biol. Psychiat., 21:787 [1986]). Neuronal recordings identified the pyramidal neurons of the hippocampus as a major source of the rat evoked potential. These pyramidal neurons have a decremented response to repeated auditory stimuli that parallels the decrement in the evoked potential (Bickford-Wimer et al., Biol. Psychiat., 27:183 [1990]). The decrement is lost after transection of the fimbria-fornix, a fiber tract that includes afferents to the hippocampus from cholinergic neurons in the basal forebrain (Vinogradova, in The Hippocampus 2: Neurophysiology and Behavior, Issacson and Pribram (eds), Plenum Press, New York, N.Y., [1975], pp 3–69).

However, nicotine has been found to normalize inhibition of response in the fimbria-fornix lesioned animals (See e.g., Bickford and Wear, Brain Res., 705:235 [1995]). Studies with pharmacological antagonists in unlesioned animals indicate that a specific subset of nicotinic cholinergic receptors is involved in the inhibitory mechanism. The inhibition is selectively blocked by the snake toxin α-bungarotoxin (Luntz-Leybman et al., Brain Res., 587:130 [1992]), suggesting that the receptor contains the α7 nicotinic cholinergic receptor subunit, as it is the only known nicotinic receptor subunit in the mammalian brain sensitive to this toxin (Couturier et al., Neuron 5:847–856 [1990]; Schoepfer et al., Neuron 5:35 [1990])). Neither scopolamine, mecamylamine, nor κ-bungarotoxin (ie., antagonists of other types of cholinergic receptors), blocked the inhibition. Receptor autoradiography using $[^{125}I]$-α-bungarotoxin showed the most intense binding to non-pyramidal hippocampal neurons containing the inhibitory neurotransmitter γ-aminobutyric acid (Freedman et al., J. Neurosci., 13:1965 [1993]). This labeling was consistent with physiological evidence that cholinergic synapses activate interneurons, which inhibit the pyramidal neuron response to the second stimulus (See e.g., Miller and Freedman, Neurosci., 69:371–381 [1995]; and Hershman et al., Neurosci. Lett., 190:133 [1995]).

There are several areas of apparent concordance between these findings in rats and P50 inhibition in humans. First, P50 has been recorded from the human hippocampus (Goff et al., Prog. Clin. Neurophysiol., 7:126 [1980]; and Makela et al., Electroencephalogr. Clin. Neurophysiol., 92:414 [1994]), and human hippocampal neurons have rapidly decreasing responses to auditory stimuli, similar to those observed with rat hippocampal neurons (Wilson et al., Exp. Neurol., 84:74 [1984]). Second, nicotine in high doses transiently normalizes the abnormality in P50 inhibition in schizophrenics and in their relatives, much as it normalizes inhibition in rats after fimbria-fornix lesions (Bickford and Wear, supra; Adler et al., Biol. Psychiatry 32:607[1992]; and Adler et al., Am. J. Psychiat., 150:1856 [1993]). However, the effect of nicotine on P50 inhibition in relatives of schizophrenics is not blocked by mecamylamine, which blocks all known nicotinic receptors in human brain, except the α7: nicotinic receptor (Freedman et al, Harvard Rev. Psychiat., 2:179 [1994]). In situ hybridization has shown that α7 nicotinic receptor mRNA is expressed in human hippocampal neurons (Freedman et al, Harvard Rev. Psychiat., 2:179 [1994]). Some of the non-pyramidal neurons of the human hippocampus were intensely labeled by α-bungarotoxin, as was also observed with rats.

A preliminary study showed that α-bungarotoxin labeling was decreased in post mortem hippocampus from eight schizophrenics (Freedman et al., Biol. Psychiat., 38:22 [1995]). In addition, schizophrenic patients are particularly heavy tobacco smokers, even when compared to other psychiatric patients (deLeon et al., Am. J. Psychiat., 152:453 [1995]; and Hamera et al., J. Nerv. Mental Dis., 183: 559 [1995]). This heavy nicotine use may reflect an attempt at self medication of an endogenous neuronal deficit (Goff et al., Am. J. Psychiat., 149:1189 [1992]). However, nicotine's efficacy as an anti-psychotic is limited, due to rapid desensitization and cardiovascular toxicity.

In parallel with these biological studies in human and animals, the P50 evoked potential abnormality was also investigated as a phenotype for genetic linkage analysis. A genome-wide scan was initiated, independent of any candidate gene hypothesis, in nine multiplex schizophrenic pedigrees, which were also phenotyped with P50 recordings. The deficit in inhibition of the P50 response in these and other schizophrenic families is generally found in one of the parents and half the siblings, including the schizophrenic probands (Siegel et al., Arch. Gen. Psychiat., 41:607–612 [1984]). Although elevated P50 ratios are significantly associated with the apparent genetic risk for schizophrenia, many individuals in the pedigrees who have the deficit are clinically unaffected (Waldo et al., Psychiat. Res. 39:257 [1991]). In this respect, the distribution of the trait resembles several other neurobiological abnormalities in schizophrenics and their relatives, such as deficits in smooth pursuit eye movements and reaction time (De Amicis et al., J. Nerv. Ment. Dis., 174:177 [1986]; and Holzman et al. Arch. Gen. Psychiat., 45:641 [1988]). These traits may represent alternative expressions of a latent trait or endophenotype, which, in combination with other pathogenic elements, gives rise to schizophrenia.

During the development of the present invention, preliminary linkage analyses between the P50 ratio abnormality and 318 restriction fragment length polymorphism and tandem repeat DNA markers in the nine kindreds were conducted. DNA markers mapping to four chromosomal regions, one of which was 15q14, revealed small positive lod scores (maximum logarithm of the odds) assuming autosomal dominant transmission. Subsequently, the α7 nicotinic receptor gene was localized to the 15q14 region (Orr-Urtrege et al., Genomics 26:399 [1995]; and Spitzer et al., Arch. Gen. Psychiat., 35:773 [1978]). As converging evidence from neurobiological investigations implicated α7 receptor function in abnormal P50 inhibition, and the preliminary linkage study provided suggestive evidence for heritability of the trait near the chromosomal location of the α7 receptor gene, additional experiments, using informative markers at the α7 receptor gene locus were undertaken. Two new DNA polymorphic loci were isolated, namely D15S1360 from a yeast artificial chromosome (YAC) containing the α7 nicotinic receptor gene, and L76630 from an α7-containing clone in a genomic phage library. These markers were used with over 500 highly polymorphic markers in a 10 centiMorgan resolution genome-wide scan of the nine pedigrees. The results demonstrate a highly significant linkage between D15S1360 and the abnormality in P50 suppression.

Indeed, the data obtained during the development of the present invention strongly suggest that the P50 auditory sensory deficit in schizophrenia is genetically linked to the locus of the α7 nicotinic receptor gene on chromosome 15q14. Thus, the present invention provides the heretofore unknown linkage between nicotinic receptors and schizophrenia. The significant linkage obtained with the P50 ratio phenotype supports the value of this strategy. This provides methods for assessing the effects of therapy to correct abnormalities in α7 structure and/or function, as well as providing methods for developing and identifying drugs suitable for use in treating such abnormalities.

Although an understanding of the mechanism is not necessary in order to use the present invention, it has been suggested that the clinical illness may be less penetrant, because multiple genetic and non-genetic factors are required to produce clinical illness, whereas a specific biological defect may occur as the result of a single gene effect. Thus, some gene carriers would be expected to have abnormal P50 ratio, the more penetrant phenotype, but not schizophrenia, which is less penetrant. The lower lod scores observed during the development of the present invention with schizophrenia as a phenotype support that position; several kindreds had higher lod scores for P50 ratio than for schizophrenia because there were many family members with abnormal P50 ratios who did not have schizophrenia.

The possibility that the chromosome 15q13–14 region is involved in psychotic illness has also been investigated in relationship to other diseases. For example, psychoses resembling schizophrenia have been observed in Prader-Willi syndrome, a mental retardation linked to deletions and abnormal DNA imprinting in the 15q11–13 region (Clarke, Brit. J. Psychiat., 163:680 [1993]). The imprinting abnormality affects the expression of many genes in this region. Several families in Sephardic and other populations have co-existent schizophrenia and Marfan's syndrome (i.e., a disease linked to dominant mutations in the fibrillin gene at 15q21; Sirota et al., Br. J. Psychiat., 157: 433 [1990]; and Melissari et al., Pathologica 87:78 [1995]). The co-segregation of the two illnesses may be based on their chromosomal proximity. Psychosis also occurs in a large French Canadian kindred that has a recessive demyelination disease linked to markers at 15q14 (Casaubon et al., Am. J. Hum. Genet., 58:28 [1996]). In addition, an Italian kindred contains two cousins with psychotic illness and a partial trisomy of chromosome 15, derived independently from abnormal meioses involving a balanced familial translocation with a 15q13 breakpoint, that was present in each of their mothers. It was suggested that the new trisomies may have caused the de novo appearance of illness (Calzolari et al., Am. J. Med. Genet., 67:154 [1996]). The present invention provides the means to determine to what extent the appearance of psychoses in these families with other genetic abnormalities at 15q13–14 involves the α7 gene.

In addition to providing means to assess the risk for development of schizophrenia, the present invention also provides new data about the identity of neuronal abnormalities involved in its pathophysiology, as well as the means to develop treatment methods and compounds, diagnostic methods and reagents, and models (e.g., cell lines and transgenic animals) of these neuronal abnormalities. These results are consistent with clinical and neurobiological evidence for the involvement of the α7 nicotinic receptor gene in sensory gating deficits in schizophrenia.

The present invention also provides the means to determine the role the α7 receptor in the sensory processing defects and other abnormalities in schizophrenia. The finding of a significant linkage to support the role of the α7 nicotinic receptor in the pathophysiology of sensory and attentional disturbance in schizophrenia is unique. Many neurotransmitter systems have been hypothesized to be at least partly responsible for schizophrenia, but direct biological assessment of a specific neuronal receptor function in human subjects is generally not feasible because of the brain's complexity and inaccessibility. The present invention provides compositions and methods to overcome these drawbacks. Genetic investigations, including linkage studies, have represented the critical test of the involvement of a particular mechanism in schizophrenia. The present invention provides methods and compositions to complement and/or replace such tests for schizophrenia. Indeed, linkage at the α7 nicotinic receptor locus thus supports the neurobiological evidence that this gene plays a role in a pathophysiological aspect of schizophrenia, a role that prior to the present invention, had not been previously considered nor described, despite schizophrenics' well-known heavy dependence on nicotine.

II. Neuronal Nicotinic Receptor Subunit Family

As discussed above, during the development of the present invention, the α7 nicotinic receptor was associated with pathophysiological aspect(s) of schizophrenia. This receptor is a member of the neuronal nicotinic receptor subunit gene family, which is expressed in mammalian brain as pentameric, ligand-gated ion channels (Patrick et al., Ann. NY Acad. Sci., 505:194 [1987]; Cooper et al., Nature 350:235 [1991]; and Lindstrom et al., Ann. NY Acad. Sci., 757:100 [1996]). In the muscle, five different types of subunits constitute the holoreceptor, but in brain only two types of subunits, designated as "α" and "β" have been found (Galzi et al., Ann. Rev. Pharmacol., 31:37 [1991]; and Lukas and Bencherif, Int. Rev. Neurobiol., 34:25 [1992]).

Neuronal receptors can be functionally differentiated into two principal classes which differ in their affinity for nicotine and the snake toxin, α-bungarotoxin (Marks and Collins, Mol. Pharmacol., 22:554 [1982]; Wonnacott, J. Neurochem., 47:1706 [1986]; Marks et al., Mol. Pharmacol., 30:427 [1986]; and Amar et al., FEBS 327:284 [1993]). Receptors that bind nicotine with high affinity contain α2–α6 as ligand binding subunits and require an association with β subunits for functional expression (Goldman et al., Cell 48:965 [1987]; Deneris et al., Clin. Chem., 35:731 [1989]; and Wada et at., J. Compar. Neurol., 284:314 [1989]). A second class of receptors (α7–α9) bind nicotine with low affinity, have a high affinity for α-bungarotoxin, and function as homomeric ion channels in in vitro expression systems (Marks et al., [1986], supra; Wonnacott, [1986], supra; Alkondon and Albuquerque, J. Pharm. Ex. Ther., 265:1455 [1993]; Amar et al., FEBS 327:284 [1993]; and Zhang et al., Neuron 12:167 [1994]). The α7 receptor is the only α-bungarotoxin-binding receptor identified in mammalian brain, as α8 appears to be only expressed in chick (Schoepfer et al., Neuron 5:35 [1990]) and α9 has limited expression in cochlear hair cells and pituitary (Elgoyhen et al., Cell 79:705 [1994]). In addition, a cDNA clone of the human α7 was isolated from a human brain library (GenBank #U40583).

Expression and function of a specific subset of the nicotinic receptor family, the α7 receptor, has recently been implicated in a neuronal pathway controlling the filtering or gating of auditory stimuli in both human and rat brain (Adler et al., Biol. Psych., 32:607 [1992]; Adler et al., Am. J. Psychol., 150:1856 [1993]; Freedman et al., Harvard Rev. Psychiat., 2:179 [1994]; and Leonard et al., 1996). This sensory processing mechanism is aberrant in a majority of subjects with schizophrenia (Freedman et al., Schiz. Res., 4:233–243 [1991]). Pharmacological studies in both humans and rats suggest that the deficit in humans can be normalized by nicotine (Adler et al., [1992] supra; and Adler et al., [1993], supra) and reproduced in a rodent model by antagonists of the low affinity α7 nicotinic receptor but not by high affinity antagonists (Luntz-Leybman et al., Brain Res., 587:130 [1992]; and Rollins et al., Soc. Neurosci. Abst., 22:1272 [1996]). Expression of α-bungarotoxin binding receptors is decreased in schizophrenic hippocampi by approximately 40% (Freedman et al., Biol. Psychiat., 38:22 [1995]).

During the development of the present invention, the locus D15S1360, a polymorphic marker <120 kb from the full-length α7 nicotinic receptor gene at 15q14, was genetically linked to this auditory gating deficit in schizophrenic pedigrees. However, it is contemplated that other genes mapping to the 15q 14 region are potential alternative or additional genetic candidates to α7 for pathogenic features of schizophrenia.

Also during the development of the present invention, the expression of the α7 nicotinic receptor in human postmortem brain was localized. This expression was found to be widely expressed at low levels in most nuclei, but regions of highest expression included those involved in processing of sensory information, such as the hippocampus, lateral and medial geniculates, and the reticular nucleus of the thalamus.

The present invention further provides the physical mapping of a full-length human genomic clone for the α7 receptor subunit and sequencing of a putative promoter region. The gene and promoter structure are similar to that of the chick α7. Additionally, a partial α7 gene duplication including exons 5–10 and intervening intronic sequence, which lies <1 Mb from the full-length gene has been identified. In addition, four novel exons at the 5' end of the duplicated α7 sequences were sequenced and intron/exon junctions identified. The duplicated α7 sequences were found to be expressed as alternatively spliced transcripts containing some or all of these novel exons.

The present invention also provides the structural organization of the human α7 neuronal nicotinic acetylcholine receptor gene and presents data indicating a partial gene duplication. Large insert genomic clones were isolated from YAC, BAC and PAC libraries. There are 10 exons in the gene; the splice junctions are consistent with consensus splice sites (Green, Ann. Rev. Cell. Biol., 7:559 [1991]; Lamond, Bioessays 15:595 [1993]) and have an identical location to those in the chick α7 gene (Matter-Sadzinski et al., EMBO J., 11:4529 [1992]), the only species for which genomic α7 gene sequence has been previously published.

The promoter region of the gene was found to be 77% G/C, and contains no TATA box. It thus fits a growing group of eukaryotic promoters which demonstrate multiple transcription start sites (Maue et al., Neuron 4:223 [1990]; and Sauerwald et al., J. Biol. Chem., 265:14932 [1990]). The nucleotide sequence between the human and chick promoter regions was found to not be well conserved. However, there are consensus transcription factor binding sites located in similar positions in the two promoters (Matter-Sadzinski et al., [1992] supra). These include SP-1 and AP-2 binding sites. SP-1 and AP-2 consensus motifs are frequently found in other ligand-gated ion channel genes (See e.g., Bessis et al., Nucl. Acids Res., 21:2185 [1993]), and may contribute to neuronal specificity.

A cyclic AMP response element (CREB) binding site motif was also identified in the human promotor, but is not found in the chick gene. The presence of this CREB site in the human promoter is interesting since the mammalian α7 gene is known to be down-regulated by corticosterone (Pauly et al., "Glucocorticoid Regulation of Sensitivity to Nicotine," in The Biology of Nicotine: Current Research Issues, Raven Press, New York, N.Y., [1992], pp. 121–139), which affects expression of the CREB-binding protein. Thus, it is contemplated that corticosterone and other glucocorticoids will affect the α7 gene in some embodiments of the present invention.

In addition, alternative splicing of the full-length α7 gene was detected during the development of the present invention. Six different splice variants were identified by sequencing of full length transcripts. However, only one, missing exon 3, did not interrupt the frame of translation.

Several important motifs which affect correct splicing of heterogeneous RNA were identified during the development of the present invention. For example, there are two Chi(X) sequences (consensus: CCTGGTGG) known to enhance splicing, present in the human α7 gene of the present invention; there is one in intron 4 and one in the 3'-UT of the cDNA. Another group of splice enhancers with sequence (T)GCATG(A), have been localized as well. There are seven motifs of this enhancer class in sequence identified for intron 2 (approximately >25 kb in size). An additional enhancer of this type has been found in the large intron 4. It is contemplated that additional splicing motifs may be localized in the human α7 sequence.

Exons 5–10 of the α7 nicotinic receptor gene were found to be duplicated in the human genome. The duplicated sequences lie within 1 Mb and are centromeric to the full-length α7 gene on chromosome 15. The evidence for the duplication includes mapping of the duplicated sequences to a different site on a YAC contig of the region. Additionally, heterozygous polymorphic sequences at exonic sites and at the L76630 locus, located 1.4 kb beyond the 3' end of the coding region, were detected in both a somatic cell chromosome 15 hybrid and in a single YAC (969b11) containing both the full-length gene and duplicated α7 exons. The apparent arrangement of the duplication is head to tail in relation to the full length gene.

Further complexity for the α7 gene structure was introduced when it was determined that some of the RACE clones isolated during cloning of a human α7 cDNA contained only exons 5–10, and additional non-α7 sequences 5' of exon 5. These sequences were identical to sequences found in several EST clones that were located by homology screening with α7 cDNA sequence. The EST clones also contained only exons 5–10 of the α7 gene, with the previously unreported sequences again 5' of exon 5. PCR products from genomic DNA and from YACs 948a10 and 953g6 revealed that these non-α7 sequences were present in genomic clones containing either the full-length gene or the duplicated α7 sequences, and four novel exons were defined. It is contemplated that these sequences are arranged as alternatively spliced exons, as the positions of the consensus splice junctions between them correspond to the spliced products seen in the RACE and EST clones. These new exons were designated as "3'-α7A," "α7B," "α7C" and "α7D-5'." The RACE products were variable in their inclusion of exon B, similar to the EST clones.

Partial gene duplication has been implicated in human disease (See e.g., Hu and Worton, Hum. Mutat., 1:3 [1992]; Lehrman et al., Cell 48:827 [1987]; and Den-Dunnen, et al., Am. J. Hum. Genet., 45:835 [1989]). Thus, it is contemplated that although transcription of mRNAs containing the novel exons was found to occur at levels similar to those of the full-length coding region, the novel exons may be expressed only from the duplicated α7 sequences. In addition, there is also evidence for novel exons in another gene on chromosome 15, the small nuclear riboprotein-N (SNRPN); these exons at both the 5'- and 3'-ends of the SNRPN gene are also transcribed as alternative mRNAs.

It is contemplated that the human alternative transcripts containing the novel exons α7D, α7C, α7B, and α7A, might be translated. These alternatives lack the α7 signal peptide and disulfide bridge, which have been shown to be necessary for assembly of the homologous alpha subunit in muscle (Blount and Merlie, J. Cell Biol., 111:2613 [1990]). However, an alternatively spliced transcript of the muscle alpha, containing an additional exon, is expressed at equal levels to the correctly spliced isoform. It is also translated, but not assembled and is localized to the endoplasmic reticulum (Beeson et al., EMBO J., 9:2101 [1990]; and Newland et al., J. Physiol., 489:767 [1995]). It is contemplated that a similar localization occurs for the human α7 alternative transcripts, containing the novel exons, if translated. However, it is not intended that the present invention be limited to any particular localization of these alternative transcripts.

Antibodies to the cytoplasmic loop of the chick α7, between membrane spanning regions III and IV, have been shown to detect α7 protein in pyramidal cells of rat hippocampus (Dominguez del Toro et al., J. Comp. Neurol., 349:325 [1994]). However, during the development of the present invention, no α-bungarotoxin binding (i.e., indicative of a functional receptor), was observed on the plasma membranes of these cells. Since protein, translated from alternative α7 mRNAs containing D-C-B-A-5-10, would have the epitope used as antigen for cytoplasmic loop antibodies, it is possible that sequestered, but dysfunctional α7 protein internally localized would be detected as well as cell surface protein. The abundance of the D-C-B-A-5-10 alternative transcripts, thus, raises the possibility that they are regulatory for functional expression of α7 nicotinic receptors.

Although the mechanism responsible for the gene duplication is unclear, and an understanding of the mechanism is not necessary in order to use the present invention, two alu repeats were found in the genomic clones. One is located in intron 4,500 bp upstream of exon 5. The second is located in the 3'-end of the gene outside of the poly-adenylation site. Alu repeats are known to have several possible functions, including as either positive or negative enhancers of transcription. In addition, they have also been shown to mediate duplication or deletion of DNA sequences (Schmid, Prog. Nucl. Acid Res., 53:283 [1996]; and Lehrman et al., Cell 48:827 [1987]).

It is clear that the duplicated and expressed sequences involving the human α7 nicotinic receptor gene of the present invention provide the methods and compositions needed for mutation screening in disease. The present invention also provides methods and compositions for treatment (including, but not limited to gene therapy) of deficits in α7 expression and/or function.

The present invention provides methods and compositions needed to determine the control of α7 expression, through the use of the DNA sequences in its promoter region, as well as DNA sequences located at its intron/exon boundaries, and DNA sequences present elsewhere in its introns. In addition, the present invention provides the locations and sequences of newly identified duplicated and additional exons. It is contemplated that these sequences may be involved in pathogenic mutational events. Although the coding sequence of α7 shares some similarities between various animals (e.g., chickens, rodents, and humans), the genomic structure provided in the present invention in the promoter and introns is unique to humans, and could not have been predicted based on the knowledge of the genome structure of any other species.

Furthermore, the coding region alone cannot be used for genetic screening of individuals to identify mutations, because the appropriate primers (e.g., for PCR) are needed from introns positioned outside of the coding region. In addition, the genomic sequence is necessary for the production of cell lines and transgenic animals (i.e., for models useful for the development of therapeutic targets in drug discovery). The present invention provides the needed genomic sequences and primers for genetic screening methods and drug discovery.

III. Treatment and Diagnosis of Schizophrenia and Other Psychoses

The present invention provides methods and compositions for the development and identification of alternative means to diagnose and treat schizophrenia. The methods and compositions of the present invention will find use in the functional assessment of α7 nicotinic receptors in schizophrenic patients, as well as for screening populations for deficits in receptor function. The present invention finds use in genetic screening methods for genetic and parentage counseling, as well as for identification of individuals at risk for developing schizophrenia.

The present invention also provides methods and compositions for modifying α7 nicotinic receptor function. For example, the present invention contemplates the development of genetic therapy methods to correct deficiencies in the receptor structure and/or function, as well as other therapeutic methods to enhance or decrease the function of the receptor, as appropriate for the treatment of any given individual.

It is also contemplated that the present invention will find use in relation to other psychosis. For example, the present invention will find use in the diagnosis and treatment of genetic disorders, in particular those genetic disorders known to have a genetic component associated with chromosome 15, such as Prader-Willi syndrome, Angelman's syndrome, etc., as well as other diseases, such as epilepsy (e.g., juvenile myoclonic epilepsy), breast, and other types of cancers. The present invention also finds use in the diagnosis and treatment of nicotine-dependent illnesses, including, but not limited to, small cell lung carcinoma.

Indeed, it is contemplated that the present invention will find use in the development of antipsychotic drugs targeted to the α7 nicotinic receptor and/or the α7 nicotinic receptor subunit gene. For example, dimethylbenzylidine anabaseine (DMXB-A; [(2–4) Dimethoxy-benzylidene anabaseine hydrochloride]) and its congeners are selectively agonistic at the α7 receptor. During the development of the present invention, an animal model of the deficit observed in schizophrenics was used to show that DMXB-A is effective in repeated doses, whereas the effect of nicotine itself is completely inactivated after one dose. DMXB-A also has significantly less cardiovascular effects than nicotine, consistent with its antagonist effects at α4-β2 nicotinic receptors. Thus, it is contemplated that DMXB-A will find use as an anti-psychotic drug.

In addition to the physiological deficit found in schizophrenics and some of their relatives, similar deficits are also found as state-related changes in other psychotic disorders, including Parkinson's, Alzheimer's, mania and cocaine dependence. In stimulant dependence, neuroleptic antipsychotic drugs have poor patient compliance, possibly due to their anhedonic, catecholamine-blocking effects. Thus, it is contemplated that nicotinic cholinergic therapeutic strategies, such as those developed using the methods and/or compositions of the present invention will be effective against a broad spectrum of clinical indications.

It is further contemplated that the present invention will be used to develop antibodies and other diagnostic reagents. For example, the present invention finds use in the production of peptide antibodies using sequences identified using the present invention.

IV. Transgenic Animals

The present invention provides methods and compositions for production of transgenic animal models of schizophrenia, nicotine-dependent illnesses, and cancer. It is also contemplated that such systems as *Xenopus* oocytes will be used to express human α7 receptors and gene sequences of the present invention.

In preferred embodiments, transgenic mice are generated using microinjection of DNA containing α7 gene sequences into mammalian oocytes. However, equivalent transgenic mice can also be produced by homologous recombination in embryonic stem (ES) cells. Techniques for the isolation, culture, microinjection and implantation of a variety of mammalian oocytes (e.g., murine, porcine, ovine, bovine, etc.) are known to the art.

Two mouse models are provided in the present invention. The first model involves introduction of an intact human α7 gene into the mouse genome by microinjection of a fertilized egg with DNA from the clone containing the full-length nAChR gene described in Example 8. The integrity of the clone in the transgenic mice is examined by PCR amplification, using all of the identified STSs on the clone map. Large flanking DNA sequences are included in this transgene, in order to ensure proper expression of the human α7 gene in the mice. The expression of the human α7 gene in mice is examined by an RNase protection assay designed to specifically detect the human α7 mRNA. This expression pattern coincides with the expression pattern of α7 in human tissues, as analyzed by Northern hybridization. The transgenic mouse model provides animals for determinations of α7 function in nicotine-dependence, nicotine-dependent illnesses, cancers associated with chromosome 15, schizophrenia, and other psychoses. These animals also facilitate the development of drugs and other therapeutics that affect the function of human α7 in vivo.

The second model is exemplified using transgenic mice which contain targeted disruptions of the α7 gene. These animals, termed "knockout" animals, lack the ability to express α7 ("α7 knockouts"). In this model, mice are generated with a deletion specifically in the α7 gene, in order to allow assessment of phenotypic changes. In order to produce the transgenic knockout mice of the present invention, cloned human α7 gene sequences are used to disrupt the α7 gene in such a manner that α7 cannot be produced. In this model, two types of deletions are designed.

The first removes the α7 gene entirely from the germline cells. The second type of deletion is engineered so as to provide control over the specific tissue and developmental stage in which α7 expression is interrupted. In the second model, the viability of the mutated animals is maintained, permitting analysis of the animals' phenotypes (including expression in specific tissues).

DEFINITIONS

To facilitate understanding of the invention, a number of terms are defined below.

The term "α7 gene" (or Alpha-7, or "Alpha-7 gene") refers to the full-length α7 nucleotide sequence. However, it is also intended that the term encompass fragments of the α7 sequence, such as those that encoded by SEQ ID NOS:95–103, as well as other domains within the full-length α7 nucleotide sequence. Furthermore, the terms "Alpha-7 nucleotide sequence" or "Alpha-7 polynucleotide sequence" (or "α7 nucleotide sequence" or "α7 polynucleotide sequence") encompasses DNA, cDNA, and RNA (e.g., mRNA) sequences. In preferred embodiments, the α7 is human α7.

A "variant" of human α7 as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The term "biologically active," as used herein, refers to a protein or other biologically active molecules (e.g., catalytic RNA) having structural, regulatory, or biochemical functions of a naturally occurring molecule. Likewise, "immunologically active" refers to the capability of the natural, recombinant, or synthetic α7, or any oligopeptide or polynucleotide thereof, to induce a specific immune response in appropriate animals or cells and to bind with specific antibodies.

The term "agonist," as used herein, refers to a molecule which, when bound to α7, causes a change in α7, which modulates the activity of α7. Agonists may include proteins, nucleic acids, carbohydrates, or any other molecules which bind or interact with α7.

The terms "antagonist" or "inhibitor," as used herein, refer to a molecule which, when bound to α7, blocks or modulates the biological or immunological activity of α7. Antagonists and inhibitors may include proteins, nucleic acids, carbohydrates, or any other molecules which bind or interact with α7.

The term "modulate," as used herein, refers to a change or an alteration in the biological activity of α7. Modulation may be an increase or a decrease in protein activity, a change in binding characteristics, or any other change in the biological, functional, or immunological properties of α7.

The term "derivative," as used herein, refers to the chemical modification of a nucleic acid encoding α7, or the encoded α7. Illustrative of such modifications would be replacement of hydrogen by an alkyl, acyl, or amino group. A nucleic acid derivative would encode a polypeptide which retains essential biological characteristics of the natural molecule.

The term "gene" refers to a nucleic acid (e.g., DNA) sequence that comprises coding sequences necessary for the production of a polypeptide or precursor (e.g., human α7). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation. The present invention provides DNA sequence of the α7 promoter (SEQ ID NO:101; See, FIG. 8). The present invention also provides DNA sequence for the region located 5' to the human α7 gene (SEQ ID NO:94; See, FIG. 4).

"Peptide nucleic acid," as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al., Anticancer Drug Des. 8:53–63 [1993]).

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al., J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signal mediate the removal of introns from the primary RNA transcript and consist of a splice donor and acceptor site (J. Sambrook et al., Molecular Cloning: A Laboratory Manual, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6–16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), PCR Technology, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. The present invention provides sequences for numerous primers (i.e., SEQ ID NOS:1–8, and 12–83).

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label. The present invention provides sequences for suitable for use as probes (e.g., SEQ ID NO:9–11, as well as the primer sequences described above).

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (See e.g., U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, micro ell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

As used herein, the term "antisense" is used in reference to RNA sequences which are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) or interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "polyA$^+$ RNA" refers to RNA molecules having a stretch of adenine nucleotides at the 3' end. This polyadenine stretch is also referred to as a "poly-A tail." Eukaryotic mRNA molecules contain poly-A tails and are referred to as polyA$^+$ RNA.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a mammalian α7 protein includes, by way of example, such nucleic acid in cells ordinarily expressing an α7 protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and antisense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11(11) on the short arm (p) in the first region (1) in the 5th band (5) in sub-band 5 (0.5). A potion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA which is produced by transcription of genes located on a chromosome (e.g., hnRNA and mRNA) and cDNA copies of the RNA transcribed from the DNA located on a chromosome. Sequences associated with a chromosome may be detected by numerous techniques including probing of Southern and Northern blots and in situ hybridization to RNA, DNA or metaphase chromosomes with probes containing sequences homologous to the nucleic acids in the above listed preparations.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein the term "purified" or "to purify" refers to the removal of contaminants from a sample. For example, anti-α7 antibodies are purified by removal of contaminating non-immunoglobulin proteins; they are also purified by the removal of immunoglobulin that does not bind α7. The removal of non-immunoglobulin proteins and/or the removal of immunoglobulins that do not bind α7 results in an increase in the percent of α7-reactive immunoglobulins in the sample. In another example, recombinant α7 polypeptides are expressed in bacterial host cells and the polypeptides are purified by the removal of host cell proteins; the percent of recombinant α7 polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (i.e., mouse or human α7 and fragments thereof) joined to an exogenous protein fragment (the fusion partner which consists of a non-α7 protein). The fusion partner may enhance solubility of the α7 protein as expressed in a host cell, may provide an affinity tag to allow purification of the recombinant fusion protein from the host cell or culture supernatant, or both. If desired, the fusion protein may be removed from the protein of interest (i.e., α7 protein or fragments thereof) by a variety of enzymatic or chemical means known to the art.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, J. et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The present invention also contemplates "non-human animals" comprising any non-human animal capable of overexpressing α7 mRNA and/or proteins. Such non-human animals include vertebrates such as rodents, non-human primates, ovines, bovines, ruminants, lagomorphs, porcines, caprines, equines, canines, felines, aves, etc. Preferred non-human animals are selected from the order Rodentia, most preferably mice. The term "order Rodentia" refers to rodents (i.e., placental mamunals [Class Euthria] which include the family Muridae (rats and mice).

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals." A transgenic animal is an animal whose genome has been altered by the introduction of a transgene.

The term "transgene" as used herein refers to a foreign gene that is placed into an organism by introducing the foreign gene into newly fertilized eggs or early embryos. The term "foreign gene" refers to any nucleic acid (e.g., gene sequence) which is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the α7 mRNA-specific signal observed on Northern blots). The amount of mRNA present in the band corresponding in size to the correctly spliced α7 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "selectable marker" refers to the use of a gene which encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt) gene which is used in conjunction with hprf cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp.16.9–16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of cancer.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of α7 instability or inactivity in animals.

A "composition comprising a given polynucleotide sequence" as used herein refers broadly to any composition containing the given polynucleotide sequence. The composition may comprise an aqueous solution. Compositions comprising polynucleotide sequences encoding human α7 or fragments thereof may be employed as hybridization probes. In this case, the human α7-encoding polynucleotide sequences are typically employed in an aqueous solution containing salts (e.g., NaCl), detergents (e.g., SDS) and other components (e.g., Denhardt's solution, dry milk, salmon sperm DNA, etc.).

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "test α7" refers to a sample suspected of containing α7. The concentration of α7 in the test sample is determined by various means, and may be compared with a "quantitated amount of α7" (i.e., a positive control sample containing a known amount of α7), in order to determine whether the concentration of test α7 in the sample is within the range usually found within samples from wild-type organisms. Thus, comparison of the positive control with the test sample allows the determination to be made whether a particular individual produces a "normal" amount of α7, is deficient in production of α7, or produces a concentration of α7 that is greater than normal. It is intended that such test methods also contain "negative" controls (i.e., samples that are known to contain no α7). Furthermore, it is intended that the testing be conducted using the α7 gene, α7 mRNA, and/or α7 protein (or polypeptides), or fragments of any of these.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: nAChR (nicotinic acetylcholine receptor); ° C. (degrees Centigrade); rpm (revolutions per minute); BSA (bovine serum albumin); $H_2O$ (water); HCl (hydrochloric acid); aa (amino acid); bp (base pair); kb or kbp (kilobase pair); Mb (megabase pair); kD (kilodaltons); gm or g (grams); μg (micrograms); mg (milligrams); ng (nanograms); μl (microliters); ml (milliliters); mm (millimeters); nm (nanometers); μm (micrometer); M (molar); mM (millimolar); μM (micromolar); nM (nanomolar); pM (picomolar); U or u (units); V (volts); MW (molecular weight); sec (seconds); min(s) (minute/minutes); hr(s) (hour/hours); dNTP (deoxynucleotide); $MgCl_2$ (magnesium chloride); NaCl (sodium chloride); KCl (potassium chloride); DTT (dithiotreitol); DMSO (dimethyl sulfoxide); NaOH (sodium hydroxide); 3'UT (3'-untranslated region); $OD_{280}$(optical density at 280 nm); $OD_{600}$(optical density at 600 nm); EST (expressed sequence tag); PAGE (polyacrylamide gel electrophoresis); PBS (phosphate buffered saline [150 mM NaCl, 10 mM sodium phosphate buffer, pH 7.2]); PCR (polymerase chain reaction); DMEM (Dulbecco's Modified Eagle Medium); PEG (polyethylene glycol); PMSF (phenylmethylsulfonyl fluoride); RT-PCR (reverse transcription PCR); SDS (sodium dodecyl sulfate); SSC (saline-sodium citrate buffer); Tris (tris(hydroxymethyl)aminomethane); w/v (weight to volume); v/v (volume to volume); YAC (yeast artificial chromosome); BAC (bacterial artificial chromosome); PAC (P1 artificial chromosome); RACE (Rapid Amplification of cDNA Ends); TAFE (Transverse Alternating Field Electrophoresis); lod (maximum logarithm of the odds); STS (sequence-tagged site); Beckman (Beckman Instruments, Inc., Fullerton, Calif.); Amersham (Amersham Life Science, Inc. Arlington Heights, Ill.); Qiagen (Qiagen Inc., Santa Clarita, Calif.); Genome Systems (Genome Systems, St. Louis, Mo., USA); ICN (ICN Pharmaceuticals, Inc., Costa Mesa, Calif.); Amicon (Amicon, Inc., Beverly, Mass.); NCBI (National Center for Biotechnology Information, Bethesda, Md.); ATCC (American Type Culture Collection, Rockville, Md.); Research Genetics (Research Genetics, Huntsville, Ala.); Pharmacia (Pharmacia and Upjohn Diagnostics, Kalamazoo, Mich.); Boehringer-Mannheim (Boehringer-Mannheim, Indianapolis, Ind.); National Biosciences (National Biosciences, Inc., Plymouth Minn.); MJ Research (MJ Research, Watertown, Mass.); Perkin-Elmer (Perkin-Elmer, Foster City, Calif.); BioRad (BioRad, Richmond, Calif.); Clontech (CLONTECH Laboratories, Palo Alto, Calif.); Gibco, GIBCO BRL, or Gibco BRL (Life Technologies, Inc., Gaithersburg, Md.); Gene Codes (Gene Codes Corporation, Ann Arbor, Mich.); Invitrogen (Invitrogen Corp., San Deigo, Calif.); Kodak (Eastman Kodak Co., New Haven, Conn.); Promega (Promega, Corp., Madison, Wis.); New England Biolabs (New England Biolabs, Inc., Beverly, Mass.); Novagen (Novagen, Inc., Madison, Wis.); Pharmacia (Pharmacia, Inc., Piscataway, N.J.); Schleicher & Schuell (Schleicher and Schuell, Inc., Keene, N.H.); Sigma (Sigma Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Whatman (Whatman LabSales, Hillsboro, Oreg.); Bethyl Laboratories (Bethyl Laboratories, Montgomery, Tex.); Ambion (Ambion, Inc., Austin, Tex.); and Zeiss (Carl Zeiss, Inc., Thornwood, N.Y.).

Unless otherwise indicated, all restriction enzymes were obtained from New England BioLabs and were used according to the manufacturer's instructions.

EXAMPLE 1

Samples

Samples were obtained from various normal individuals for use as controls in the Examples described below. To prepare these samples, blood was drawn from normal subjects, seen in the Denver Schizophrenia Center. Of the 43 subjects used for the polymorphism analysis, 22 were female and 21 were male. There were 38 Caucasians, 2 Blacks, 1 Asian and 2 Hispanics. None of the subjects had a history of mental illness nor a family history of mental illness.

In addition to the "normal" samples, pedigrees were selected for presence of at least two cases of schizophrenia in a nuclear family. Two psychiatrists made clinical diagnoses of schizophrenia, chronic type, blind to pedigree and genetic information, using Research Diagnostic Criteria (Spitzer et al, Arch. Gen. Psychiat., 35:773 [1978]; and Endicott and Spitzer, Arch. Gen. Psychiat., 35:837 [1978]). Nine families with 104 members were studied (i.e., nine pedigrees containing individuals diagnosed with schizophrenia were analyzed). All subjects gave written informed consent. Blood was also drawn from these individuals for DNA analysis.

DNA was extracted from blood samples as described by Miller et al., (Miller et al., Nuc. Acids. Res., 16:1215 [1988]) with one additional step. Briefly, red blood cells were lysed by incubating 10–15 ml of anticoagulated blood at 4° C. for 10 minutes in 40 ml blood cell lysis solution (BCL) (BCL contains 0.3 M sucrose, 0.01 M Tris HCl pH 7.5, 0.005 M $MgCl_2$ and 1% Triton X-100) with occasional rocking to mix. The cells were then centrifuged at 850×g at 4° C. for 15 minutes. The pellet was resuspended by repeated pipetting with a 1 ml wide bore glass pipet in 30 ml BCL (4° C.) and centrifuged as before.

DNA was then extracted from the pellet as described by Miller et al., (Miller et al., Nucl. Acids. Res., 16:1215 [1988]). Briefly, the pellet was resuspended as before in 3 ml Nuclei Lysis buffer (NL) (NL contains 0.075 M NaCl, and 0.024 M EDTA pH 8.0). Then, 200 μl of 10% SDS, 440 μl of digest diluent (1% SDS, 2 mM Na$_2$EDTA), and 60 μl of Proteinase K (20 mg/ml stock) were then added to the suspension. The suspension was then incubated at 37° C. for 16–20 hours with gentle mixing by inversion. Following this digestion, 1 ml of saturated (approx. 6 M) NaCl was added and then the suspension briefly (15 seconds) was vigorously shaken. The suspension was then centrifuged at 1340×g at room temperature for 15 minutes. The supernatant was transferred to a new tube, leaving the pellet at the bottom of the previous tube undisturbed. Exactly 2 volumes of absolute ethanol were added. The tube was then inverted several times until the DNA pellet was visible and floated to the top. The pellet was then transferred to a new tube. The pellet was resuspended in 0.67 ml TE pH 8 (10 mM Tris, 1 mM EDTA) by gently mixing on a roller drum for 3–5 days at 37° C.

In addition to the samples described above, a chromosome 15 somatic cell hybrid line, R379-2B2 generously provided by Dr. Carol Jones (The Eleanor Roosevelt Institute for Cancer Research, Denver, Colo.), was also used. This cell line was cultured in Ham's F12, supplemented with 5% fetal bovine serum and 10 μg/ml gentamicin.

Another cell line, the human neuroblastoma cell line, SH-SY5Y (Biedler et al., Cancer Res., 38:3751 [1978]), was obtained from Dr. June Biedler (Memorial Sloan-Kettering Cancer Center, New York, N.Y.), and grown in DMEM/Ham's F12 (1:1 ratio, supplemented with 15% fetal bovine serum, 4 mM glutamine, and 10 μg/ml gentamicin.

EXAMPLE 2

Genomic Clone Isolation

In this Example, YAC clones were identified by PCR screening of two genomic libraries, namely the St. Louis YAC library (Burke et al., Science 236:806 [1987]) and the CEPH YAC Library 3 (Albertsen et al., Proc. Natl. Acad. Sci., 87:4256 [1990]), using α7 cDNA specific primers and methods known in the art (See e.g., Brownstein et al., Science 244:1348 [1989]; Chumakov et al., Nature 359:380 [1992]; and Dracopoli et al., Current Protocols in Human Genetics, John Wiley & Sons, Inc., New York, N.Y. [1994])

Additional YACs, positive for loci in the α7 nAChR region were identified initially by using Infoclone on the CEPH/Genethon Integrated Map (www.cephb.fr/ceph-genethon-map.html). Loci on the YAC contig were verified by PCR screening with either α7 primer sets or primer sets for the specific polymorphic markers listed in the YAC contig (See, FIG. 6), which are available from either the CEPH database or GenBank. The PCR conditions were 94° C. for 2 minutes, 1 cycle; followed by 35 cycles of 94° C. for 30 seconds, 55° C. for 30 seconds, and then 72° C. for 30 seconds, followed by 72° C. for 7 minutes-1 cycle. These PCR conditions were used for all PCR amplifications, unless otherwise indicated.

In addition, α7-specific primer sets were used to identify the two PAC clones 64a1 and 25919. A Research Genetics BAC library was screened with α7 coding region primers by PCR to identify the BAC clone 467o18. The BAC library purchased from Research Genetics was a "pooled DNA" library, with each hit-positive PCR product of correct size being indicative of a location on a subsequent plate of pools. A hit on this plate gave an address to yet another plate, where the clone of interest was found. These "BAC clone" plates are maintained by Research Genetics. When the positive PCR reactions produced a final plate address in the clone library, that clone was ordered from Research Genetics. The PCR conditions and primers were as described herein (the primers used are shown in Tables 1 and 2). The two PAC clones (64a1 and 25919) were identified using the following PCR primers.

The primers used in these experiments were:

| | | |
|---|---|---|
| sense | TCCTGATGTCGGCTCCCAACT | (SEQ ID NO:1) |
| antisense | GGTACGGATGTGCCAAGGATA | (SEQ ID NO:2) |
| sense | TTTGGGGGTGCTAATCCAGGA | (SEQ ID NO:3) |
| antisense | TTGTTTTCCTTCCACCAGTCA | (SEQ ID NO:4) |
| sense | CTCGCTGCAGCTCCGGGACTCA | (SEQ ID NO:5) |
| antisense | GGAGGCTCAGGGAGAAGTAG | (SEQ ID NO:6) |

The first two sets of primers were used to amplify the 3' untranslated region of the gene and the third primer set was used to amplify the first and second exons of the gene with the intervening intron 1 sequence. All PCR reactions were optimized in a Perkin Elmer 480 PCR using normal human DNA and cDNA. Conditions were as follows for the control reactions in the 3' sets: 96° C. for two min, then 35 cycles of 96° C. for 30 sec, 56° C. for 30 sec, 72° C. for 1 min, and cool to 4° C., using 4 mM MgCl$_2$ and 10% DMSO. The 5' PCR set was used in 1.5 mM MgCl$_2$ and 10% DMSO with the following conditions: 96° C. for 3 min, then cycles 1–6 were 94° C. for 1 min, 68° C.–58° C. for 1 min (dropping from 68° C. to 58° C., by 2° C. increments each cycle), 72° C. for 1 min, followed by 30 cycles of 94° C. for 1 min, 58° C. for 1 min, 72° C. for 1 min, then a 4 min extension at 4° C., followed by chilling at 4° C.

In these experiments, a genomic clone for the human α7 nicotinic receptor was identified. A YAC designated as b134h10 of approximately 250 kb, was isolated from the St. Louis YAC library. A Southern blot comparison of YAC b134h10 with human genomic DNA indicated that it contained the full length α7 nAChR gene. This YAC was used to isolate a polymorphic marker, D 15S1360, as described in greater detail below.

The polymorphic marker D15S1360, a complex microsatellite with four alleles, was isolated from a YAC containing the α7 nicotinic receptor gene. The Genbank sequence for rat α7 (#M85273) was used to design primers to the conserved regions of the α7 coding sequence. These primers were then used to PCR amplify normal human hippocampal cDNA obtained from a normal brain postmortem. The products were sequenced by Automated dye-terminator chemistry (as described in Example 5). The human sequence in transmembrane regions III and IV was then used to design PCR primers. These primers were: 5'-CTC CAG GAT CTT GGC CAA GTC-3' (antisense strand; SEQ ID NO:7 or SEQ ID NO:48), and 5'-AGA TGC CCA AGT GGA CCA GAG-3' (sense strand; SEQ ID NO:8).

The PCR reactions were conducted with 2 mM MgCl$_2$ and 10% DMSO, in a Perkin-Elmer 4800 using the following cycles: 94° C. for 2 min, then 5 cycles of 94° C. for 1 min, 56° C. for 30 sec, 72° C. for 1 min, then 35 cycles 94° C. for 1 min, 54° C. for 30 sec, 72° C. for 1 min, and cooling at 4° C. The product was reamplified with primers extended to contain a sense Xba and antisense Bam site. The products were cut and ligated into a BlueScript SK– vector. Sequence of the probe was confirmed by automated dye-primer sequencing. Subsequent PCR based screening of the original YAC clones were based on the above primers and conditions, substituting YAC DNA for hippocampal cDNA as the template.

The PCR fragment (i.e., the probe) was sequenced and human primers were designed to generate a 338 bp product, which was cloned into pBluescript SK(–). The sequence of the 338 bp probe was: AGATGCCCAAGTGGACCA-GAGTCATCCTTCTGAACTGGTGCGCGTGGTTCCT GCGAATGAAGAGGCCCGGGGAGGACAAG-GTGCGCCCGGCCTGCCAGCACAA GCAGCGGCGCT-GCAGCCTGGCCAGTGTGGAGATGAGCGC-CGTGGGCCCGCCG CCCGCCAGCAACGGGAACCTGCTGTA-CATCGGCTTCCGCGGCCTGGACGGCG TGCACTGT-GTCCCGACCCCCGACTCTGGGGTAGTGT-GTGGCCGCATGGCCTGC TCCCCACGCACGATGAGCACCTCCTG-CACGGCGGGCAACCCCCCGAGGGGG ACCCG-GACTTGGCCAAGATCCTGGA (SEQ ID NO:9).

This probe was used to isolate a human α7 cDNA (GenBank #U40583). The Washington University human YAC library was screened with the same primers. Two clones were isolated, B132H10 (150 kbp) and B134H10 (300 kbp), on the TAFE (Beckman) gel system, using the procedures recommended by the manufacturer.

A sub-library of B 134H 10 was prepared in the γZAP phagemid vector by complete MboI digestion of the intact YAC DNA in a low-melt agarose plug. The DNA was extracted and ligated into BamH1 digested and phosphatased vector, transformed into XL 1 Blue-(MRF'), and screened with a $(CA)_{16}$ (SEQ ID NO: 10) oligonucleotide. One clone contained a microsatellite $[(CA)_5 T(CA)_{12} TA (CA)_5 C(CA)_3]$ (SEQ ID NO:11), which mapped to chromosome 15 (Human/Rodent Hybrid Mapping Panel #1, Coriell, Camden N.J.). Flanking primers amplified seven additional alleles (97, 107, 109, 111, 113, 115, and 117 bp). The primers used were 5'-GATCTTTGGTAGAAGC-3' (SEQ ID NO:12), and 5'-ACCACCACTACCATACAGAC-3' (SEQ ID NO: 13). Allele frequencies (0.006, 0.006, 0.006, 0.516, 0.370, 0.090, and 0.006; heterozygosity 0.57) were estimated from individuals marrying into the pedigrees described in Example 1. Primer sets used for mapping α7 exons to YAC clones are listed in Table 1, below. Primers used for mapping STS/dinucleotide repeat markers to YAC clones were obtained from Genbank, and are listed in Table 2. In these Tables, and unless otherwise indicated, all DNA sequences are shown in 5' to 3' orientation.

TABLE 1

Primer Sets Used to Amplify Exon and Flanking Intron Sequence from Human Alpha-7 Nicotinic Receptor

| Sequence Amplified and Primer Number | Sequence | SEQ ID NO: |
|---|---|---|
| Promoter #1234 | CAAAGAACGCAAGGGAGAGGT | SEQ ID NO:14 |
| Promoter #1235 | CGGCTCGCGCGCCTTTAAGGA | SEQ ID NO:15 |
| Exon 1 #1331 or #1236 | GGGCTCGTCACGTGGAAAAGC | SEQ ID NO:16 |

TABLE 1-continued

Primer Sets Used to Amplify Exon and Flanking Intron Sequence from Human Alpha-7 Nicotinic Receptor

| Sequence Amplified and Primer Number | Sequence | SEQ ID NO: |
|---|---|---|
| Exon 1 #1233 | GGATCCCACGGAGGAGTGGAG | SEQ ID NO:17 |
| Exon 2 #1198 | CCTGCCCGGGTCTTCTCTCCT | SEQ ID NO:18 |
| Exon 2 #1138 | AACTAGAGTGCCCCAGCCGAGCT | SEQ ID NO:19 |
| Exon 3 #1475 | AACAACGCTCTCGACAGTCAGATC | SEQ ID NO:20 |
| Exon 3 #1476 | AAGATCTTGCAGCCCATGGGAG | SEQ ID NO:21 |
| Exon 4 #1368 | GGAATTCTCTTTGGTTTTGCAC | SEQ ID NO:22 |
| Exon 4 #1369 | ACATATCCAGCATCTCTGTGA | SEQ ID NO:23 |
| Exon 5 #1218 | TCATGCAGTCCTTTTCCTGTTTC | SEQ ID NO:24 |
| Exon 5 #1142 | CTCGCTTCAGTTTTCTAACATGG | SEQ ID NO:25 |
| Exon 6 #1124 | GGAACTGCTGTGTATTTTCAGC | SEQ ID NO:26 |
| Exon 6 #1144 | TTAAAGCTTGCCCAGGAATAGG | SEQ ID NO:27 |
| Exon 7 #1143 | GCTTGTGTGTGGTATACACATTG | SEQ ID NO:28 |
| Exon 7 #1126 | TCCAGAGCTGATCTCAGCAGAAG | SEQ ID NO:29 |
| Exon 8 #1125 | GCCCCTCGTTAGACAGAATTGAG | SEQ ID NO:30 |
| Exon 8 #1145 | CTGGGCACACTCTAACCCTAACC | SEQ ID NO:31 |
| Exon 9 #1146 | TGTGACGTGCAGTGCCACAGGA | SEQ ID NO:32 |
| Exon 9 #1127 | AAAACCCTAGGAGGAGCCTCCTT | SEQ ID NO:33 |
| Exon 10 #1128 | GATCAGCCCGTTTCCGCCTCA | SEQ ID NO:34 |
| Exon 10 #589 | GGTACGGATGTGCCAAGGATA | SEQ ID NO:35 |
| Exon A #1516 | GGACTCTGCTTTTGATAAATATGTATG | SEQ ID NO:36 |
| Exon A #1517 | TTGCTGTCACTTTCTGTGTTTCAT | SEQ ID NO:37 |
| Exon B #1283 | GACAATCCAAAGGTGCAGAAAGC | SEQ ID NO:38 |
| Exon B #1538 | TTCGTATCTGTATACAGACAGTC | SEQ ID NO:39 |
| Exon C #1567 | CCTCAGCATCATATTAGTTCAGTG | SEQ ID NO:40 |
| Exon C #1572 | GCGGACAAGAGAAACAGGAAAG | SEQ ID NO:41 |
| Exon D #1534 | GGCAGTGGTGCTGTTGCCCTT | SEQ ID NO:42 |
| Exon D #1568 | TTTCTCCTGGGACTCTGGGCAC | SEQ ID NO:43 |

TABLE 2

STS/Dinucleotide Repeat Markers

| Marker | Genbank Accession # |
|---|---|
| D15S942 | G04933 |
| D15S1043 | Z51622 |
| D15S165 | Z17271 |
| D15S1031 | Z51346 |
| D15S1010 | Z53401 |
| D15S144 | Z23286 |
| D15S1007 | Z53384 |

TABLE 2-continued

STS/Dinucleotide Repeat Markers

| Marker | Genbank Accession # |
|---|---|
| D15S995 | Z53051 |
| D15S1040 | Z51533 |

Additionally, genomic P1 artificial chromosome (PAC) clones for α7 were obtained from Genome Systems. PAC-64-A1 is 120 kbp long and contains both D15S1360 and the 5' end of the coding region. L76630 was localized in a genomic fragment containing the α7 nicotinic receptor gene (CHRNA7), isolated from a human genomic library (Stratagene), by screening with a human α7 cDNA clone (HP411).

A 6 kbp EcoRI genomic fragment was identified, partially sequenced, and found to include a CA dinucleotide repeat 3' of the last exon (GenBank #L76630). Flanking primers amplified 3 alleles (180, 178, 176 bp); allele frequencies were 0.06, 0.62, 0.32, with heterozygosity 0.51.

PCR was performed with 1.5 mM MgCl$_2$: 94° C. for 5 min, 20 cycles of 94° C. for 1 min, 56° C. for 2 min, 72° C. for 1 min and 72° C. for 5 min. The two polymorphisms were genetically mapped in 96 individuals from 6 reference families (Centre d'Etude du Polymorphisme Humain). These reference families were selected because they have three generations of individuals available for genotyping. Their DNA is available for genetic localization of markers, but their identities are confidential.

EXAMPLE 3

Generation of Templates for Sequence Analysis of the Intron/Exon Borders.

In this Example, extra-long PCR (XLPCR), originally described by Barnes (Barnes, Proc. Natl. Acad. Sci., 91:2216 [1994]), was conducted using rTth polymerase with the Perkin Elmer XL/PCR kit (Perkin-Elmer), on a PTC 200 (MJ Research) thermal cycler with the following conditions: 94° C., 1 min, 1 cycle; 94° C., 15 sec/68° C., 10 min, 16 cycles; 94° C., 15 sec/68° C., 10 min 15 sec, 12 cycles; 72° C., 10 min, 1 cycle. Enzyme, primer concentration, and dNTP concentrations were as recommended by the manufacturer. A sublibrary of YAC b134H10 was constructed by EcoRI digestion and subcloning into Bluescript (SK−), (Stratagene), for splice junction determination on the larger introns.

To characterize the promoter and borders around exon 1 and 2, an EcoRI and KpnI sublibrary of PAC 25919 was constructed in Bluescript (SK−). A 2.9 kb clone containing exon 1, and a 5 kb clone containing exon 2 were identified by screening the PAC sublibrary by hybridization with an α7 cDNA subclone containing 90 bp of 5' untranslated sequence, exon 1 and exon 2.

Tentative exon borders were deduced based upon the organization of the α7 nAChR gene in the chick (Couturier et at, Neuron 5:847 [1990]). Oligonucleotide primers, as shown in the table below, were designed from within the predicted exons that would amplify across the putative introns using extra-long PCR (XLPCR) with both genomic DNA and YAC b134h10 DNA. The exon primers used were as follows. For exon 5 to exon 10, the primers used were Primer #661 (TGACGCCACATCCACACTAA)(SEQ ID NO:44); and Primer #591 (TTGTTTCCTTCCACCAGTCA)(SEQ ID NO:45). These primers amplify introns 5,6,7,8, and 9, with an approximate size of 14 kb. For exon 3 to exon 4, the primers used were Primer #1019 (CCAAGTTTTAACCACCAACATTTGG) (SEQ ID NO:46); and Primer #1020 (TCCCCGCGGAAGAATGTCTGGTTTCCAAATCTG) (SEQ ID NO:47). These primers amplify intron 3, with an approximate size of 8 kb.

The majority of intron-exon borders were determined from sequencing the XLPCR products. XLPCR products were not generated between exons 2 and 3 and between exons 4 and 5, suggesting that these introns are large. Preliminary Southern blot data suggested that both are >25 kb. The intron 2 acceptor border, and the intron 4 donor and acceptor borders were determined after sequencing EcoRI subclones derived from YAC b134h10. The intron 2 donor was determined from sequencing a KpnI/EcoRI fragment, subcloned from PAC 25919. Exon/intron border sequence and approximate lengths for introns and exons are summarized in FIG. 1. All of the identified intron-exon borders are consistent with 5' donor and 3' acceptor RNA splice site consensus sequences.

The organization of the human α7 nAChR gene was found to be identical to that found in chick with respect to number and size of exons. A signal peptide sequence predicted by homology with the rat α7 and muscle α1 coding sequences (See e.g., Séguéla et al., J. Neurosci., 13:596 [1993]; Conti-Tronconi et al., Proc. Natl. Acad. Sci. 82:5208 [1985]; and von Heijne, Nuc. Acids Res., 14:4683 [1986]) was found to be encoded by exon 1. Putative glycosylation sites (See e.g., Séguéla et al, supra; Schoepfer et al., Neuron 5:35 [1990]) were found in exons 2, 4 and 5. Cysteine residues that form a putative disulfide bridge (Galzi et al., Ann. Rev. Pharmacol., 31:37 [1991]) were found to be encoded by exon 6. The vicinal cysteines at the acetylcholine (ACh) binding site, the α-bungarotoxin binding site, and membrane spanning region I, are all coded by exon 7. Membrane spanning regions II and III, as in the rat, were found to be coded for by exons 8 and 9 respectively, and membrane spanning region IV was found to be encoded by exon 10.

The putative promoter, and the borders for exons 1 and 2 were determined from sequencing KpnI and EcoRI subclones derived from PAC 25919, which contains exons 1–3 and sequences 5' of the coding region. A 2.9 kb EcoRI-KpnI fragment contained 2.6 kb of the region 5' of exon 1, exon 1 and 200 bp of intron 1. Sequence analysis indicated that 392 bp of the 5' region (GenBank #AFO29837), shown in FIG. 4, is 77% GC rich and lacks a consensus TATA box sequence. In this Figure, the nucleotides are numbered relative to the ATG translation initiation site (indicated with Met); the coding sequence is indicated in bold. Consensus AP-2, Spl, and CREB sequences are shown in boxes. Alignment of the chick (Matter-Sadzinski et al., EMBO J., 11:4529 [1992]) and human promoter sequences indicate they share only 52.9% homology. However, consensus Spl, and AP-2 transcription factor binding sites are present in both human and chick α7 promoters at approximately the same location, relative to the start of translation (Matter-Sadzinski et al., supra). A CREB consensus binding sequence is present in the human promoter, but is not found in the chick.

The primers listed in Table 1 provide a means to obtain sequence information from genomic DNA. Using sequencing techniques standard in the art (e.g., including, but not limited to standard dideoxy sequencing, chain termination sequencing using Taq DNA polymerase or other thermostable polymerases, and automated processes that use these and other technologies), the sequences near the intron and exon junctions can be obtained. Such primers have been successfully used to obtain sequence information from blood samples obtained from schizophrenic patients (i.e., samples obtained as described in Example 1). Sequence obtained from this portion of the chromosome also finds use in providing linkage signal for other nicotine-dependent illnesses including, but not limited to, small cell lung cancer and juvenile myoclonic epilepsy. These sequences are then analyzed to determine if they contain pathogenic mutations that alter gene function by changing the amino acid coding, or by altering gene expression or response to promoter molecules, or by introducing variations in gene splicing. These mutant sequences are also expressed in transgenic cells in culture or in transgenic mice or in frog oocytes, to determine if they indeed cause altered gene function that produces heritable human illnesses such as schizophrenia.

EXAMPLE 4

Identification of Expressed Sequence Tagged cDNAs

In this Example, expressed sequence tagged (EST) cDNA clones were identified in the EST Database at the National Center for Biotechnology Information (NCBI), Bethesda, Md., by BLAST homology searches using α7 cDNA specific sequences. Two (EST 3952 and EST 52861) were purchased from Research Genetics and sequenced bi-directionally as described in Example 5. Contigs were constructed using Sequencher software (Gene Codes).

EXAMPLE 5

Sequence Analyses and Restriction Mapping

In this Example, sequences were determined using standard sequencing kits and automated sequencing. In addition, genomic DNA probed with portions of α7 cDNA was used to order HindIII restriction fragments.
Hand Sequencing PCR product for hand sequencing was prepared using the Exonuclease I-Shrimp Alkaline Phosphatase reagent pack (Amersham), per the manufacturer's directions. Sequencing was done using Thermo Sequenase Radiolabeled Terminator Cycle Sequencing Kit from Amersham. The manufacturer's recommended component concentrations were used with 10 ng of template per 250 bp product per reaction. Reactions were run on a BioRad Sequi-Gene GT sequencing system (BioRad), using a 6% acrylamide/bisacrylamide (19:1) gel.
Automated Sequencing Plasmids to be sequenced were colony purified, using a Qiagen kit (Qiagen). PCR products from PACS, BACs, and YACs were gel purified using a Qiagen PCR product gel extraction protocol. Automated sequencing (ABI 373 or 377, Perkin Elmer) was conducted using Perkin Elmer ABI Dye Terminator or M13 Dye Primer kits, following manufacturer's protocols. Sequencing was organized into contigs using the Sequencher program (Gene Codes). All sequencing was bi-directional.
Restriction Endonuclease Mapping Southern analysis of genomic DNA probed with portions of α7 cDNA was used to order HindIII restriction fragments (Dracopoli et al., supra). DNA was transferred to Hybond N+, and hybridized at 40° C. in 5x Denharts (0.5% SDS, 6xSSC and 50% formamide), then washed twice in 0.1% SDS and 0.1xSSC at 65° C. for 10 minutes.

EXAMPLE 6

Large Insert Clone Contig

Total yeast DNA was isolated from YAC-bearing yeast using a spheroplast method (Dracopoli et al, supra). Loci in and around the α7 region were PCR amplified with loci specific primers (i.e., primers shown in Table 2, as well as primers for D15S1360 described in Example 2). PCR was performed with 1.5 mM MgCl$_2$:94° C. for 5 min, 20 cycles of 94° C. for 1 min, 56° C. for 2 min, 72° C. for 1 min and 72° C. for 5 min.

Mapping of specific exons was performed using the primers listed in Table 1 and the PCR conditions were 94° C. for 2 minutes, 1 cycle; followed by 35 cycles of 94° C. for 30 seconds, 55° C. for 30 seconds, and then 72° C. for 30 seconds, followed by 72° C. for 7 minutes-1 cycle.

Specific amplification was confirmed by sizing the products on agarose gel. PCR products from α7 exons were excised from the gel, Qiagen extracted (Qiagen), and sequenced as described in Example 5.

Additional large insert genomic clones were isolated by PCR screening with α7 specific primers (Chumakov et al., supra). YACs 953g6, 948a10, 853b12, and 969b11 were isolated from the CEPH YAC Library 3. PAC clones 64a1 and 25919 were identified by Genome Systems and BAC 467o18 was identified in a BAC library purchased from Research Genetics.

A tentative YAC contig was designed from markers in the YACs and information in the CEPH/Genathon Database. YACs providing linkage between the full-length and duplicated α7 gene sequences, YACs 895f6, 776a12, 791e6, 811b6, 859c11, 801e1, 810f11, 966a4, 764f8, and 822g2, were obtained from Research Genetics. The contig, shown in FIG. 5, was verified by PCR and sequencing of either α7 sequence or published marker sequence. Loci from the 15q13-14 region were assigned to YACs, BACs, and PACs. The results confirmed the presence of markers previously assigned by Genethon (Human Genome Research Center; a publicly accessible database that maintains human genome linkage information). As indicated in FIG. 5, two allele sizes for the L76630 loci were identified, suggesting that YAC 969B11 spans both α7 nAChr loci.

Exons 5–10 of the α7 nAChR gene and the polymorphic marker L76630 map to two distinct regions of the contig, suggesting a partial gene duplication. The distal, and full-length, α7 nAChR gene maps close to D15S1360, as indicated by two PAC clones (64a1 and 25919) and one BAC clone (467o18). Both of these PACs, approximately 120 kb in size, contain the marker D15S1360 which was used to demonstrate linkage of this region at 15q14 to a schizophrenic trait. Physical mapping of the α7 gene <120 kb from the linkage marker suggested that the α7 micotinic receptor gene is an excellent candidate gene for this trait. The proximal duplicated exon sequences 5–10 of the α7 nAChR gene map between D15S 1043 and D15S165. The order of loci was determined to be D15S942, D15S1043, followed by the duplicated sequences L76630, exon 10, exon 9, exon 8, exon 7, exon 6, and exon 5, and then D15S165 and D15S1031. The closest marker flanking the 3' end of the α7 nAChR gene could not be established and is either D15S1031 or D15S1010. Thus, the full-length gene with the 3'-end closest to D15S1031 has been tentatively oriented, based on the confirmed orientation of the duplicated sequences.

In order to determine if sequence differences were present that might distinguish duplicated exons 5–10 from the full-length gene, PCR products were generated and sequenced from 11 of the genomic YAC clones in the contig. Of these 11 clones, two (948a10 and 853b12) clearly mapped to the duplicated region between D15S1043 and D15S165, and eight mapped to the full-length α7 nAChR gene region near D15S1360. All of the α7 exons were found to be present in YACs 776a12, 791e6, 811b6, 953g6, b134h10, 859c11, 810f11 and 801e1. YAC 948a10 contained only exons 5–10, and 853b12, 6–10, while YAC 969b1 appeared to contain both loci. This YAC is 1.03 Mb in size (FIG. 5), suggesting that the full-length α7 gene and duplicated sequences are not more than 1 Mb apart.

Sequence variants found in DNA from duplicated and full-length genomic α7 sequences are shown in FIG. 2. In exon 6, a 2 bp deletion was identified at bases 497–498 (TG) in clones from the duplicated region, which results in a frame shift in the coding sequence and the insertion of a stop codon within the exon. Additional sequence variants were found at bases 654, 793, 1269 and 1335 of the coding region. These are conservative base changes that do not change an amino acid. The polymorphic marker, L76630 is also duplicated as evidenced by the presence of a different number of CG repeats in the 3'UT of the full length α7 gene and the 3' sequences following exon 10 in the duplicated sequences. YAC 969b11, which contains both full length and duplicated sequences also has two copies of L76630 as does a chromosome 15 hybrid, R379-2B2 (FIG. 2).

EXAMPLE 7

RACE Analysis

In this Example, amino terminal clones for the human α7 subunit were obtained by 5' RACE (i.e., Rapid Amplification of cDNA Ends) (Frohman, Amplifications 5:11 [1990]), using a kit from Gibco-BRL, with some modifications. Although some of these products had the amino terminus nucleic acid sequences that were expected by homology with chicken and rat sequences, some had novel sequences that revealed the presence of unsuspected alternative exons. The present invention provides, for the first time, the sequences of these exons and their location in the genomic structure of α7.

Total RNA was isolated from normal human hippocampus by the method of Chomczynski and Sacchi (Chomczynski and Sacchi, Anal. Biochem., 162:156 [1987]). Briefly, brain tissue from the human hippocampus was disrupted in the presence of Solution D (4 M guanidium thiocyanate, 25 mM sodium citrate (pH 7.0), 5% sarcosyl, 0.1 M 2-mercaptoethanol) in a tissue homogenizer. The homogenized tissue was acidified with 0.1x volume of 2 M sodium acetate, pH 4.0, with "X" referring to the initial volume of Solution D. The acidified tissue homogenate was extracted with 1x volume of water-saturated phenol and 0.2 volume of chloroform:isoamyl alcohol (49:1). The phases were separated by centrifugation (the supernatant contains RNA whereas the DNA and proteins remain in the interphase and the phenol). The RNA was precipitated by adding an equal volume of isopropanol (20° C.), centrifuged and the pellet resuspended in 1 mM EDTA, pH 8.0. The concentration of the RNA was determined by measuring the absorbance at 260 and 280 nm.

The first strand cDNA synthesis for 5'-RACE was performed as indicated in the manufacturer's instructions, with the addition of methylmercuric hydroxide (7 mM) to reduce secondary structure. The cDNA was synthesized using a human gene-specific antisense oligonucleotide: 5'-AGGACCCAAACTTCAG-3' (SEQ ID NO:48), complementary to 5'-sequence in the longest human clone from the primary cDNA screen. Following cDNA synthesis, terminal deoxynucleotide transferase was used to attach homopolymeric (dCTP) tails to the 3' ends of the cDNA. A nested gene specific antisense primer and an anchor primer from the 5'-RACE kit, both containing triplet repeat sequences for annealing to the pAMP1 vector, were used for PCR amplification of a homopolymeric, tailed cDNA product. The sequences of the primers were: for the antisense primer, 5'-CAUCAUCAUCAUCCAGCGTACATCGATGT AGCAGGAACTCTTGAATAT-3' (SEQ ID NO:49), and the anchor primer 5'-CUACUACUACUAGGCCACGCGTCGACTAGT ACGGGIIGGIIGGGIIG-3' (SEQ ID NO:50). In this anchor primer sequence, the "I" is inosine.

Briefly, the final composition of the PCR reaction for amplification of dC-tailed cDNA was as follows: 20 mM Tris-HCl (pH 8.4), 50 mM KCl, 1.5 mM $MgCl_2$, 400 nM for both primers, 200 μM each dNTP, 8% DMSO and 0.2 unit/μl Taq DNA polymerase. The PCR program was as follows: 94° C., 1 min; 57° C., 30 sec; 72° C., 2 min for 35 cycles; final extension at 72° C. for 10 min, then soak at 4° C.

PCR products were Glassmax (Gibco-BRL) purified and reamplified with the same reaction conditions using the following program: 94° C., 1 min; 50° C., 30 sec; 72° C., 2 min for 5 cycles; 94° C., 1 min; 55° C., 30 sec; 72° C., 2 min for 35 cycles; extension at 72° C. for 7 min, and soak at 4° C. Products from this PCR reaction were then gel purified and cloned into the pAMP1 vector (Gibco-BRL) with uracil DNA glycosylase according to manufacturer's directions, for subsequent automated sequencing, as described in Example 5.

A group of novel exons located in YAC, PAC and BAC clones containing the full-length gene and/or the duplicated α7 sequences was also evidenced. These novel exons were discovered in the process of comparing RACE clones, isolated during cloning of the α7 human cDNA, with EST cDNA clones (EST 3952 and EST 52861) found in the EST Database (NCBI) by homology screening. During cloning of the 5'end of the α7 coding region, the RACE technique was used to amplify the 5'end of the α7 cDNA (Frohman, supra). Although cDNA clones which matched sequence for published human α7 from a neuroblastoma cell line SH-SY5Y (Peng et al., Mol. Pharm., 45:546 [1994]), were obtained, clones with 5' sequence that could not be identified were also obtained.

When EST cDNA clones were subsequently found in the EST database by homology screening, several were identified that had exons 5–10 and unknown sequence 5' of exon 5. Comparison of the 5' ends of the RACE and EST products showed that the novel sequences are partially homologous. PCR primers were designed to these novel sequences for amplification from genomic DNA. Intronic sequence and consensus splice junctions that identified these sequences as four alternatively spliced and previously unreported exons were then identified. The sizes and splice junctions for these novel exons, designated as α7D, α7C, α7B, and α7A are shown in FIG. 6. In this Figure, the sequence of the RACE clone (Genbank #AFO29838) is shown in uppercase, while intron boundaries are shown in lowercase, and are not included in the nucleotide numbering. The sizes of the exons are indicated below the exon designations. RACE clones, containing these novel exons were previously deposited with GenBank (RACE D-C-B-A-5-6; AFO29838; RACE D-C-A-5-6, Genbank; #AFO29839).

EXAMPLE 8

RT-PCR Analysis

Total RNA was isolated from normal human hippocampus, human cingulate gyrus, the SH-SY5Y neuroblastoma cell line, and human immortalized lymphocytes with TRIzol reagent (Gibco-BRL) following manufacturer's instructions. The mutations seen in the PAC, BAC, YAC and published α7 sequences were screened in seven normal subjects and SH-SY5Y cells. DNA was evaluated for all subjects, while cDNA was evaluated in exons 1–10 and exons 5–10 for all subjects, and exons D-10 were evaluated in one normal subject and SH-SY5Y cells. The DNA and RNA were obtained as detailed above. The cDNA was generated as previously detailed.

Total RNA was isolated from normal human hippocampus, human cingulate gyrus and SH-SY5Y neuroblastoma cell line by the TRIzol reagent (Gibco-BRL) following manufacturer's directions. RNA was stored as an ethanol precipitate until centrifugation and resuspended in 1 mM EDTA, pH 8.0 prior to cDNA preparation.

Total RNA was reverse transcribed at 42° C. for 60 min in a 40 μl volume with Superscript II reverse transcriptase (Gibco-BRL) and random hexamer primers (Pharmacia). The final concentration of the components of the reaction were as follows: 1×first strand buffer (50 mM Tris-HCl, pH 8.3, 75 mM KCl, 3 mM MgCl$_2$), 1 mM dATP, 1 mM dGTP, 1 mM dCTP, 1 mM dTTP, 8 μM random hexamers, 10 mM DTT, 0.5 u/μl placental Rnase inhibitor (Boehringer-Mannheim), 2.5 u/μl Superscript II reverse transcriptase and 500 ng of total RNA.

Primary PCR of the exon 1–10, exon 5–10 and exon D-10 products was performed using the Advantage-GC cDNA PCR kit (Clontech). Briefly, 5 μl of RT products were diluted to 50 μl with 40 mM Tricine-KOH, pH 9.2 at 25° C., 15 mM KOAc, 3.5 mM Mg(OAc)$_2$ 5% DMSO, 3.75 μg/ml BSA, 0.2 mM of each dNTP, 0.2 μM of each primer, 1 M GC-Melt and 1×Klentaq-1 DNA polymerase mix. Samples were incubated in a Perkin-Elmer 480 DNA Thermocycler.

For Exon 1–10, the sense primer was 5'-CGCTGCAGCTCCGGGACTCAACATG-3' (SEQ ID NO:51), and the antisense primer was 5'-TGCCCATCTGTGAGTTTTCCACATG-3' (SEQ ID NO:52). The PCR conditions were 94° C., 1 Lin; 5 cycles at 94° C., 30 sec, 72° C., 3 min; 5 cycles at 94° C., 30 sec, 70° C., 3 min; 25 cycles at 94° C., 20 sec, 68° C., 3 min; final extension at 68° C., 3 min and soak at 4° C.

For Exon 5 to 3'UT α7 transcript, the sense primer was 5'-TGACGCCACATTCCACACTAA-3' (SEQ ID NO:53), and the antisense primer was 5'-CCCCAAATCTCGCCAAGC-3' (SEQ ID NO:54). The PCR conditions were 5 cycles at 96° C., 1 min, 50° C., 30 sec, 72° C., 1 min; 30 cycles at 95° C., 30 sec, 62° C., 20 sec. 72° C., 30 sec; final extension at 68° C., 3 min and soak at 4° C.

For Exons D-10, the sense primer was 5'-CTCGGTGCCCCTTGCCATTT-3' (SEQ ID NO:55), and the antisense primer was 5'-CCTTGCCCATCTGTGAGTTTTCCAC-3' (SEQ ID NO:56). The PCR conditions were 94° C. 1 min, 5 cycles 94° C., 30 sec, 70° C., 3 min 5 cycles 94° C. 30 sec, 68° C., 3 min, 25 cycles 94° C. 20 sec, 66° C. 3 min 1 cycle 68° C. 3 min, cool to 4° C.

The products generated from exons 1–10, 5–10 and D-10 were further amplified to incorporate M13 primer sequences into products small enough to sequence in both directions. PCR conditions were as follows for all secondary, nested PCR amplifications. Perkin-Elmer Core reagents were used in standard concentrations using 2 mM MgCl$_2$, 0.1 mM each dNTP, 1.5 U Taq Gold, 10% DMSO and 25 pM of each primer in a 50 μL reaction. PCR reactions were heated at 96° for 5 min, then 5 cycles were performed at 96° C. for 1 min, 60° C. for 30 sec, 72° C. for 1 min; then 30 cycles for 95° C. for 30 sec, 68° C. for 20 sec, and 72° C. for 30 sec, followed by a 7 min 72° C. extension and cooling at 4° C.

All cDNA reactions were performed in duplicate using 50 ng RNA equivalents in a primary reaction, encompassing the full cDNA length of interest, then reamplified in nested, secondary PCR reactions to incorporate M13 primers into shorter products. DNA amplifications were performed in duplicate from 100 ng of needle-sheared template, within exon boundaries. The duplicates were then pooled, Centricon 100 (Amicon) column purified and sequenced using standard M13 Dye Primer chemistry on an ABI 373 Automated sequencer. All templates were sequenced bi-directionally, except where sequence length did not allow a nested primer. Alternate splice products were hand called from the electropherograms. Clean sequences were aligned and checked with Sequencher Software (Gene Codes Corporation).

DNA products were generated with primer pairs 1552/1553, 1101/1102, 1097/1098 and 1099/1100 to check the 497–498 deletion, 654/690, and 1269/1335 mutations, respectively. These primers are shown in Table 3, below. In this Table, "1ry" and "2ry" refer to the first and second primer sets in nested PCR. The cDNA amplifications required three sets of primary amplifications, exons 1–10, exons 5–10 and exons D-10. Primer pair 1381/1382 was used to amplify exons 1–10; primers 1482/1483, 1101/1098 and 1099/1481 were then used as nested primers from this primary PCR to check 497–498, 654/693 and 1269/1335 respectively. The exon 5–10 product was amplified with primer pair 1502/1503, nested primers 1502/1483, 1101/1098 and 1099/1481 were used to check 497/4981654/693, 654/690 and 1269/1335 respectively. Exons D-10 were amplified with primers 1569/1562, and the nested primers 1553/1098 and 1097/1481 were used to check 497–498/654/690 and 1269/1335, respectively. Redundancy in the overlap of the secondary PCR products was used to double check some mutations, necessary when alternate splicing or base pair deletions occurred, making some base calls difficult.

Exon 3 codes for 15 amino acids near the amino terminal, in the extracellular domain. An alternate transcript without this exon appears in most PCR amplifications of this region, at a somewhat diminished concentration in comparison to the full-length transcript.

To determine if the exon 5–10 copy of α7 was expressed, a second RT-PCR product was generated, encompassing only exons 5–10. The bases which appeared to be heterozygous in the DNA, but which are not heterozygous in the exon 1–10 transcript, are now fully accounted for in the 5–10 exon product, showing the exon 5–10 gene to be expressing as cDNA. The base changes fall into three categories, those seen only in the full-length 1–10 transcript, those changes present only in the 5–10 transcript and bases changes seen in both transcripts.

The TG deletion at 497–498 is only present in the 5–10 transcript; the C at 654 can be assigned to the 1–10 transcript, the T to the 5–10 transcript; the G at 933 can be assigned to both transcripts with an A in some subjects' 1–10 transcript and at 1335 the T can be assigned to the 1–10 transcript. The base changes seen at 690 and at 1269 appear to be present in both copies of the gene. These data are consistent with the base changes seen in the YAC, PAC and BAC clones, and the assignment of each clone to the duplicated or original gene.

TABLE 3

Primer Sequences

| Primer Number and Description | Sequence | SEQ ID NO: |
|---|---|---|
| 1097 sense m13fwd+ | CCCAGTACTTCGCCAGCACCATGAT | SEQ ID NO:57 |
| 1098 antisense m13rev+ | CCCCGTCGGGGTCGTGGTGGTGGTA | SEQ ID NO:58 |
| 1101 sense m13fwd+ | TCCCCGGCAAGAGGAGTGAAAGGTT | SEQ ID NO:59 |
| 1102 antisense m13rev+ | ACACCAGCAGGGCGAGGGCGGAGAT | SEQ ID NO:60 |
| 1099 sense m13fwd+ | GACCAGAGTCATCCTTCTGAACTGG | SEQ ID NO:61 |
| 1100 antisense m13rev+ | TTTCAGGTAGACCTTCATGCAGACA | SEQ ID NO:62 |
| 1553 sense m13fwd+ | CGATGTACGCTGGTTTCCCTTTGAT | SEQ ID NO:63 |
| 1552 antisense m13rev+ | TTCCCACTAGGTCCCATTCTCCATT | SEQ ID NO:64 |
| 1382 sense 1ry cDNA | CGCTGCAGCTCCGGGACTCAACATG | SEQ ID NO:65 |
| 1381 antisense | TGCCCATCTGTGAGTTTTCCACATG | SEQ ID NO:66 |
| 1502 sense 1ry cDNA | TGACGCCACATTCCACACTAA | SEQ ID NO:67 |
| 1503 antisense | CCCCAAATCTCGCCAAGC | SEQ ID NO:68 |
| 1569 sense 1ry cDNA | CTCGGTGCCCCTTGCCATTT | SEQ ID NO:69 |
| 1562 antisense | CCTTGCCCATCTGTGAGTTTTCCAC | SEQ ID NO:70 |
| m13 sense extension | TGTAAAACGACGGCCAGT | SEQ ID NO:71 |
| m13 antisense extension | CAGGAAACAGCTATGACC | SEQ ID NO:72 |
| 1482 sense m13fwd+ 2ry cDNA | AAGGAGCTGGTCAAGAACTACAATC | SEQ ID NO:73 |
| 1483 antisense m13rev+ | CCGGAATCTGCAGGAAGCAGGAACA | SEQ ID NO:74 |
| 1101 sense m13fwd+ 2ry cDNA | TCCCCGGCAAGAGGAGTGAAAGGTT | SEQ ID NO:59 |
| 1098 antisense m13rev+ | CCCCGTCGGGGTCGTGGTGGTGGTA | SEQ ID NO:58 |
| 1502 sense 2ry cDNA | TGACGCCACATTCCACACTAA | SEQ ID NO:67 |
| 1483 antisense m13rev+ | CCGGAATCTGCAGGAAGCAGGAACA | SEQ ID NO:74 |
| 1553 sense m13fwd+ 2ry cDNA | CGATGTACGCTGGTTTCCCTTTGAT | SEQ ID NO:63 |
| 1098 antisense m13rev+ | CCCCGTCGGGGTCGTGGTGGTGGTA | SEQ ID NO:58 |
| 1097 sense m13fwd+ 2ry cDNA | CCCAGTACTTCGCCAGCACCATGAT | SEQ ID NO:57 |
| 1481 antisense m13rev+ | CCAGGCGTGGTTACGCAAAGTCTTTG | SEQ ID NO:75 |
| 1099 sense m13fwd+ 2ry cDNA | GACCAGAGTCATCCTTCTGAACTGG | SEQ ID NO:61 |
| 1481 antisense m13rev+ | CCAGGCGTGGTTACGCAAAGTCTTTG | SEQ ID NO:75 |

An RT-PCR product was generated from exon α7D to exon 10 from one normal brain and from SH-SY5Y cells. The resulting cDNA product contained alternate splice products with exons shown in FIG. 2. The 2 base pair deletion seen at bases 497–498 in the DNA that is not present in the exon 1–10 transcript was seen in the D-10 transcript, while all of the D-10 product in SH-SY5Y was deleted at 497–498, and subject SL061 was heterozygous for the deletion in the D-10 product. The presence of the T at base 757 connects this base change to the TG deletion. The G at 690 was not expressed in either cDNA. The A at 933 was not present in the minus TG strand of SH-SY5Y. The T at 1296 was expressed in subject SL061. These products, in subject SL061 cannot differentiate between the exon 5–10 product splicing to exon D versus exon 1, however the product in D-10 from SH-SY5Y can, since only the minus TG strand was expressed, negating the possibility that exons 5–10 from the 1–10 gene are splicing to exon D.

These new exons have been designated as 3'α7A, α7B, α7C, α7D 5'. The RACE products were variable in their inclusion of Exon B, similar to the EST clones. However, PCR products including exons D-10 gave many alternate splice products between exons D, C, B, 5 and 6. This same phenomenon was seen in the exon 1–10 transcripts between exons 2 and 6. Based on these results, it was not possible to fully evaluate whether any of the D-10 transcript contain only exons 5–10 from the duplicated region or if this transcript contains some splicing of 5–10 from the 1–10 full gene sequence, since the cell line and the brain gave differing results. Subcloning is used to fully evaluate the base changes to separate the various splice products.

These results indicate that the primer sequences described herein can be successfully used to screen both genomic DNA and mRNA for the presence in DNA and the expression in mRNA of sequences which are polymorphic (i.e., different) between individuals. Standard automated and hand sequencing methodologies are used to locate differences in samples obtained from individuals. It is contemplated that some of these polymorphisms, as well as others, have pathogenic roles. These polymorphisms are also used to relate the inheritance of specific alleles of α7 genes through families to the presence of illness or physiological dysfunction, using standard methods known in the art for linkage analysis.

EXAMPLE 9

Single Strand Conformation Polymorphism (SSCP) Analysis

PCR products, <200 bp, containing a single sequence variant were amplified with $^{33}$Pγ-ATP kinased primer sets using Promega T4 kinase as known in the art (See e.g., Dracopoli et al., supra). The primers used in this Example were:

TABLE 4

Primers Used for SSCP Analysis

| Exon and Primer Number | Sequence | SEQ ID NO: |
|---|---|---|
| Exon 6b #1243 | GATGTGCAGCACTGCAAACAA | SEQ ID NO:76 |
| Exon 6b #1144 | TTAAAGCTTGCCCAGGAATAGG | SEQ ID NO:77 |
| Exon 6d #1124 | GGAACTGCTGTGTATTTTCAGC | SEQ ID NO:78 |
| Exon 6d #1245 | AAGACCAGGACCCAAACTTGT | SEQ ID NO:79 |
| Exon 7d #1143: | GCTTGTGTGTGGTATACACATTG | SEQ ID NO:80 |
| Exon 7 #675 | GTAGAGTGTCCTGCGGC | SEQ ID NO:81 |
| Exon 10 (1438) #672 | GGTCCGCTACATTGCCAA | SEQ ID NO:82 |
| Exon 10 #593 | TGATGGTGAAGACCGAGAAGG | SEQ ID NO:83 |

Products, denatured with loading dye (7.26 M urea, 60% formamide, 22 mM EDTA, 32 mM NaOH, 0.25% bromophenol blue, 0.25% xylene cynol), were analyzed on GeneAmp detection gels (Perkin Elmer) run at both 6° C. and 25° C., using Bio Rad PowerPac 3000 with a temperature probe, as described by the manufacturer.

Thus, the frequency of these sequence variants was examined, using SSCP in a group of 43 normal control subjects with no history of mental illness. Primer sets derived from the exon and intron-exon boundary sequences are used to amplify 200 bp portions of the gene from individuals with schizophrenia and their relatives, in order to identify sequence changes that affect gene function. Sequence changes that are not known to affect gene function, but can serve as markers to trace heritability of particular gene regions through families, are also identified in this process. The −2 bp deletion and the heterozygosities at 654, 690, 1269, at 1335 were found in this Example.

Almost all subjects were heterozygotic at positions 654 and 690. Nucleotide positions 1269 and 1335 were also found to be polymorphic, suggesting that the duplicated sequences have diverged since the duplication event.

These results indicate that the primer sequences described herein can be successfully used to screen genomic DNA in SSCP, a standard genome screening technique, for polymorphic differences in DNA sequences between individuals. It is contemplated that these polymorphisms, as well as others, have pathogenic roles. These polymorphisms are also used to relate the inheritance of specific alleles of α7 genes through families to the presence of illness or physiological dysfunction, using standard methods known in the art for linkage analysis.

EXAMPLE 10

Electrophysiological Recording, Linkage Analysis, and Nonparametric Methods

Electroencephalographic activity was recorded at the vertex and electrooculographic activity was recorded from the superior orbital-lateral canthus. Five averages of sixteen responses each to paired clicks were obtained, using standard methods (See, Griffith et al., Psychophysiology 32:460 [1995]), for the specific technique). The P50 responses were distinguished from pre-stimulus activity for both normals and schizophrenics at a high level of significance (P<0.001). The averages were reviewed by two investigators, blind to genetic information, who rejected any average containing excessive electrooculographic activity, drowsiness, startle, or other artifacts; the remainder were combined into a grand average, from which the P50 amplitudes were measured and their ratio (second response/first response) was calculated automatically by a computer algorithm (Nagamoto et al., Biol. Psychiat., 25:549 [1989]). Seven subjects were not used, because artifact-free averages could not be selected from their recordings. Recordings were initially performed, then repeated approximately three years later. The earlier recordings were reanalyzed for 2 subjects who were later deceased, for 10 subjects who refused repeat recording, and for 2 patients who were later on atypical neuroleptics, which can normalize the P50 ratio; other neuroleptic medication do not affect the phenotype (Nagamoto et al., Biol. Psychiat., 40:181 [1996]).

Parameters for lod score analyses of P50 ratios were determined from the distribution of values in 43 unrelated normal individuals and 36 unrelated schizophrenic patients (Waldo et al., Schizophr. Res., 12:93 [1991]) and from observations of the segregation of P50 ratios in the nine multiplex schizophrenic families (i.e., the families described in Example 1). Elevated P50 ratios were defined as values greater than or equal to 0.50, which were found in 91% of the unrelated schizophrenics and 6% of the normals. Of the remaining unrelated schizophrenics, most had values between 0.41 and 0.49, a range therefore coded unknown for the linkage analysis. If this unknown range was extended to include values between 0.40 and 0.60, the results were changed substantially (e.g., lod scores were decreased by an average of 0.54 across the markers in the 15q13-14 region due to the loss in information). For lod score analyses, frequency of a gene for abnormal P50 ratio was fixed at 0.05, penetrance for the normal genotype was fixed at 0.01, and penetrance for the abnormal genotypes was fixed at 0.8 (Coon et al., Biol. Psychiat., 34:277 [1993]). These parameters result in a morbidity for abnormal P50 ratio of 8.7% and a phenocopy rate among abnormal subjects of 10.4%. The FASTLINK version of the LINKAGE program was used to compute lod scores at various recombination fractions, Θ (Lathrop et al., Proc. Natl. Acad. Sci., 81:3443 [1984]). No significant heterogeneity was found using the HOMOG program (Ott, Analysis of Human Genetic Linkage, Johns Hopkins Univ. Press, Baltimore [1991]). The chance of false positive lod score results was determined using SLINK (Ott, Proc. Natl. Acad. Sci., 86:4175 [1989]); 1000 replicates of the pedigrees were simulated, assuming no linkage to the marker under analysis. Lod score analysis was performed for each replicate under the dominant model; the highest score observed for D15S1360 and P50 under the assumption of no linkage was 1.87.

Sibling pair analysis was performed using the SIBPAL program (Elston, SIBPAL, Statistical Analysis for Genetic Epidemiology, Louisiana State Univ. Medical Center, New Orleans, La., version 2.2 [1995]). Marker data were used to estimate the proportion of alleles shared through a common ancestor (i.e., identical by descent) for each possible sibling pairing within the linkage families. A test was performed to determine if the proportion of alleles shared was >0.50 for abnormal/abnormal pairs. To calculate P values, 1000 replicates of the 9 families were simulated for each marker to determine empirical distributions. Degrees of freedom were adjusted downward for non-independence when multiple pairings were used from the same sibship within a family.

A newly developed method, Nonparametric Linkage, uses information from all genotyped members of a pedigree to assess the extent of alleles shared identical by descent among all affected individuals. The resulting statistic is normalized by first subtracting the expected sharing score under the null hypothesis of no linkage from the observed score and then dividing by the score variance under the null hypothesis. Thus the statistic is asymptotically distributed as a standard normal variable (Z score) under the null hypothesis. Calculations of Nonparametric Linkage statistics were carried out using the GENEHUNTER computer programs (Elston, supra). GENEHUNTER also uses an improvement to a previously described algorithm to perform complete multipoint linkage analysis with a large number of highly polymorphic markers in pedigrees of moderate size (Kruglyak et al., Am. J. Hum. Genet., 58:1347 [1996]). Due to computational constraints, the three largest pedigrees were each split into two parts.

Only one marker, D15S1360, yielded a lod score >3.0 (lod score maximum=5.3, theta=0.0, P<0.001). DNA markers flanking D15S1360 also gave positive lod scores. Multipoint analysis showed a maximum lod score at D15S1360 of 5.29. Both the sibpair analysis and nonparametric linkage analysis gave confirming positive results of similar statistical significance. The sibpair analaysis showed 0.70 proportion of D15S1360 alleles among siblings with abnormal P50 ratios (T=4.07, P<0.0005). Two point results from the non-parametric analysis were most significant for D15S1360 (Z=3.95, P<0.0002). A complete multipoint analysis using nine chromosome 15q markers gave a maximum value at D15S1360 (Z=5.04, P<0.000016).

From the above it should be clear that the present invention provides gene sequences encoding mammalian α7 genes and proteins. The present invention further provides compositions and methods for targeted therapy directed to α7 abnormalities.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated nucleotide sequence consisting of a portion of the human alpha-7 neuronal nicotinic receptor, set forth as nucleotides 1–392 of SEQ ID NO:94.

2. A vector comprising the nucleotide sequence of claim 1.

3. An isolated host cell transformed with the vector of claim 2.

4. The host cell of claim 3, wherein said cell is selected from the group consisting of a bacterial cell, a yeast cell, an amphibian cell and a mammalian cell.

5. An isolated nucleotide sequence consisting of a 5' portion of the human alpha-7 neuronal nicotinic receptor and exon 1, as set forth as nucleotides 1–447 of SEQ ID NO:94.

6. An isolated nucleotide sequence consisting of a 5' portion of the human alpha-7 neuronal nicotinic receptor, exon 1, and the intron 1 slice donor, as set forth as nucleotides 1–457 of SEQ ID NO:94.

* * * * *